(12) United States Patent
Huang et al.

(10) Patent No.: US 11,655,308 B2
(45) Date of Patent: May 23, 2023

(54) HM-3 FUSION PROTEIN AND APPLICATION THEREOF

(71) Applicant: TASLY BIOPHARMACEUTICALS CO., LTD., Shanghai (CN)

(72) Inventors: Ruijing Huang, Shanghai (CN); Baoqing Fan, Shanghai (CN); Jian Li, Shanghai (CN); Xiaohui Ma, Shanghai (CN); Yibo Wang, Shanghai (CN); Lihua Zhang, Tianjin (CN); Xiaodan Cao, Shanghai (CN); Wenlei Li, Shanghai (CN); Pengyin Wang, Shanghai (CN); Yan Chen, Shanghai (CN)

(73) Assignee: TASLY BIOPHARMACEUTICALS CO., LTD., Shanghai (CN)

( * ) Notice: Subject to any disclaimer, the term of this patent is extended or adjusted under 35 U.S.C. 154(b) by 228 days.

(21) Appl. No.: 16/768,619

(22) PCT Filed: Nov. 23, 2018

(86) PCT No.: PCT/CN2018/117188
§ 371 (c)(1),
(2) Date: Sep. 23, 2020

(87) PCT Pub. No.: WO2019/109819
PCT Pub. Date: Jun. 13, 2019

(65) Prior Publication Data
US 2021/0009717 A1 Jan. 14, 2021

(30) Foreign Application Priority Data
Dec. 6, 2017 (CN) .......................... 201711273473.9

(51) Int. Cl.
*C07K 19/00* (2006.01)
*A61K 9/00* (2006.01)
*A61K 38/16* (2006.01)

(52) U.S. Cl.
CPC ............ *C07K 19/00* (2013.01); *A61K 9/0019* (2013.01); *A61K 9/0053* (2013.01); *A61K 38/16* (2013.01); *C07K 2319/30* (2013.01)

(58) Field of Classification Search
CPC .. C07K 2319/30; C07K 7/08; C07K 2319/00; A61K 38/10; A61K 38/16
See application file for complete search history.

(56) References Cited

U.S. PATENT DOCUMENTS

| 2014/0329759 A1* | 11/2014 | Xu ........................ | C07K 14/78 514/19.2 |
| 2014/0378384 A1* | 12/2014 | Xu ........................ | A61P 29/00 530/324 |

FOREIGN PATENT DOCUMENTS

| CN | 102417540 A | 4/2012 | |
| CN | 102516393 A | 6/2012 | |
| CN | 102558358 A | 7/2012 | |
| CN | 102850443 A | 1/2013 | |
| CN | 102936288 A | 2/2013 | |
| CN | 104059132 A | 9/2014 | |
| CN | 105646717 A | 6/2016 | |
| CN | 108623692 A | 10/2018 | |
| CN | 108623693 A | 10/2018 | |
| EP | 2784093 A1 | 10/2014 | |
| WO | WO-2014015054 A1 * | 1/2014 | ............. A61K 31/44 |

OTHER PUBLICATIONS

Strohl, "Fusion Proteins for Half-Live Extension of Biologics as a Strategy to Make Biobetters", BioDrugs, 2015, pp. 215-239 (Year: 2015).*
Chen et al.; "Fusion Protein Linkers: Property, Design and Functionality"; Adv Drug Deliv Rev.; vol. 65; Oct. 2013; p. 1357-1369.
Hong et al.; "PEGylated HM-3 presents anti-rheumatic bioactivity by inhibiting angiogenesis and inflammation"; J. Mater. Chem. B; vol. 2; 2014; p. 800-813.
Hu et al.; "An integrin αvβ3 antagonistic modified peptide inhibits tumor growth through inhibition of the ERK and AKT signaling pathways"; Oncology Reports; vol. 36; 2016; p. 1953-1962.
Huang et al.; "The Protective Effect of a Long-Acting and Multi-Target HM-3-Fc Fusion Protein in Rheumatoid Arthritis"; Int'l Journal of Molecular Sciences; vol. 19; 2018; 17 pages.
Jing et al.; "Inhibition of ovarian cancer by RGD-P125A-endostatin-Fc fusion proteins"; Int'l Journal of Cancer; vol. 129; 2011; p. 751-761.
Yuan et al.; "Pharmacokinetics of HM-3 After Intravitreal Administration in Mice"; Current Eye Research; vol. 39; 2014; p. 837-844.
Zhu et al.; "Site-specific modification of anti-angiogenesis peptide HM-3 by polyethylene glycol molecular weight of 20 kDa"; The Journal of Biochemistry; vol. 148; 2010; p. 341-347.

(Continued)

*Primary Examiner* — Lianko G Garyu
(74) *Attorney, Agent, or Firm* — BakerHostetler

(57) ABSTRACT

The present invention belongs to the technical field of biological pharmacy, and particularly relates to a long-acting HM-3 fusion protein molecule and an application thereof. In the present invention, on the basis of the sequence of HM-3 molecule, an active polypeptide HM-3 and derivatives thereof are linked to a human Fc (IgG) fragment or a fragment of an Fc (IgG) mutant directly or by a linker peptide (Linker), thus forming a novel molecular entity. The general formula of the molecular entity is $(HM-3)_n$-Linker-Fc(IgG), Fc(IgG)-Linker-$(HM-3)_n$, or $(HM-3)_n$-Linker-Fc(IgG)-Linker-$(HM-3)_n$. The fusion protein effectively prolongs the half-life of HM-3, is low in cost and overcomes the major problem of druggability of small peptides. Therefore, the fusion protein of the present invention may serve as a potential drug for the treatment of autoimmune diseases, neovascular diseases, osteoarthritis and the like.

11 Claims, 32 Drawing Sheets
Specification includes a Sequence Listing.

(56) References Cited

OTHER PUBLICATIONS

European Patent Application No. 18884891.5; Extended Search Report; dated Aug. 12, 2021; 13 pages.
International Patent Application No. PCT/CN2018/117188; Int'l Search Report; dated Feb. 21, 2019; 4 pages.
Wang et al.; "The progress of research and development of integrin inhibitors"; China Modern Medicine; vol. 20 Issue 7; Jun. 2013; p. 29-32 (contains English Abstract).

* cited by examiner

HM-3 FUSION PROTEIN AND APPLICATION THEREOF

CROSS-REFERENCE TO RELATED APPLICATIONS

This application is a U.S. national phase application under 35 USC 371 of PCT/CN2018/117188 filed Nov. 23, 2018, and claims priority to CN201711273473.9 filed Dec. 6, 2017, which are incorporated herein by reference in their entirety.

SEQUENCE LISTING

This application contains a Sequence Listing which has been submitted electronically in ASCII format and is hereby incorporated by reference in its entirety. Said ASCII copy, created on Mar. 24, 2020, is named 107244_000019_SL.txt and is 46,210 bytes in size.

TECHNICAL FIELD

The invention belongs to the technical field of biological pharmacy, and particularly relates to a long-acting HM-3 fusion protein molecule and an application thereof.

BACKGROUND ART

Autoimmune diseases refer to diseases caused by body's immunoreaction to autoantigen, resulting in tissue injury thereof. If autoimmune disease is not controlled effectively in time, it causes very serious consequences and even endangers lives. Common autoimmune diseases include: systemic lupus erythematosus, rheumatoid arthritis, sclerodenna, hyperthyroidism, juvenile diabetes, idiopathic thrombocytopenic purpura, autoimmune hemolytic anemia, ulcerative colitis, as well as a wide variety of skin diseases, autoimmune liver diseases, and the like.

Rheumatoid arthritis (RA) is a systemic chronic autoimmune disease characterized by joint synovitis. Persistent and recurrent episodes of synovitis may lead to the damage on articular cartilage and bones, joint dysfunction, and even disability. Vasculitis involves all organs of our body, so it is called rheumatoid disease.

Inflammatory autoimmune diseases represented by rheumatoid arthritis are high in morbidity and disability rate, and there are more than ten million patients in China; therefore, it is a kind of major diseases influencing human health and quality of life. TNF α inhibitors are mainstream biological agents in the treatment of rheumatoid arthritis at present; in 2013, the total sales of three TNF α inhibitors, namely, HUMIRA®, ENBREL® and REMICADE® was $28.108 billion, occupying 84.58% of the total sales in the global market of rheumatoid arthritis. However, to achieve a better therapeutic effect, TNF inhibitors need to be used in combination with methotrexate, while some rheumatoid arthritis patients are intolerant to methotrexate, resulting in the failure of such combined therapy. In addition, clinical statistics indicate that about 30% to 40% of patients treated with the TNFα inhibitor combination treatment of TNF α inhibitors still do not response to the treatment regimen, which fails to achieve the major therapeutic indicator (20% symptom relief). Therefore, besides TNF α inhibitors, the major mainstream pharmaceuticals companies have actively studied other hot biological drug targets for the treatment of rheumatoid arthritis currently, such as, JAK inhibitors, interleukin inhibitors, inflammatory cell infiltration inhibitors, cyclophilins and integrin blockers. These drugs can supplement each other with TNF α inhibitors to provide a variety of pharmaceutical options for the patients suffering from different types of rheumatoid arthritis.

The so-called new blood vessel is a kind of spiral capillary newly protruding from a common blood vessel. New blood vessels may occur in human body under certain conditions, e.g., pregnancy and the like, and moreover, specific diseases may be caused by the occurrence of new blood vessels, and these diseases are collectively referred to as "neovascular diseases", such as cancers, wet macular degeneration. Wet macular degeneration, also known as neovascular macular degeneration, is clinically featured by the formation of choroidal neovascularization primarily.

Osteoarthritis is a kind of degenerative diseases, namely, injury of cartilago articularis degeneration, reactive hyperplasia of joint edge and subchondral bone caused by aging, obesity, strain, trauma, congenital abnormality of joint, joint deformity and many other factors. It is also known as osteoarthropathy, degenerative arthritis, senile arthritis, hypertrophic arthritis and so on. Osteoarthritis is clinically featured by slowly-developing joint pain, tenderness, stiffness, joint swelling, confined activity, joint deformities, etc.

HM-3 is a polypeptides of 18 amino acid residues containing an arginine-glycine-aspartic acid sequence (RGD sequence), and the amino acid sequence is as follows:

Ile-Val-Arg-Arg-Ala-Asp-Arg-Ala-Ala-Val-Pro-Gly-Gly-Gly-Gly-Arg-Gly-Asp (SEQ ID NO: 3)

HM-3 has a known structure and has been disclosed in CN1314705C. HM-3 has high affinity to an integrin αvβ3 and inhibits the expression of VEGF and TNFα by blocking the signal pathway of integrin αvβ3, thus inhibiting endothelial cell migration and neovascularization, as well as inhibiting RA synovial hyperplasia thereby. Acute, subacute and chronic inflammation tests in mice body showed that: HM-3 could simultaneously inhibit angiogenesis and inflammatory reaction, regulate the content of VEGF and TNFα in synovial tissues of collagen-induced arthritis (CIA) DBA/1 mice to effectively relieve RA symptoms, and moreover, its therapeutic effect is better than methotrexate.

Although the HM-3 molecule has the advantages of clear efficacy and good safety, the in vivo half-life of the small peptide is only 27.66±7.37 minutes; if the product is put into clinical use, it needs to administrate the drug for once or twice per day, greatly limiting its clinical application. In the art, modification or transformation of the molecular structure is a common method to solve the problems of short half-life and continuous administration, of which chemical modification is applied most extensively.

A polyethylene glycol (PEG)-modified HM-3: mPEG-SC-HM-3 has been disclosed in a Chinese patent application CN102417540A, and its half-life is much higher than HM-3.

However, there are various problems in PEG modification itself. PEG modification achieves the reduction of immunogenicity and extension of half-life by covering proteins, therefore, PEG modification is not suitable for all proteins. Namely, some proteins cannot be modified normally as the modification site is not exposed; some are covered on active sites, resulting in the activity decrease; after modified, some proteins change in conformation, resulting in decreased activity or easy aggregation. PEG-modified products must gradually expose drug proteins through the degradation of PEG molecules, but low molecular weight PEG has renal toxicity, and high molecular weight PEG has unclear degradation mechanism in vivo, which brings obvious administration risks to PEG-modified drugs. In addition, as PEG modification relates to a complex protein process and the length of PEG molecules is different to make the molecular weight of PEG-modified products not uniform, which drops the uniformity of finished products while increasing the production cost, bringing difficulties to industrialization.

The invention provides an HM-3-Fc fusion protein and application thereof, so as to overcome the problems of short in vivo half-life of HM-3 protein, high synthesis cost of polypeptide, unsuitability for industrial production and the like.

SUMMARY OF THE INVENTION

Based upon the present invention, HM-3 and Fc are prepared into a fusion protein to prolong the half-life of HM-3 and improve pharmaceutical activity. It is found in the present invention that the fusion protein shows higher biological activity and stability in vivo and in vitro, and can remarkably inhibit inflammatory reaction; relieve the symptoms of autoimmune diseases, neovascular diseases and osteoarthritis as well as has a long-acting plasma half-life period.

For this purpose, the present invention discloses an HM-3-Fc fusion protein formed by linking an active polypeptide HM-3 to a human IgG-Fc fragment or an IgG-Fc mutant fragment.

The fusion protein of the present invention is prepared by linking HM-3 to a human IgG-Fc fragment or a mutant of the IgG-Fc fragment via a C-terminal or an N-terminal or C-terminal and N-terminal simultaneously, and the ligation may be achieved by a Linker peptide.

The fusion protein of the present invention may be described by the following structures:

(HM-3)$_n$-Linker-IgG-Fc,

IgG-Fc-Linker-(HM-3)$_n$, or (HM-3)$_n$-Linker-IgG-Fc-Linker-(HM-3)$_n$;

wherein n is selected from 1, 2, 3, 4 or 5,
wherein Linker represents a linker peptide, and the linker peptide is selected from:

① (GGGGS)$_a$, where a is 1, 2, 3, 4, 5 or 6 (SEQ ID NO: 21);
② A (EAAAK)$_b$ A, where b is 1, 2, 3, 4, 5 or 6 (SEQ ID NO: 22);
③ (AP)$_c$, where c is 1 to 18 (SEQ ID NO: 23);
④ G$_d$, where d is 1 to 15 (SEQ ID NO: 24); and wherein, preferably, the Linker peptide is the sequence of (GGGGS)$_a$, and the repeat number a is preferably 3, 4 or 5 (SEQ ID NO: 25).

The IgG-Fc is a human Fc fragment of IgG1, IgG2, IgG3 or IgG4 or its mutant fragment; preferably, is Fc of IgG2 or IgG4 or its mutant, and most preferably it is a mutant mIgG4-Fc.

The fusion protein of the present invention is preferably selected from proteins consisting of the following sequences:

```
TSL-1:
                                    (SEQ ID NO: 9)
HM-3-(GGGGS)₃-IgG2-Fc;

TSL-2:
                                    (SEQ ID NO: 10)
HM-3-(GGGGS)₃-mIgG4-Fc;
```

```
-continued
TSL-3:
                                    (SEQ ID NO: 11)
IgG2-Fc-(GGGGS)₃-HM-3;

TSL-4:
                                    (SEQ ID NO: 12)
mIgG4-Fc-(GGGGS)₃-HM-3;

TSL-5:
                                    (SEQ ID NO: 13)
HM-3-(GGGGS)₃-IgG4-Fc;

TSL-6:
                                    (SEQ ID NO: 14)
IgG4-Fc-(GGGGS)₃-HM-3;

TSL-13:
                                    (SEQ ID NO: 15)
H14-3-(GGGGS)₃-mIgG4-Fc-(GGGGS)₃-HM-3;

TSL-14:
                                    (SEQ ID NO: 16)
HM-3-HyFc;

TSL-15:
                                    (SEQ ID NO: 17)
mIgG4-Fc-G5-HM-3-G8-HM-3;

TSL-16:
                                    (SEQ ID NO: 18)
HyFc-(GGGGS)₃-HM-3;

TSL-17:
                                    (SEQ ID NO: 19)
mIgG4-Fc-A(EAAAK)₄A-HM-3;
and TSL-18:
                                    (SEQ ID NO: 20)
mIgG4-Fc-(AP)₉-HM-3;
```

The fusion protein of the present invention may be prepared by synthesis, and the synthesis is to link HM-3 polypeptide to a Linker via a covalent bond, and then to link another end of the Linker with IgG-Fc.

The fusion protein may also be obtained by gene recombination, such as it is expressed by yeast, CHO, SP2/0, BHK and/or HEK 293 cells; preferably, it is expressed by CHO cells and/or HEK 293 cells.

The fusion protein of the present invention may increase the action time of drugs in vivo, thus prolonging the half-life, and improving adaptability and compliance of patients.

The present invention further provides a pharmaceutical composition containing the fusion protein of the present invention, which exists in a suitable dosage form; the dosage form is selected from the group consisting of injections, capsules, tablets, pills, nasal sprays, or aerosols; and the mode of administration includes oral administration, intravenous injection, intravenous drip, subcutaneous or intramuscular injection.

The present invention further provides an application of the fusion protein of the present invention in the preparation of drugs for the treatment of autoimmune disease. Preferably, the autoimmune disease is rheumatoid arthritis and has pharmacokinetic characteristics.

The invention further provides an application of the fusion protein of the present invention in the preparation of drugs for the treatment of neovascular diseases. Preferably, the neovascular diseases are wet age-related macular degeneration and tumor metastasis.

The fusion protein of the present invention may serve as an ophthalmic drug, and it has pharmacokinetic characteristics in eyes, especially in aqueous humor and vitreous body.

The present invention further provides an application of the fusion protein of the present invention in the preparation of drugs for the treatment of osteoarthritis.

The fusion protein of the present invention may play a protective role on chondrocytes to prevent and treat osteoarthritis via pathological alteration of chondrocytes, and meanwhile, the fusion protein has a pharmacokinetic characteristic.

A DNA molecule encoding the fusion protein is firstly synthesized when the fusion protein of the present invention is prepared by gene recombination, and nucleotide sequence of the DNA is preferably the sequence of Sequence Listing 1.

In the present invention, when gene recombination is used for preparation, the synthesized DNA molecule is prepared into a recombinant expression vector through a plasmid, preferably a mammalian cell expression vector, e.g., pcDNA3.4 (INVITROGEN).

The present invention is further to transfect the expression vector into a host cell, preferably a mammalian expression cell, more preferably a HEK 293 cell, a CHO cell. The host cells are expressed and cultured to separate the fusion protein of the present invention from a cell culture fluid, and the fusion protein is purified and separated to obtain the fusion protein of the present invention. Therefore, the present invention further provides a purification process of the fusion protein of the present invention, preferably, it is purified by Protein A or Protein G affinity chromatography.

DETAILED DESCRIPTION OF THE INVENTION

Figure 1:
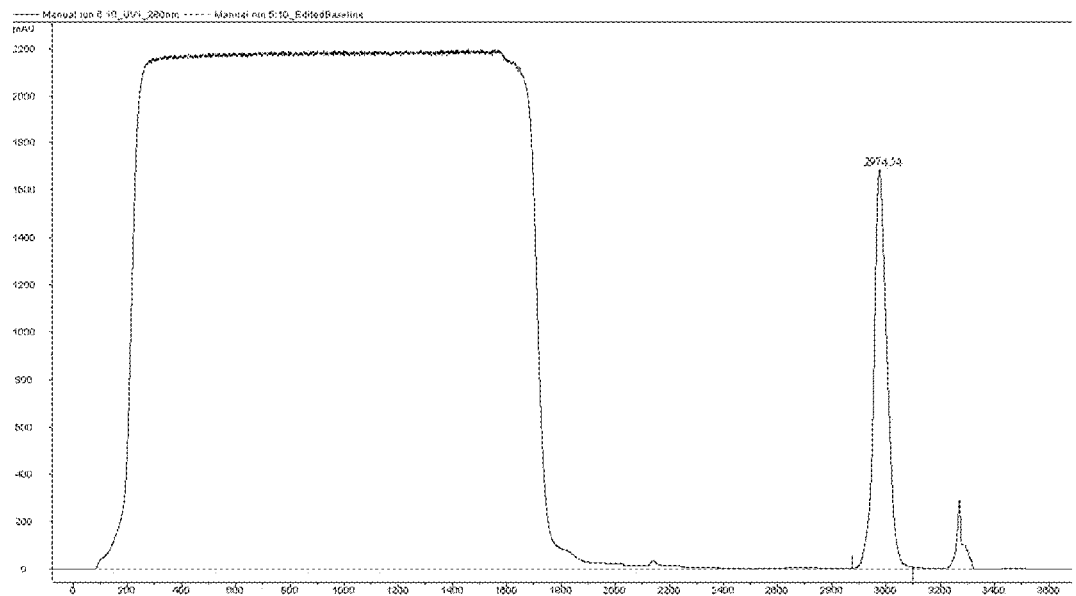
FIG. 1 shows affinity capture map of a TSL-4 protein.

The present invention is further described by the following embodiments.

Embodiment 1 Molecular Design of HM-3 Fusion Protein

HM-3-Fc fusion protein consists of three parts, including an active part HM-3 polypeptide, a linker and a human IgG-Fc fragment or IgG-Fc mutant fragment; the specific design method includes the following steps:

1. Selection of an Fc Fragment

Due to the difference of heavy chains, the human IgG antibody is divided into four subtypes, namely IgG1, IgG2, IgG3 and IgG4. The existing research results have shown that the four subtypes have different plasma half-life, cytotoxicity and other characteristics (as shown in Table 1) and are directly related to the Fc fragment. IgG3 has the shortest half-life in vivo, and its Fc fragment is not too suitable as a molecular chaperone to prolong the in vivo half-life of a target protein, so IgG3 is firstly excluded by the test. Affinity of the Fc fragment to complements and Fc receptors determines the capacity of antibody-dependent cellular cytotoxicity (ADCC effect) and complement-dependent cytotoxicity (CDC effect). IgG1 and IgG3 have the strongest ADCC and CDC effects, and it is determined by tests that IgG1 and IgG3 are not suitable to be constructed as a fusion protein with healthy cells as target spots. Therefore, Fc fragments of IgG1 and IgG3 were excluded after being screened.

Based on the fact that the developed indication is an autoimmune disease, the target is a normal somatic cell, the need to inhibit the signaling pathway only and to prolong in vivo half-life as far as possible, it requires a fragment with low or no ADCC effect and CDC effect, and accordingly, the Fc fragment of IgG2 or IgG4 is more suitably selected for the Fc fragment of the HM-3 fusion protein. To further improve characteristics of the natural Fc fragment, Fc fragment mutants of IgG2 and IgG4 are also extensively considered within the screening range of the present invention.

TABLE 1

Comparison of properties of four IgG subtypes

| Property | IgG1 | IgG2 | IgG3 | IgG4 |
|---|---|---|---|---|
| Heavy chain and molecular weight (kDa) | γ1 (52) | γ2 (52) | γ3 (58) | γ4 (52) |
| Monomer molecular weight (kD) | 146 | 146 | 170 | 146 |
| Number of amino acids in hinge region | 15 | 12 | 62 | 12 |
| Half-life in blood plasma (day) | 21~23 | 21~23 | 7~8 | 21~23 |
| Complement fixing | ++ | + | +++ | − |
| Binding to FcR: FcγRI | +++ | − | +++ | + |
| FcγRH | +++ | + | +++ | + |
| FcγRHI | ++ | − | ++ | − |
| Binding to SPA | + | + | + | − |
| Passing through placenta | ++ | + | ++ | ++ |

2. Selection of Linker

Linker is a polypeptide chain to link functional and chaperone proteins; the Linker's sequence and length are crucial to the functions of fusion protein. The choice of Linker needs to consider the following aspects:

1) The length should be moderate, too short to guarantee the relative independence between proteins in the space. Too long may increase the risk of Linker rupture and cause immunogenicity; 2) Linker's sequence cannot contain protein enzyme cutting sites so as to avoid being cut off; 3) Linker may be a natural or artificial Linker; 4) Linker may be divided into a rigid Linker and a flexible Linker.

Through a large number of experiments, four artificially-designed Linkers were selected as verification alternatives in the present invention:

a. $(GGGGS)_n$, is the most widely used flexible Linker, where a may be 1, 2, 3, 4, 5, or 6 (SEQ ID NO: 21);
b. A $(EAAAK)_b A$, is an α-spiral rigid Linker, where b may be 1, 2, 3, 4, 5 or 6 (SEQ ID NO: 22);
c. $(AP)_c$, is a linear rigid Linker, where c may be 1 to 18 (SEQ ID NO: 23);
d. $G_d$ (SEQ ID NO: 24), is a flexible Linker analogous to $(GGGGS)_n$ (SEQ ID NO: 28), where d may be from 1 to 15.

3. Fusion Sequence of HM-3 and Fc Fragment

Due to the unique direction of amino acid sequence, there are two modes of linking the fusion of two proteins, and N-terminal ligation is to the attachment of a functional protein to the N-terminal of the Fc fragment, and C-terminal ligation is to the attachment of a functional protein to a C-terminal of the Fc fragment.

4. Structure Design for Alternative Fusion Proteins

Combined with the factors for the design of the fusion protein, at least more than 300 fusion protein structures may be generated, so it is impractical to express the structures and verify their efficacy one by one. Therefore, from the angle of single factor comparison, the most common (GGGGS) 3 Linker (SEQ ID NO: 26) is preferred, and the following six molecules were designed:

```
TSL-1:
                                           (SEQ ID NO: 9)
HM-3-(GGGGS)3-IgG2-Fc;

TSL-2:
                                           (SEQ ID NO: 10)
HM-3-(GGGGS)3-mIgG4-Fc;

TSL-3:
                                           (SEQ ID NO: 11)
IgG2-Fc-(GGGGS)3-HM-3;

TSL-4:
                                           (SEQ ID NO: 12)
mIgG4-Fc-(GGGGS)3-HM-3;

TSL-5:
                                           (SEQ ID NO: 13)
HM-3-(GGGGS)3-IgG4-Fc;

TSL-6:
                                           (SEQ ID NO: 14)
IgG4-Fc-(GGGGS)3-HM-3;
``` and

Afterwards, on the basis of the six structures mentioned above, 6 new fusion protein structures were formed by replacing a single factor and introducing multiple design ideas, such as HyFc, rigid Linker and overlapping peptide:

```
TSL-13:
                                           (SEQ ID NO: 15)
HM-3-(GGGGS)3-mIgG4-Fc-(GGGGS)3-HM-3;

TSL-14:
                                           (SEQ ID NO: 16)
HM-3-HyFc;

TSL-15:
                                           (SEQ ID NO: 17)
mIgG4-Fc-G5-HM-3-G8-HM-3;

TSL-16:
                                           (SEQ ID NO: 18)
HyFc-(GGGGS)3-HM-3;

TSL-17:
                                           (SEQ ID NO: 19)
mIgG4-Fc-A(EAAAK)4A-HM-3;
and TSL-18:
                                           (SEQ ID NO: 20)
mIgG4-Fc-(AP)9-HM-3;
```

The amino acid sequences above are shown in the Sequence Listing.

The above 12 fusion proteins are the most representative candidate protein structures and the cell expression and in vitro pharmacodynamic experiment were performed simultaneously and the results of in vitro pharmacodynamic experiment were obtained.

Through different modes of comparison, each structure variable can be compared with each other to screen out an optimal fusion protein structure. The possibility of drug-gability was evaluated by in vivo pharmacodynamics, pharmacokinetics, toxicology and the like, thus further developing an innovative drug for the treatment of autoimmune diseases, e.g., rheumatoid arthritis.

Embodiment 2: Vector Construction

Based upon the same design approach and the application of the same expression vector, the 12 fusion proteins had completely consistent construction process of the transient-transfection expression vector; mIgG4-Fc-(GGGGS)$_3$-HM3 (TSL-4) was taken as an example to introduce the construction process of the expression vector.

TSL-4 fusion protein was obtained by linking an mIgG4-Fc fragment to a HM-3 molecule, and (GGGGS)$_a$ served as a Linker, where a was 3 (SEQ ID NO: 26).

Amino acid sequences constituting each portion of TSL-4 were spliced with each other in accordance with the order of mIgG4-Fc-(GGGGS)$_3$-HM3, and the sequence was shown in Sequence Listing 12.

The DNA sequence corresponding to the mIgG4-Fc-(GGGGS)$_3$-HM3 fusion protein was shown in Sequence Listing 1.

In order to adapt to the secretory expression of eukaryotic cells, such as CHO or HEK 293, the necessary Kozak sequence and signal peptide were added to obtain a complete mIgG4-Fc-(GGGGS)$_3$-HM3 expression sequence, and the DNA sequence was shown in Sequence Listing 2.

A Biotechnology Company was entrusted to completely synthesize the above DNA sequence, and then DNA sequence was ligated with the commercial expression vector pcDNA 3.4-TOPO from Invitrogen Corporation via subcloning, thus obtaining an expression vector pcDNA3.4-mIgG4-Fc-(GGGGS)$_3$-HM3. The expression vector was preserved in an E. coli DH5α glycerol tube and sent to the laboratory for storage at −80° C.

Embodiment 3: Long-Term Preservation of Bacterial Strain of the Expression Vector Under sterile conditions, the E. coli DH5α glycerol tube containing pcDNA3.4-mIgG4-Fc-(GGGGS)$_3$-HM3 was thawed and inoculated into a 250 ml shake flask containing 50 ml of 100 ug/ml Amp-resistant LB medium according to 1% inoculum size, and then vibrated at 160 rpm for culture overnight at 37° C.

Afterwards, 25 ml of sterile 60% glycerol was added to the bacteria solution under sterile conditions, after mixed fully and evenly, the bacteria solution was dispensed into 1.5 ml sterile centrifuge tubes at a concentration of 1 ml/pcs. to complete the preparation of the glycerol tube, and finally, the glycerol tube was preserved for a long time at −80° C.

Embodiment 4 Preparation of the Expression Vector

All vectors for cell transfection must be sterile and endotoxin-controlled, so the plasmid extraction of all expression vectors was performed by Genopure plasmid Maxi Kit from Roche, and plasmids were sterilized.

(1) A glycerol tube was taken out at −80° C. one day morning before plasmid extraction, and the bacteria solution was inoculated into a test tube containing 5 ml of 100 ug/ml Amp-resistant LB medium according to 1% inoculum size under aseptic conditions for shaking culture for 6-8 h at 37° C. and 160 rpm.

(2) Under sterile conditions, the bacteria solution in the tube were totally inoculated into a 2 L shake flask containing 500 ml of 100 ug/ml Amp-resistant LB medium, and then vibrated at 160 rpm for culture overnight at 37° C.

(3) Plasmid extraction was performed by the Genopure plasmid Maxi Kit from Roche. The method was as follows:

a. 3000-5000 g were centrifuged for 5-10 min to collect 500 ml of *E. coli* bacteria at 4° C. 24 ml of Suspension Buffer (containing RNase) was added to fully resuspend the bacteria.

b. 24 ml of Lysis Buffer was added, inverted and mixed for 6-8 times fully, standing for 2-3 min at room temperature.

c. 24 ml of Neutralization Buffer was added, immediately inverted and mixed for 6-8 times fully till flocculent precipitate appeared.

d. lysate was purified. 12000 g Lysate were centrifuged for 45 min above at 4° C., and then supernatant was carefully transferred to an adsorption column.

e. A paper ring in the kit was attached to the adsorption column and placed at the neck of a conical flask, and 6 ml of Equilibration Buffer was dropwisely added on the adsorbing material.

f. The clean lysate obtained in step e was added to the adsorption column for naturally flowing through by gravity. The liquid flowing through the column was discarded.

g. 12 ml of Wash Buffer was added to the adsorption column for naturally flowing through by gravity, then the liquid flowing through the column was discarded. The operation above was repeated for twice.

h. On a super clean bench, the adsorption column was placed onto a 50 ml of sterile, high-speed, endotoxin-free and round-bottomed centrifuge tube, then 14 ml of Elution Buffer pre-heated at 50° C. was added to the adsorption column for flowing through by gravity.

i. Plasmid DNA was precipitated by adding 20 ml of isopropanol, 15000 g were centrifuged at 4° C. for 30 min, and the supernatant was carefully discarded on the super clean bench. (Pay more attention to the step. Sometimes the plasmid formed viscous liquid at the bottom of the centrifuge tube instead of solid precipitate, therefore, a transfer pipette was used to remove most of the liquid from the upper layer, and then the remaining supernatant was carefully transferred into a sterile and conical centrifuge tube, such as a 15 ml centrifuge tube or a 50 ml centrifuge tube. Please try not to absorb the viscous liquid containing the plasmid as little as possible. Subsequently, the conical centrifuge tube was observed, and then the viscous liquid containing the plasmid absorbed carelessly at the bottom was absorbed back into the round-bottomed centrifuge tube.)

j. 4 ml of pre-cooled 75% ethanol was used, and the lid of the centrifuge tube was tightened, and then the tube was rotated to allow the 75% ethanol to wet the interior of the entire centrifuge tube. On the one hand, the plasmid possibly remaining on the tube wall was washed, and on the other hand, the entire inner wall of the centrifuge tube was sterilized. More than 15000 g were centrifuged at 4° C. for 10 min. The operation above was repeated for once.

k. 75% ethanol was discarded on a super clean bench, the residual liquid was carefully pipetted off by a 10 ul pipettor, and then the centrifuge tube was inverted on an absorbent paper and dried for about 20 min.

l. On a super clean bench, the solid plasmid was completely soaked by 200-400 ul of sterile ddH2O, and the centrifuge tube was tilted for standing overnight at 4° C. after tightening the lid thereof, thus fully dissolving the plasmid. The plasmid was transferred to a 1.5 ml of sterile centrifuge tube and 2 ul was taken for concentration detection on the super clean bench. According to the detection results, the plasmid concentration was adjusted to 1 ug/ul by sterile ddH2O (double distilled water), and the plasmid was sterilized by a 0.22 µm sterile filter membrane, and then, 5 ul of plasmids were taken and inoculated into a test tube containing 5 ml of non-resistant LB culture medium for shaking culture overnight at 37° C., finally, sterility was confirmed. The preparation of the sterile plasmid was complete at this time. Plasmid DNA was preserved at 4° C. or −20° C.

Thus, the preparation of the expression vector was completed.

Embodiment 5 Quick Expression of the Fusion Protein

Expi293 Expression System from ThermoFisher is a commercial quick kit for protein preparation based on the transient transfection of 293F cell (a kind of screened HEK293 cell), used for the quick acquisition of fusion protein. The preparation for the 12 fusion proteins shall follow the experimental scheme below.

1. According to the operation instructions of Expi 293 Expression System, the final volume of each bottle of cells is 800 ml when a 2 L shake flask was used for the experiment.

2. Transfected Expi293F cells were passaged at least for three times from recovery. The culture scale might be sequentially enlarged according to experimental requirements in subculture process.

3. One day before transient transfection, cells were inoculated into a total volume of 1200 ml Expi293 Expression Medium according to the living cell density of $2 \times 10^6$ for shaking culture under the conditions of 37° C., 8% $CO_2$ (carbon dioxide?) and 125 rpm.

4. On the day of transient transfection, the cells cultured the previous day were counted, and the cell density should be $3-5 \times 10^6$ cells/ml and its motility rate should be greater than 95%. The cell density was adjusted to $3 \times 10^6$ cells/ml and the cell volume in each 2 L shake flask was adjusted to 680 ml.

5. 800 ug plasmid DNA was re-constituted in 40 ml of Opti-MEM I Reduced Serum Medium and mixed gently.

6. 2.16 mL of ExpiFectamine 293 Reagent was added to Opti-MEM I Reduced Serum Medium to a constant volume of 40 ml. It was mixed gently and incubated at room temperature for 5 min (transformation efficiency may be affected by long incubation).

7. The above two kinds of solution were mixed gently and incubated at room temperature for 20-30 min. The preparation of the plasmid-transfection reagent mixed liquor was completed.

8. 80 ml of the plasmid-transfection reagent mixture was added to the culture medium of step 4 to obtain a total volume of 760 ml.

9. Shaking culture was performed for 18 h at 37° C., 8% $CO_2$ and 125 rpm.

10. 4 mL of ExpiFectamine 293 Transfection Enhancer 1 and 40 ml of ExpiFectamine 293 Transfection Enhancer 2 were added. The total volume was 804 ml at this timepoint.

11. Shaking culture was performed at 37° C., 8% $CO_2$ and 125 rpm.

12. Sampling was performed to detect the yield by an immunoturbidimeter at the end of fermentation 6 days later after transfection, and protein purification was conducted.

Embodiment 6 Purification of the Fusion Protein

Since the above 12 kinds of fusion proteins were essentially Fc fusion proteins, and they were captured by a Protein A affinity column. In actual purification, it was found that the purification parameters were completely identical. Therefore, the purification of a certain batch of TSL-4 protein was taken as an example to describe the purification process of the fusion protein.

1. Sample pretreatment: 1.60 L of fermentation liquor of batch 20160308 was centrifuged by a Beckman J×25 centrifugal machine and a 500 ml centrifuge cup under the conditions of 7500 imp, 20 min, 4° C., and about 1.46 L of the obtained supernatant was further used for the next step, namely, protein A capture.

2. Affinity capture of the target protein:
Information of the chromatographic column

| Filler | Mabselect SuRe |
|---|---|
| Chromatographic column | XK50/20 |
| Column height (cm) | 10 |
| Cross sectional area of the chromatographic column (cm$^2$) | 19.62 |
| Filler volume (mL) | 196.2 |

Method information was as follows:

1) firstly, 500 ml of 0.2 M NaOH was used to sterilize at a flow rate of 10 ml/min;

2) the chromatographic column was equilibrated by a buffer solution of 20 mM PB, 0.15 M NaCl, pH 7.0, where the volume was about 1000 ml and flow rate was 20 ml/min;

3) sample loading: pH of the sample was pre-adjusted to be neutral, and the flow rate was 20 ml/min;

4) the chromatographic column was washed by a buffer solution of 20 mM PB, 0.15 M NaCl, pH 7.0, where the volume was about 800 ml and the flow rate was 20 ml/min;

5) target protein was eluted by a buffer solution of 50 mM citric acid-sodium citrate, 0.15 M NaCl, pH 3.0, it begun to collect the target protein at a peak of 20 mAu, and stopped collecting at 20 mAu after the peak; the flow rate was 20 ml/min;

6) finally, the chromatographic column was washed by 500 ml of 0.2 M NaOH solution, and rinsed to be neutral with dd$H_2O$ water, and then preserved by 20% ethanol;

The samples were combined in a volume of about 138 ml, and the mixed solution was adjusted within a range of pH 4.12 to 7.0 with 1N NaOH 20 ml, and the eluate turned from slightly cloudy to clear. Measured results were shown in FIG. 1.

3. Further separation and purification with gel chromatography
Column parameters:

| Filler | Superdex200 |
|---|---|
| Chromatographic column | XK50/60 |
| Column height (cm) | 58 |
| Cross sectional area of the chromatographic column (cm$_2$) | 19.62 |
| Filler volume (mL) | 1138 |
| Flow rate | ml/min |
| Sample loading | 1-10% loading quantity of sample |

Method information:

1) the chromatographic column was sterilized with 0.5M NaOH 300 ml at a flow rate of 10 ml/min, and then washed by ultrapure water to be about neutral;

2) the chromatographic column was equilibrated by a PBS buffer solution, pH 7.4, and the equilibrium volume was about 1500 ml and the flow rate was 10 ml/min;

3) sample loading was performed, and the sample was protein A eluent, and the loading quantity of sample was 40 ml;

4) the sample was collected, where peak 3 was a target protein peak and was collected; it began to collect the protein at the peak of 10 mAU and stop collecting 10 mAu later after the peak;

5) finally, the chromatographic column was preserved with 0.1 M NaOH at a flow rate of 10 ml/min.

Figure 2:
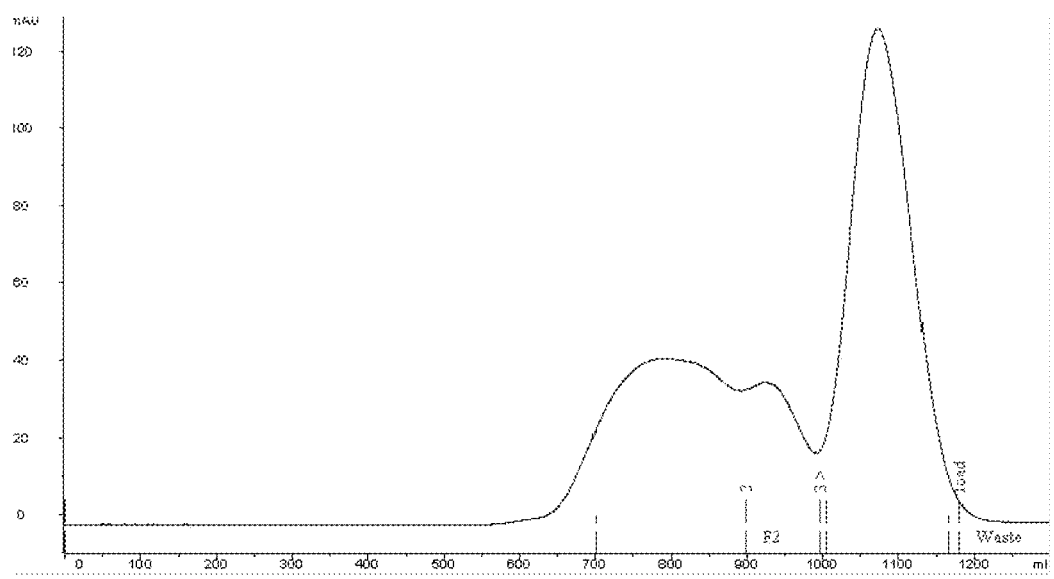
FIG. 2 shows further separation and purification of the TSL-4 protein.

Measured results were shown in FIG. 2.

4. Sample ultrafiltration concentration: samples at peak 3 were combined, ultrafiltrated and concentrated, where 10 kDa served as an ultrafiltration membrane; samples were concentrated till the concentration of the target protein was more than 5 mg/ml, and dispensed, then preserved in a −80° C. refrigerator. At the beginning of combination, the volume of the sample in this batch was about 550 ml and the concentration was about 0.29 mg/ml; finally it was concentrated to 27 ml and the final concentration was about 5.53 mg/ml; the sample was dispensed and frozen.

5. Purity of the final sample

Figure 3:
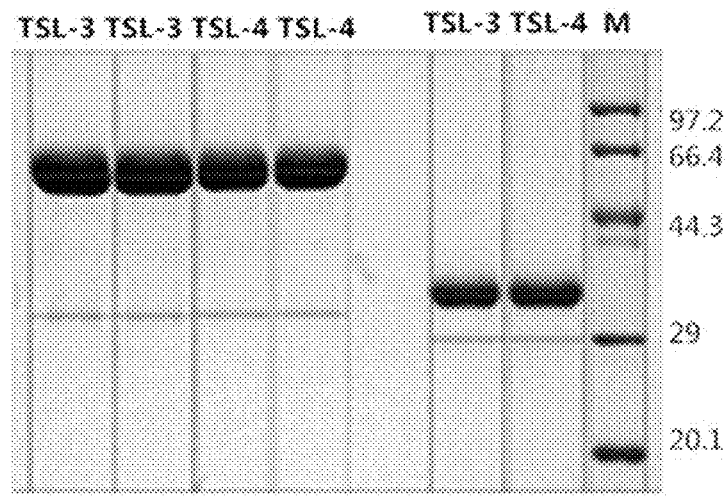
FIG. 3 shows electrophoretogram with a batch 20160308.
Figure 4:
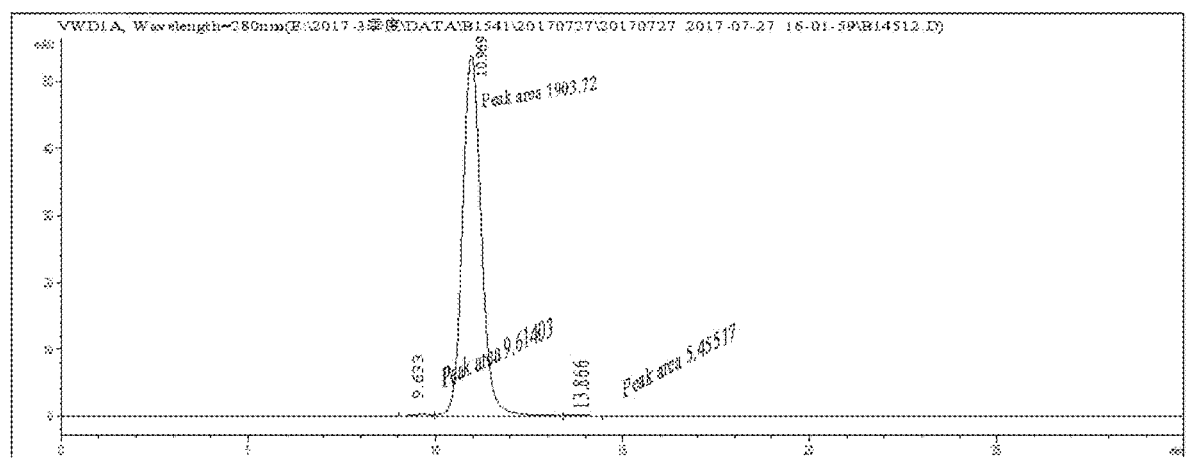
FIG. 4 shows HPLC-SEC with a batch 20160308.

As shown in FIG. 3, the electrophoresis purity of batch 20160308 was about 96.9%; as shown in FIG. 4, the HPLC-SEC purity of batch 20160308 was about 99.3%.

Same purification process was followed to successfully express and prepare into 12 kinds of fusion proteins:

TSL-1 fusion protein: HM-3-(GGGGS)$_3$—IgG2-Fc;
TSL-2 fusion protein: HM-3-(GGGGS)$_3$-mIgG4-Fc;
TSL-3 fusion protein: IgG2-Fc-(GGGGS)$_3$-HM-3;
TSL-4 fusion protein: mIgG4-Fc-(GGGGS)$_3$-HM-3.
TSL-5 fusion protein: HM-3-(GGGGS)$_3$-IgG4-Fc
TSL-6 fusion protein: IgG4-Fc-(GGGGS)$_3$-HM-3
TSL-13 fusion protein: HM-3-(GGGGS)$_3$-mIgG4-Fc-(GGGGS)$_3$-HM-3
TSL-14 fusion protein: HM3-HyFc
TSL-15 fusion protein: mIgG4-Fc-G$_5$-HM-3-G$_8$-HM-3
TSL-16 fusion protein: HyFc-(GGGGS)$_3$-HM-3
TSL-17 fusion protein: mIgG4-Fc-A(EAAAK)$_4$ A-HM-3
TSL-18 fusion protein: mIgG4-Fc-(AP)$_9$—HM-3

Figure 5:
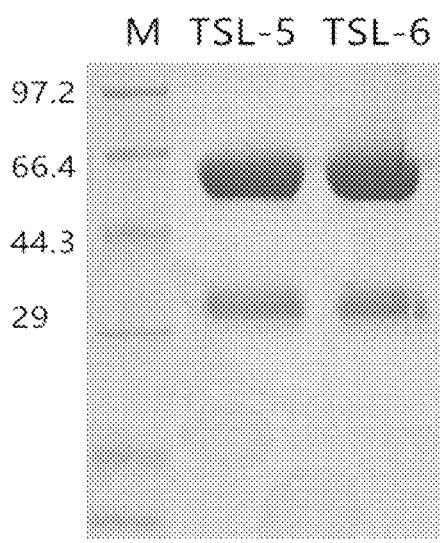
FIG. 5 shows electrophoretogram of TSL-5 and TSL-6 after being purified.
Figure 6A:
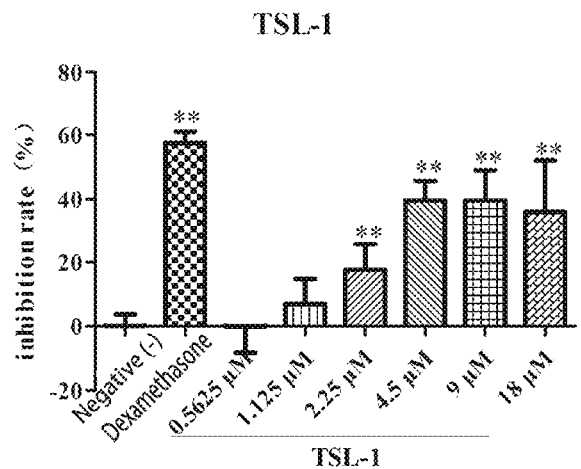
FIG. 6A shows a comparison diagram of the inhibitory effect on splenic lymphocyte proliferation of TSL-1 fusion protein in mice.
Figure 6B:
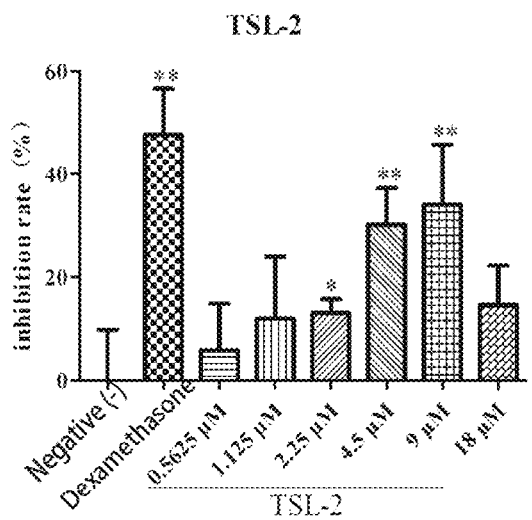
FIG. 6B shows a comparison diagram of the inhibitory effect on splenic lymphocyte proliferation of TSL-2 fusion protein in mice.
Figure 6C:
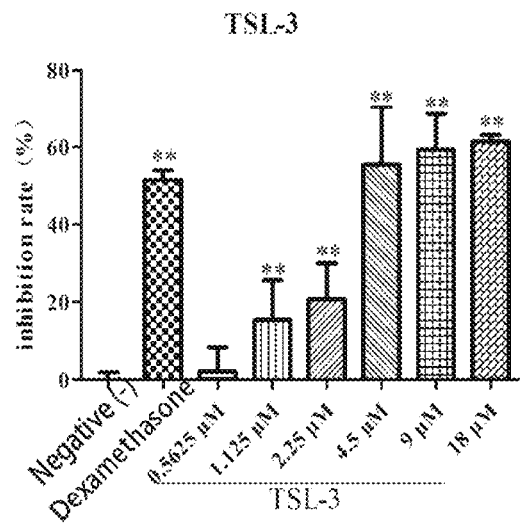
FIG. 6C shows a comparison diagram of the inhibitory effect on splenic lymphocyte proliferation of TSL-3 fusion protein in mice.
Figure 6D:
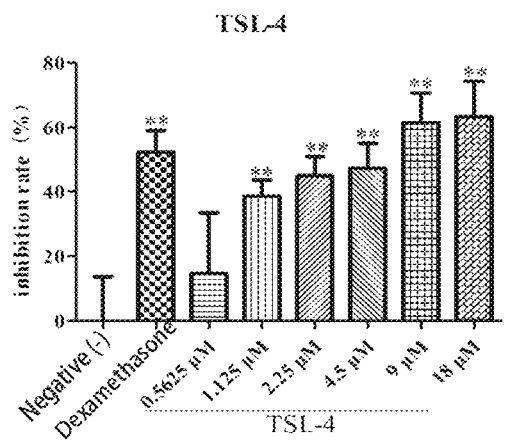
FIG. 6D shows a comparison diagram of the inhibitory effect on splenic lymphocyte proliferation of TSL-4 fusion protein in mice.
Figure 6E:
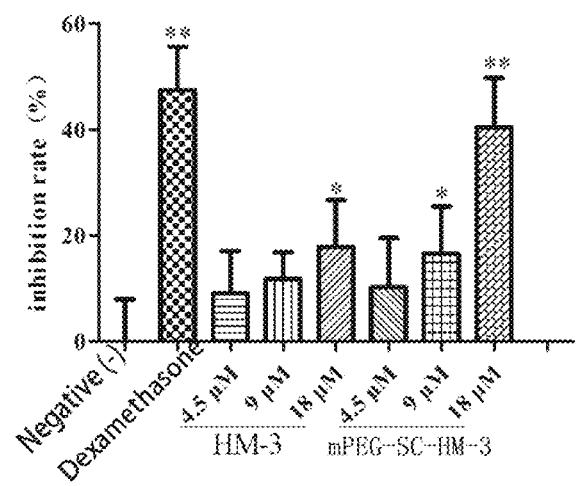
FIG. 6E shows a comparison diagram of the inhibitory effect on splenic lymphocyte proliferation of HM-3 and mPEG-SC-HM-3 in mice.
Figure 7A:
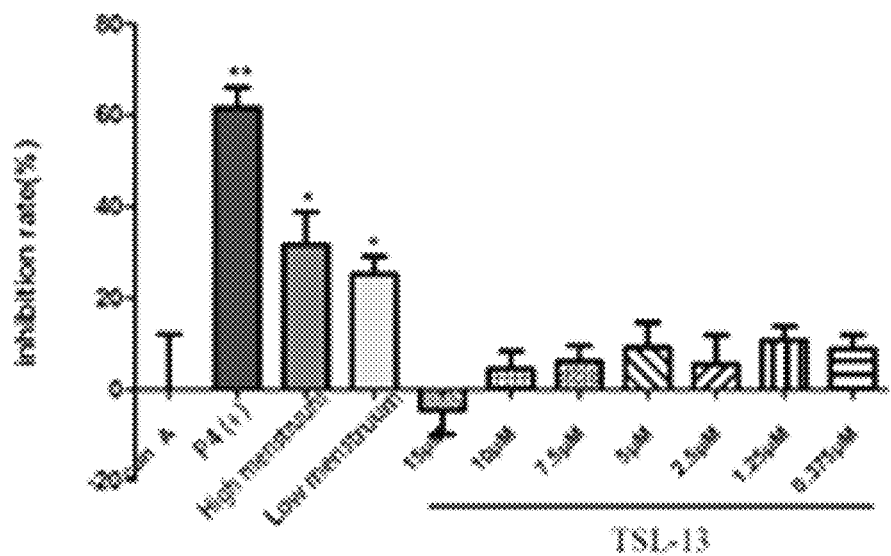
FIG. 7A shows a comparison diagram of the inhibitory effect on splenic lymphocyte proliferation of TSL-13 fusion protein in mice.
Figure 7B:
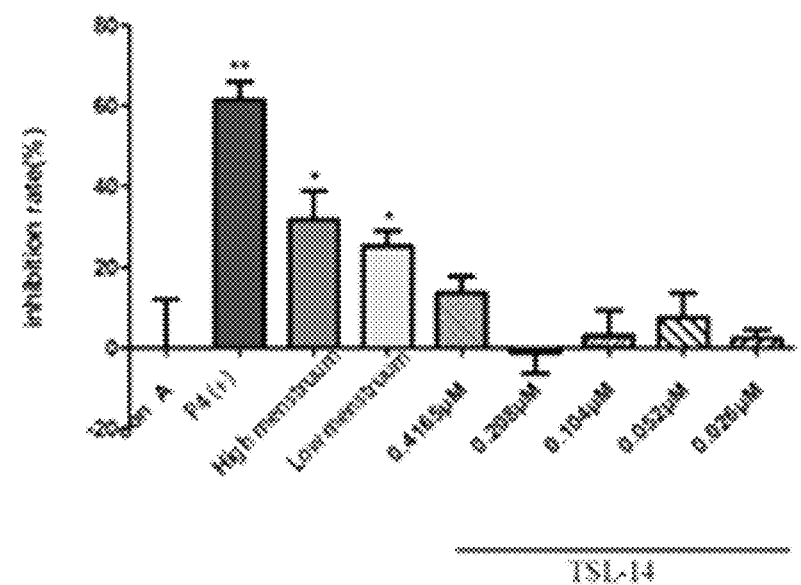
FIG. 7B shows a comparison diagram of the inhibitory effect on splenic lymphocyte proliferation of TSL-14 fusion protein in mice.
Figure 7C:
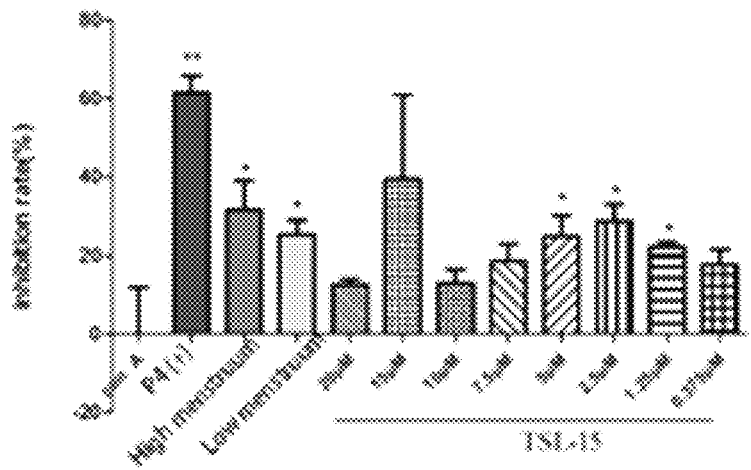
FIG. 7C shows a comparison diagram of the inhibitory effect on splenic lymphocyte proliferation of TSL-15 fusion protein in mice.
Figure 7D:
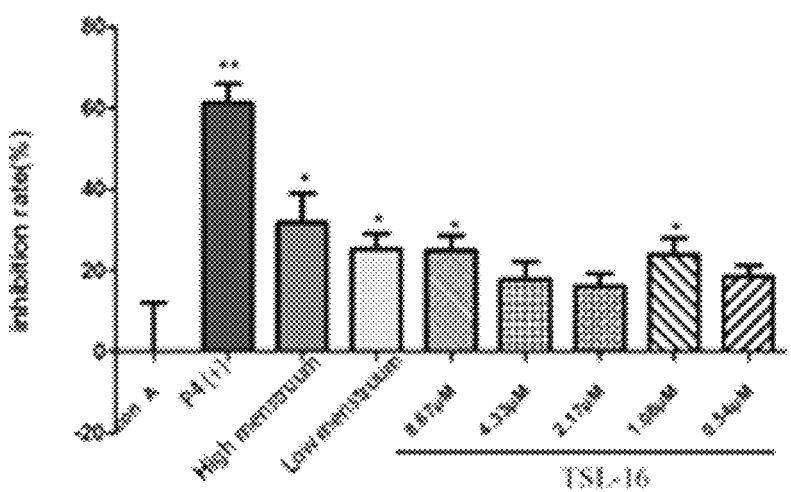
FIG. 7D shows a comparison diagram of the inhibitory effect on splenic lymphocyte proliferation of TSL-16 fusion protein in mice.
Figure 7E:
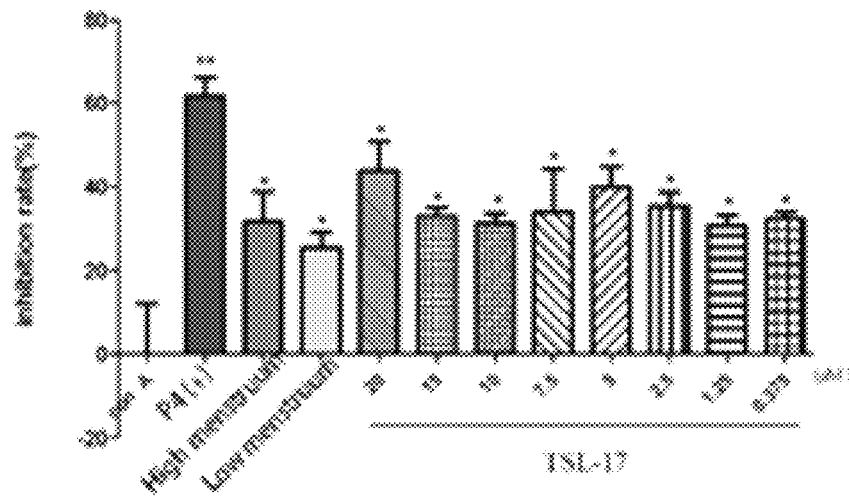
FIG. 7E shows a comparison diagram of the inhibitory effect on splenic lymphocyte proliferation of TSL-17 fusion protein in mice.
Figure 7F:
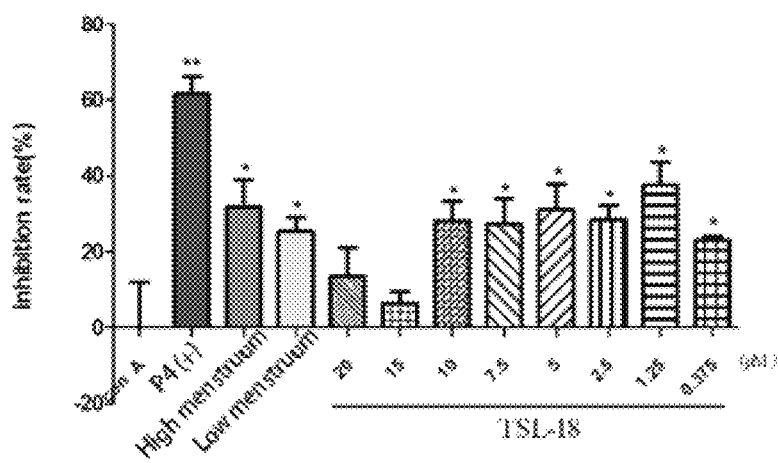
FIG. 7F shows a comparison diagram of the inhibitory effect on splenic lymphocyte proliferation of TSL-18 fusion protein in mice.
Figure 8A:
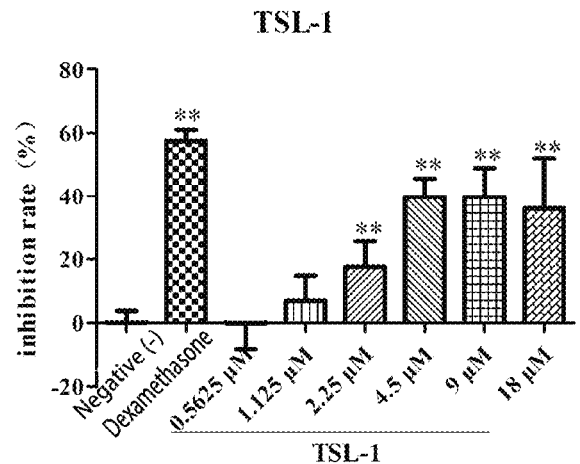
FIG. 8A shows a comparison diagram of the inhibitory effect on splenic lymphocyte proliferation of TSL-1 fusion protein in mice.
Figure 8B:
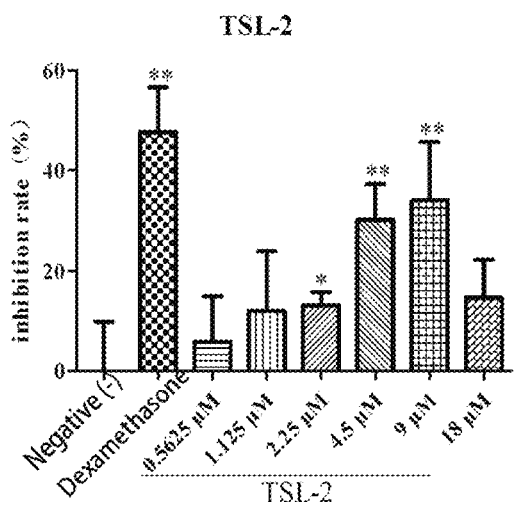
FIG. 8B shows a comparison diagram of the inhibitory effect on splenic lymphocyte proliferation of TSL-2 fusion protein in mice.
Figure 8C:
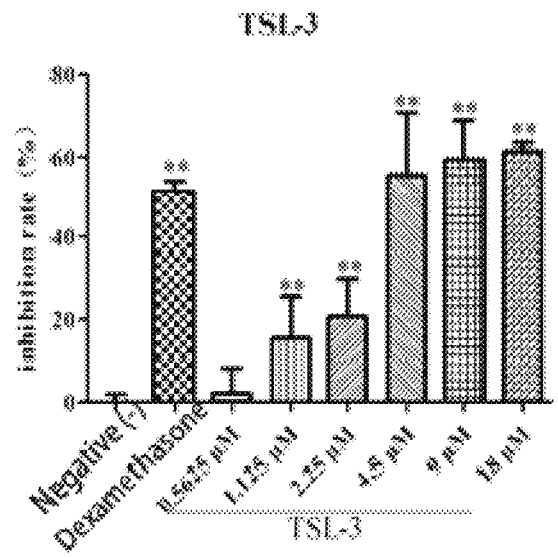
FIG. 8C shows a comparison diagram of the inhibitory effect on splenic lymphocyte proliferation of TSL-3 fusion protein in mice.
Figure 8D:
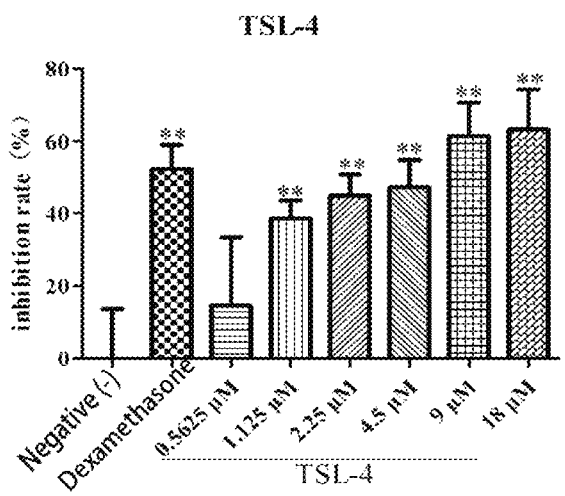
FIG. 8D shows a comparison diagram of the inhibitory effect on splenic lymphocyte proliferation of TSL-4 fusion protein in mice.
Figure 8E:
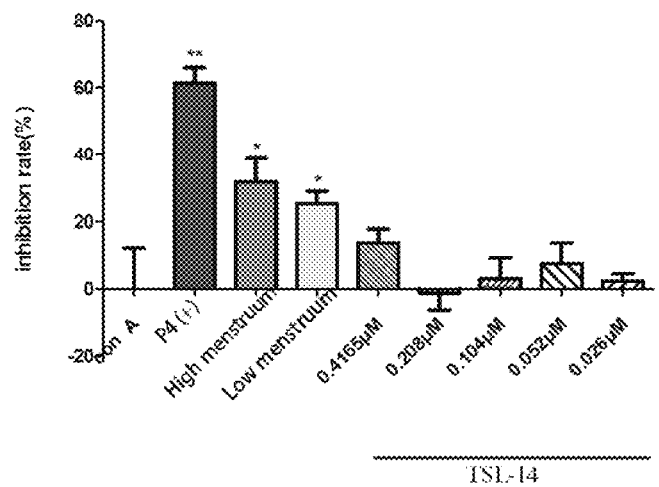
FIG. 8E shows a comparison diagram of the inhibitory effect on splenic lymphocyte proliferation of TSL-14 fusion protein in mice.
Figure 8F:
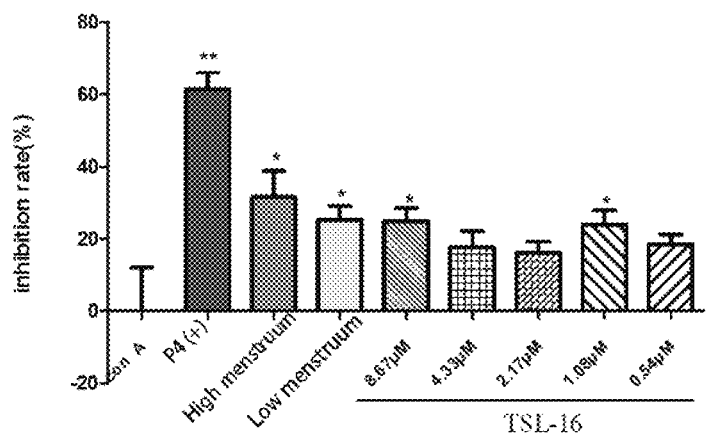
FIG. 8F shows a comparison diagram of the inhibitory effect on splenic lymphocyte proliferation of TSL-16 fusion protein in mice.

During protein preparation, as shown in FIG. 5, it was found that there was a serious problem of dimer degradation to the two fusion proteins of TSL-5 and TSL-6, and most of them existed in a monomeric form, indicating that the fusion protein prepared by IgG4-Fc could not form a dimer stably; therefore, the design scheme of the two fusion proteins of TSL-5 and TSL-6 was eliminated.

Embodiment 7: Test on the Splenic Lymphocyte Proliferation of Fusion Protein Mice Experimental method: mice orbit was by bloodletting to death, and immediately immersed in 75% ethanol for 5-10 min, and then the spleen was removed on a clean bench and placed in PBS. The spleen was placed on a sterile cell strainer (200 mesh) and ground with a syringe nozzle; during grinding process, PBS was added continuously; the slurry was collected and centrifuged (1000 rpm for 5 min), then cells were washed 3 times with Tris-ammonium chloride solution, and washed again with a medium, and then re-suspended in the medium. Finally, trypan blue living cell staining was performed on the cells, and the survival rate was more than 95%. The concentration of viable cells was adjusted to $2 \times 10^6$/mL. 100 of cells was added to each well of a 96-well plate, meanwhile, ConA (concanavalin A to simulate splenocyte proliferation) and drugs were added to each well. Six duplicates were set in each group.

The 96-well plate was incubated for 48 h in a 5% CO2 incubator at 37° C. 5 mg/mL of MTT was added to the 96-well plate, 20 μL for each well, and then it was incubated continuously for 4 h in the incubator. The culture medium in the 96-well plate was discarded and 100 μL DMSO was added to each well and mixed gently. Absorbance was measured by a microplate reader at the wavelength of 570 nm and reference wavelength of 630 nm.

Proliferation inhibition rate (PI) was calculated according to formula:

$$Pi(\%) = 1 - \frac{A_{test}}{A_{control}} \times 100\%$$

wherein, $A_{test}$ is the absorbance of dosing group, and $A_{control}$ is the absorbance of negative control. Test results were expressed as mean±SD, and statistical T test was performed. *P<0.05 indicates significant difference, **P<0.01 indicates extremely significant difference. Based upon the results, the efficacy of the fusion protein against rheumatoid arthritis was screened.

In the first round, TSL-1-4 was tested and the specific dosing scheme was shown in Table 2.

TABLE 2

Dosing scheme

| Group | Blank medium | ConA | Dosage |
|---|---|---|---|
| Blank group | 10 μL | / | Blank culture medium 90 μL |
| Negative group | / | 10 μL, 5 μg/mL | Blank culture medium 90 μL |
| Solvent control | / | 10 μL, 5 μg/mL | solvent with equal volume to sample |
| Positive group | / | 10 μL, 5 μg/mL | Dexamethasone 50 μmol/L (20 μg/mL) 90 μL |
| HM-3 | / | 10 μL, 5 μg/mL | 5, 10, 20 μmol/L, 90 μL |
| mPEG-SC-HM-3 | / | 10 μL, 5 μg/mL | 5, 10, 20 μmol/L, 90 μL |
| HM-3 fusion Protein (TSL-1, TSL-2, TSL-3, TSL-4) | / | 10 μL, 5 μg/mL | 0.625, 1.25, 2.5, 5, 10, 20 μmol/L, 90 μL |

Experimental results: As shown in FIGS. 6A-6E, in order to screen the anti-rheumatoid arthritis activity of HM-3 fusion proteins TSL-1, TSL-2, TSL-3 and TSL-4, the mouse spleen lymphocyte proliferation experiment was used to preliminarily screen the FM-3 fusion proteins TSL-1, TSL-2, TSL-3 and TSL-4; results showed that the optimal inhibition rates of the HM-3, mPEG-SC-HM-3 and HM-3 fusion proteins TSL-1, TSL-2, TSL-3 and TSL-4 were respectively 17.9%18.8%, 40.5%19.3%, 39.6%19.4%, 34.1%111.7%, 61.4%11.6% and 63.3%111.0%. The inhibition rate of the HM-3 fusion proteins TSL-3 and TSL-4 was higher than that of the positive control group, moreover, there was a significant difference compared with the negative control group.

In the second round, TSL-13-18 was tested and the specific dosing scheme was shown in Table 3. In the P4 control group, TSL-4 fusion protein served as a control agent.

TABLE 3

Dosing scheme

| Group | Final concentration of Con A | Dosage |
|---|---|---|
| Con A group | 5 μg/mL | Culture medium 100 μL |
| High solvent | 5 μg/mL | Sodium citrate buffer solution (17 mmol/L, 100 μL) |
| Low solvent | 5 μg/mL | Sodium citrate buffer solution (8.5 mmol/L, 100 μL) |
| P4 positive control group | 5 μg/mL | TSL-4 solution (12 μmol/L, 100 μL) |
| TSL-13 | 5 μg/mL | 0.375, 1.25, 2.5, 5, 7.5, 10, 15 μmol/L, 100 μL |
| TSL-14 | 5 μg/mL | 0.4165, 0.208, 0.104, 0.052, 0.026 μmol/L, 100 μL |
| TSL-15 | 5 μg/mL | 20, 15, 10, 7.5, 5, 2.5, 1.25, 0.375 μmol/L, 100 μL |
| TSL-16 | 5 μg/mL | 8.67, 4.33, 2.17, 1.08, 0.54 μmol/L, 100 μL |
| TSL-17 | 5 μg/mL | 15, 10, 7.5, 5, 2.5, 1.25, 0.375 μmol/L, 100 μL |
| TSL-18 | 5 μg/mL | 20, 15, 10, 7.5, 5, 2.5, 1.25, 0.375 μmol/L, 100 μL |

Experimental Results

FIGS. 7A-7F showed an inhibiting effect of agents in each group of TSL-13-18 on splenocyte proliferation stimulated by ConA. Compared with group ConA, the inhibition ratio of mice splenic lymphocyte proliferation in the P4 positive control group and solvent group enhanced significantly (P<0.05); while in each group of TSL-13-18, the concentration gradient of samples TSL-17 and TSL-18 improved significantly (P<0.05) in the inhibition ratio of mice splenic lymphocyte proliferation relative to group ConA; but its inhibition amplitude was less than the P4 positive control group.

Embodiment 8 Single Factor Comparison of 12 Alternative Fusion Protein Structures First, as already mentioned in Embodiment 6 that during purification, it was found that TSL-5 and TSL-6 fusion proteins were not naturally stable in maintaining the expected normal dimer state, both of the TSL-5 and TSL-6 based on natural human IgG 4-Fc fragments were eliminated, meanwhile, IgG4-Fc was no longer an candidate fusion protein Fc fragment. Based on the results of mice splenic lymphocyte proliferation inhibition experiment, a single structural-factor comparison was performed on the remaining 10 candidate fusion proteins.

1, Comparison on Fc Fragments and Ligation Direction

GGGGS*3 Linker (SEQ ID NO: 26) was selected as a unified Linker, and there were 3 kinds of candidate Fc fragments, namely, IgG2-Fc, mIgG4-Fc and HyFc after excluding the natural human IgG 4-Fc. 6 candidate fusion proteins were formed in combination with two linking directions, namely TSL-1, 2, 3, 4, 14 and 16 respectively; and the optimal inhibition rate of each sample was shown in Table 4.

TABLE 4

Comparison on the best inhibition rate of splenic lymphocyte proliferation experiments in three Fc fragments/two linking-directed fusion protein mice

| Fc fragment | | linking direction | | |
|---|---|---|---|---|
| | | N-terminal | | C-terminal |
| IgG2-Fc | TSL-1 | 39.6% ± 9.4% | TSL-3 | 61.4% ± 1.6% |
| mIgG4-Fc | TSL-2 | 34.1% ± 11.7% | TSL-4 | 63.3% ± 11.0% |
| HyFc | TSL-14 | Significantly lower than the control group | TSL-16 | Significantly lower than the control group |

Note:
the numbers in the Table are the splenic lymphocyte inhibition rate of mice As shown in FIGS. 8A-8F, data was compared to obtain the following results:

1) In vitro efficacy of the fusion protein constructed in the base of HyFc was significantly lower than that of the TSL-4 fusion protein in control group, therefore, HyFc was eliminated to be as a molecular chaperone to prolong the efficacy of HIM-3.

2) C-terminal linking mode, namely HM-3 is linked to a C-terminal of the Fc fragment, and its efficacy was significantly better than that of N-terminal linking mode, therefore, N-terminal linking was excluded.

3) Similarly, a C-terminal linking mode was taken, and the efficacy of TSL-4 was slightly higher than that of TSL-3. Therefore, it was preliminarily considered that mIgG4-Fc was batter than that of IgG2-Fc, and IgG2-Fc was retained temporarily. A further comparison was made between TSL-3 and TSL-4 in the subsequent experiment.

2, Linker Single Factor Comparison

Figure 9A:
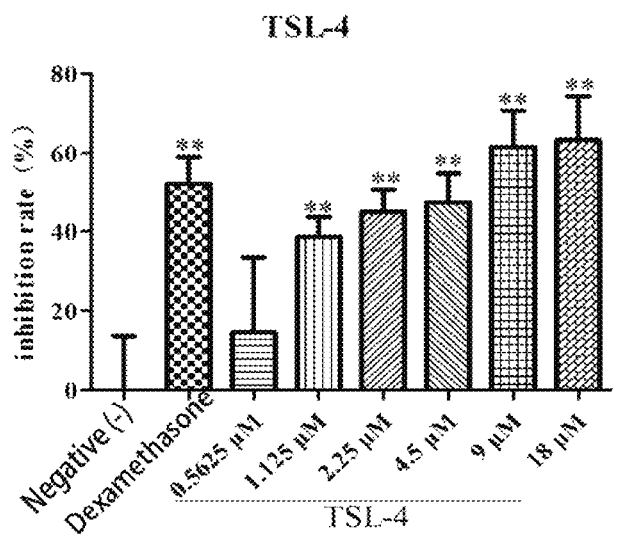
FIG. 9A shows a comparison diagram of the inhibition effect on splenic lymphocyte proliferation of Linker fusion protein TSL-4 in mice.
Figure 9B:
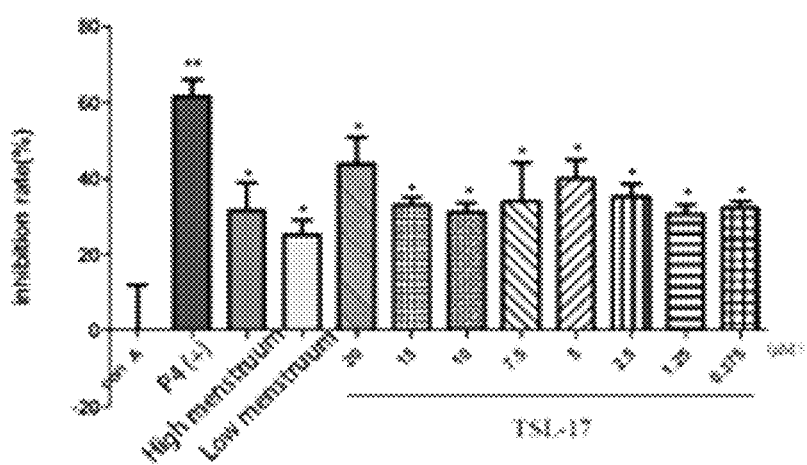
FIG. 9B shows a comparison diagram of the inhibition effect on splenic lymphocyte proliferation of Linker fusion protein TSL-17 in mice.
Figure 9C:
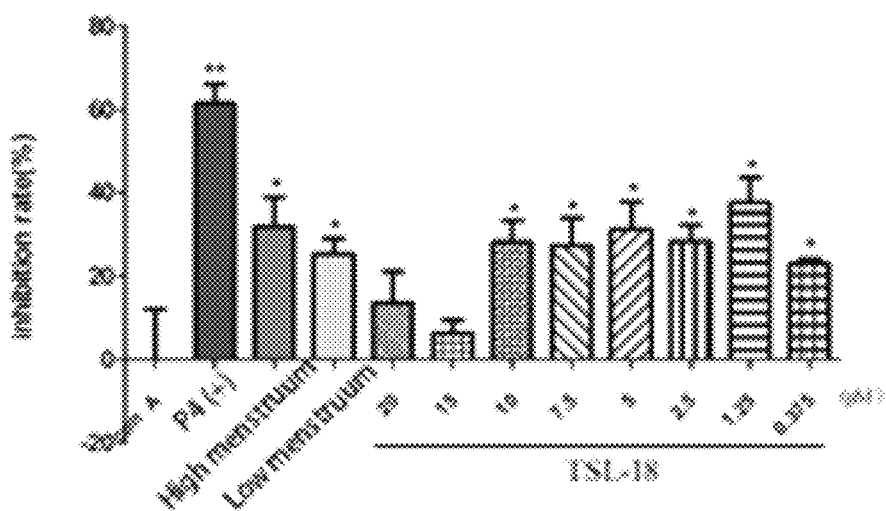
FIG. 9C shows a comparison diagram of the inhibition effect on splenic lymphocyte proliferation of Linker fusion protein TSL-18 in mice.
Figure 10A:
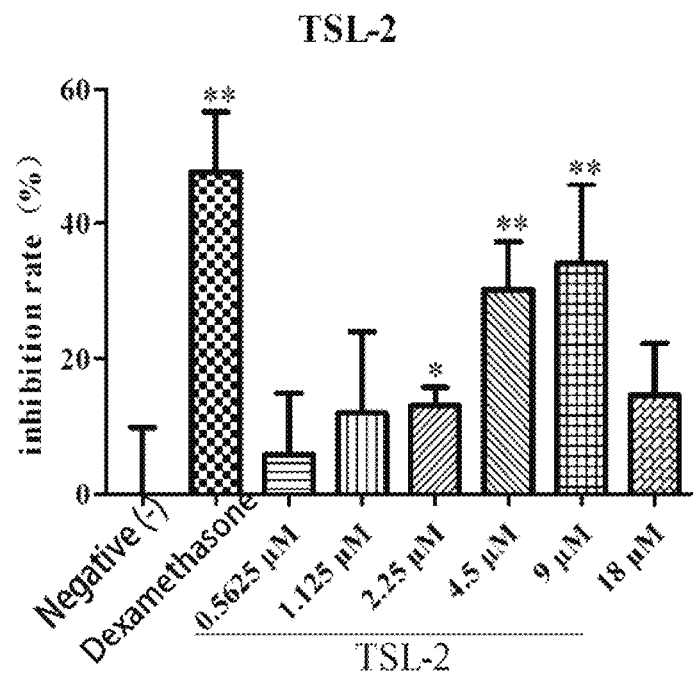
FIG. 10A shows a comparison diagram of the inhibitory effect on splenic lymphocyte proliferation of TLS-2 fusion protein in mice containing HM-3.
Figure 10B:
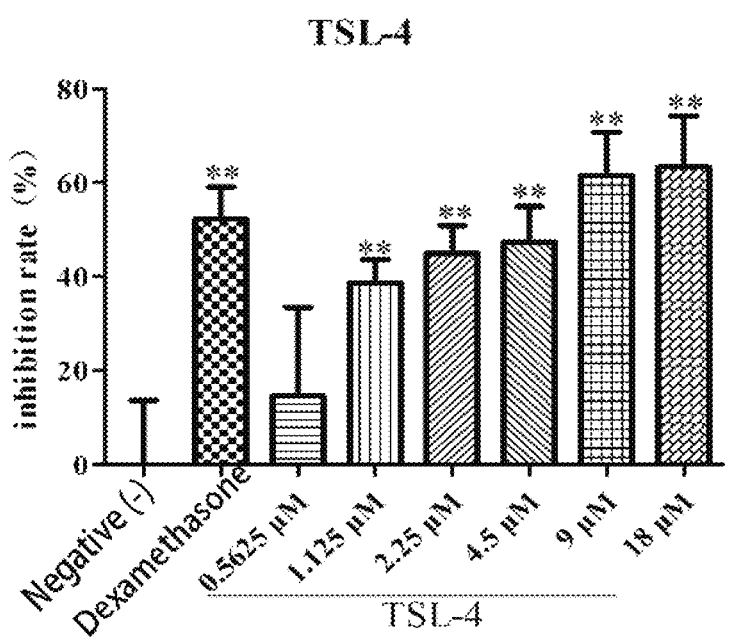
FIG. 10B shows a comparison diagram of the inhibitory effect on splenic lymphocyte proliferation of TLS-4 fusion protein in mice containing HM-3.
Figure 10C:
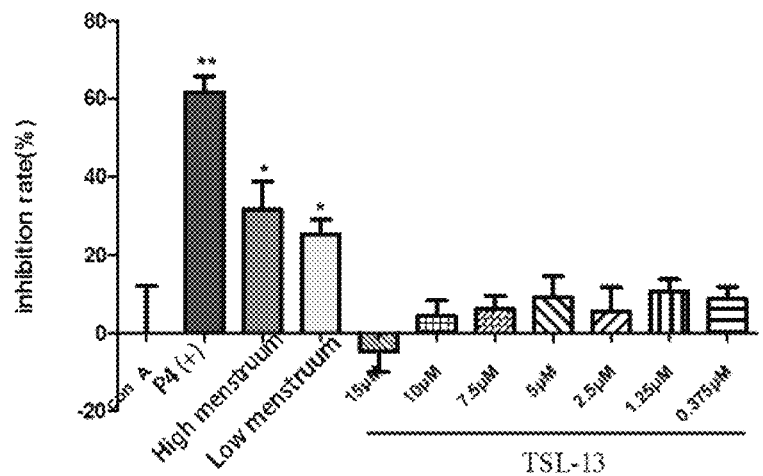
FIG. 10C shows a comparison diagram of the inhibitory effect on splenic lymphocyte proliferation of TLS-13 fusion protein in mice containing HM-3.
Figure 10D:
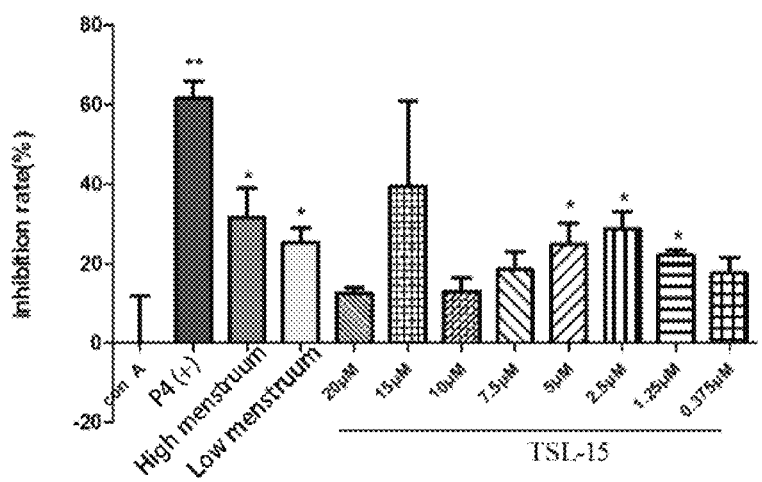
FIG. 10D shows a comparison diagram of the inhibitory effect on splenic lymphocyte proliferation of TLS-15 fusion protein in mice containing HM-3.
Figure 11A:
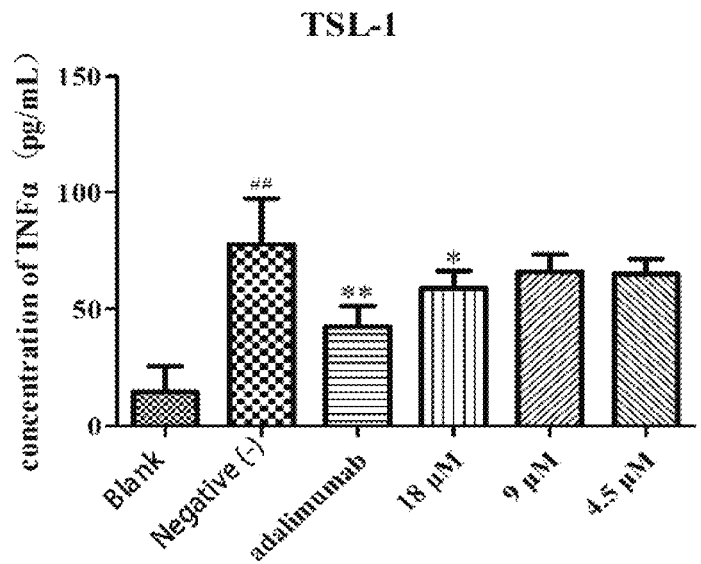
FIG. 11A shows a comparison diagram of the inhibiting effect of TSL-1 fusion protein on an inflammatory factor TNF-α production by human macrophage U937.
Figure 11B:
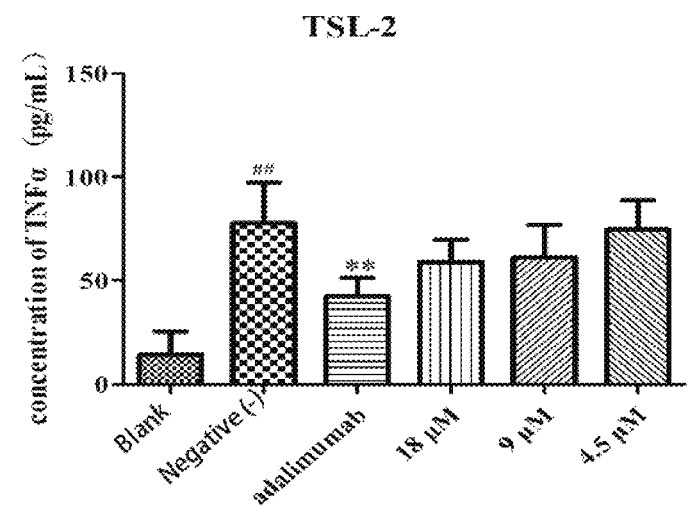
FIG. 11B shows a comparison diagram of the inhibiting effect of TSL-2 fusion protein on TNF-α production by human macrophage U937.
Figure 11C:
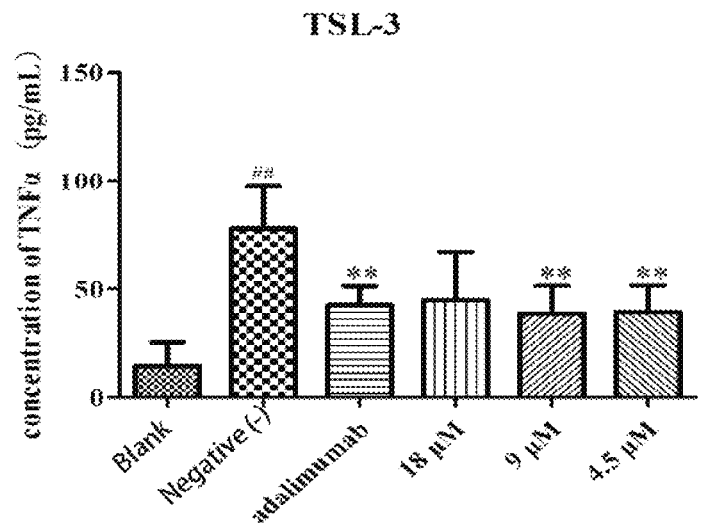
FIG. 11C shows a comparison diagram of the inhibiting effect of TSL-3 fusion protein on TNF-α production by human macrophage U937.
Figure 11D:
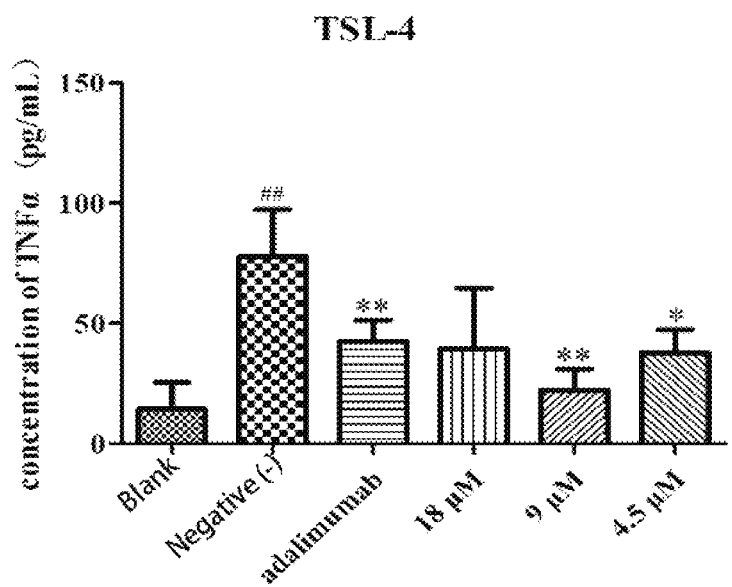
FIG. 11D shows a comparison diagram of the inhibiting effect of TSL-4 fusion protein on TNF-α production by human macrophage U937.
Figure 11E:
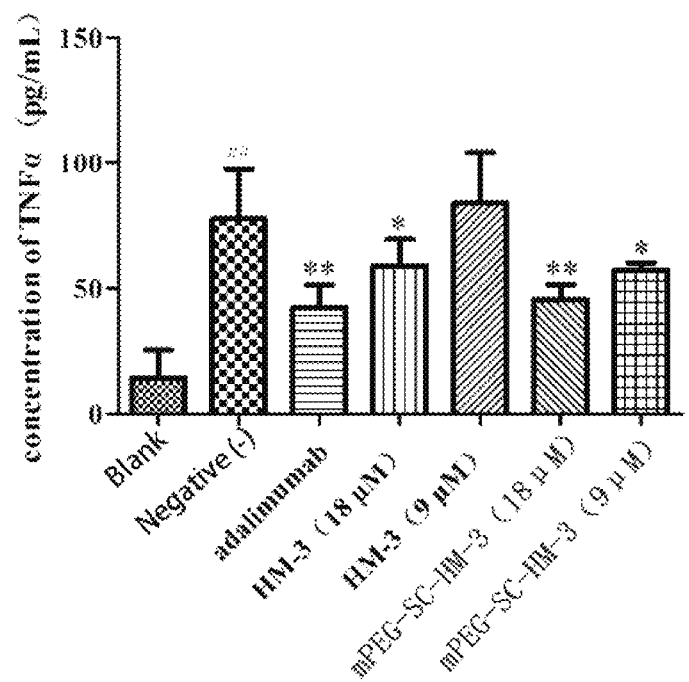
FIG. 11E shows a comparison diagram of the inhibiting effect of HM-3, mPEG-SC-HM-3, and mPEG-Sc-HM-3 on TNF-α production by human macrophage U937.

As shown in FIGS. 9A-9C, mIgG4-Fc and C-terminal linking mode were uniformly used in TSL-4, TSL-17, TSL-18; Linker was screened by comparing in vitro efficacy. The results of mice splenic lymphocyte proliferation inhibition experiments showed that the cell inhibition rate of TSL-17 and TSL-18 were lower than that of TSL-4, so it could be concluded that among the three types of Linker, such two rigid Linkers of A(EAAAK)$_n$A (SEQ ID NO: 27) and (AP)$_n$ were not suitable for the construction of Fc fusion protein of HM-3.

3, Comparison on Single HM-3 and Multiple HM-3 Fusion Proteins

Theoretically, the fusion protein molecule contains more HM-3, thus bringing stronger efficacy under the same dosage. Based on the idea, TSL-13 was designed to link HM-3 at both ends of the Fc fragment, and TSL-15 was designed to link two HM-3s at the C-terminal of the Fc fragment.

As shown in FIG. 10A-10D, mIgG4-Fc and GGGGS*3 Linker (SEQ ID NO: 26) were uniformly used in the mice splenic lymphocyte proliferation inhibition experiment to make a comparison on the in vitro efficacy of TSL-2, 4, 13, 15, and to analyze the action of multiple HM-3 on efficacy.

By comparison, it was found that the efficacy of TSL-13 and TSL-15 was lower than that of TSL-4 protein, and multiple HM-3 did not show the value of improving efficacy, therefore, the design scheme of fusion protein containing multiple HM-3 was eliminated.

By multiple rounds of comparison, it was confirmed that HM-3 was linked to a C-terminal of Fc; a single HM-3 molecule was ligated by a flexible GGGGS*3 Linker (SEQ ID NO: 26) to keep the efficacy of HM-3 to the maximum extent; a comparison was made on the two Fc fragments of IgG2-Fc and mIgG4-Fc, mIgG4-Fc achieved a better efficacy, but it was not enough to eliminate IgG 2-Fc. Thus, the two structures of TSL-3 and TSL-4 were further compared in subsequent experiments.

Embodiment 9: In Vitro Efficacy Screening of the HM-3 Fusion Protein in Inhibition Reaction of Human Macrophage U937

Experimental method: Human macrophage U937 was cultured in RPMI-1640 medium containing 10% fetal bovine serum and double antibodies in a constant temperature incubator at 37° C. under the condition of 5% $CO_2$, and the medium was replaced every 2 days. U937 cells in the logarithmic phase were collected, resuspended and adjusted to the concentration of $5\times10^5$/mL. 100 µL of cells was added to each well of a 96-well plate overnight and induced with LPS (1 µg/mL) in the following day, where n=3. At the same time, the cells were treated with agents, and respectively divided into a positive control group adalimumab, an HM-3 polypeptide group, an mPEG-SC-HM-3 polypeptide group, an HM-3 fusion protein (TSL-1, TSL-2, TSL-3, TSL-4) group, and the specific dosing scheme was shown in Table 5.

TABLE 5

| | dosing scheme | | |
|---|---|---|---|
| Group | Culture medium | LPS | Dosage |
| Blank | 100 µL | / | / |
| Negative | 90 µL | 10 µL, 1 µg/mL | / |
| adalimumab | / | 10 µL, 1 µg/mL | 50 µg/mL, 90 µL |
| HM-3 | / | 10 µL, 1 µg/mL | 9, 18 µmol/L, 90 µL |
| mPEG-SC-HM-3 | / | 10 µL, 1 µg/mL | 9, 18 µmol/L, 90 µL |
| HM-3 fusion Protein (TSL-1, TSL-2, TSL-3, TSL-4) | / | 10 µL, 1 µg/mL | 4.5, 9, 18 µmol/L, 90 µL |

48 h after the agents worked, culture medium was collected and centrifuged, and supernatant was taken to measure the content of TNF-α therein by ELISA. Test results were expressed as mean±SD, and statistical T test was performed. *$P<0.05$ indicates significant difference, **$P<0.01$ indicates extremely significant difference. Based upon the results, the efficacy of the HM-3 fusion protein against rheumatoid arthritis was screened.

Experimental results: As shown in FIGS. 11A-11E, in order to screen the anti-rheumatoid arthritis of HM-3 fusion proteins TSL-1, TSL-2, TSL-3 and TSL-4; in the experiment, ELISA was taken to detect the content of TNF-α in supernatant of LPS-induced macrophage, thus determining the activity of anti-rheumatoid arthritis of HM-3 fusion proteins TSL-1, TSL-2, TSL-3 and TSL-4. The results indicated that the dosage (9 µM) of HM-3 fusion proteins TSL-3 and TSL-4 showed an best inhibitory effect; the TNF-α content in cell supernatant was 38.6±12.9 pg/mL and 22.2±8.9 pg/mL. Compared with the negative group (77.6±19.6 pg/mL), there was a significant difference. In addition, the TNF-α content in cell supernatant of the high/low-dosage HM-3 was respectively 58.9±10.6 pg/mL and 83.9±20.4 pg/mL. The content of TNF-α in cell supernatant of high/low-dosage mPEG-SC-HM-3 was 45.6±5.9 pg/mL, 57.3±2.7 pg/mL respectively. From the aspect of inhibitory effect, TSL-4 was much better than that of polypeptide HM-3 and mPEG-SC-HM-3.

Embodiment 10: Screening of In Vivo Anti-Angiogenesis Effects of the HM-3 Fusion Protein in Zebrafish Experimental method: transgenic blood vessel fluorescent zebrafish was randomly selected and put into a six-well plate with 30 fish per well, and intravenously injected HM-3 polypeptide, TSL-1 fusion protein, TSL-2 fusion protein, TSL-3 fusion protein and TSL-4 fusion protein respectively in accordance with the dosage of 20 ng/tail and 66 ng/tail; the dosage was 500 nL/tail in Avastin positive control and the injection volume was 20 nL/tail; the zebrafish injected 20 nL/tail of buffer solution served as a solvent control group, and the zebrafish without any treatment served as a normal control group. 10 pieces of zebrafish were randomly selected from each group after processed for 24 h to observe the intestinal vessels of the transgenic zebrafish by a fluorescence microscope, as well as to take and maintain images. Image analysis was performed by Nikon MS-Elements D 3.10 to calculate the area (S) of SIVs (subintestinal vessel, SIV). The calculation formula of angiogenesis inhibition rate was as follows:

Angiogenesis inhibition rate (%)=(1−$S$(Test sample group)/$S$(Normal control group))×100%

Statistical analysis was performed by variance analysis and Dunnett's T-test and the results were expressed as Mean±SD, where p<0.05 indicates a significant difference.

Figure 12:
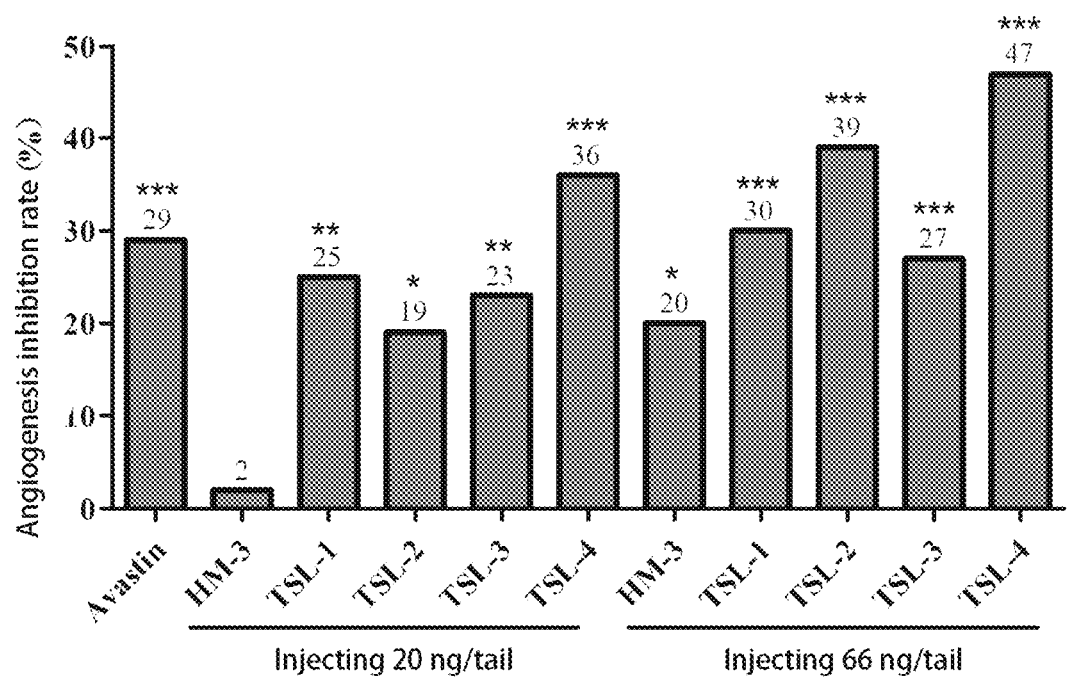
FIG. 12 shows a comparison diagram of inhibition ratio of TSL-1-4 fusion proteins on the angiopoiesis of zebra fish.

Experimental Results:

As shown in FIG. 12, a comparison of SIVs area was made between the positive control group (Avastin 500 ng/tail) (37853) and the normal control group (53193), and p<0.001 (compared with the normal control group, *p<0.05, p<0.01, *p<0.001), and the inhibition rate of angiogenesis was 29%, indicating that Avastin has obvious angiogenesis inhibition effect.

The area of SIVs was respectively 52186, 39929, 42828, 40705 and 33869 when zebrafish was injected 20 ng/tail with HM-3 polypeptide, 20 ng/tail TSL-1, 20 ng/tail TSL-2, 20 ng/tail TSL-3 and 20 ng/tail TSL-4 fusion proteins. Compared with the normal control group (53193), the inhibition rate of angiogenesis was 2%, 25%, 19%, 23% and 36% respectively. The results showed that HM-3 polypeptide had no inhibiting effect on angiogenesis at the dose of 20 ng/tail; the fusion proteins TSL-1, TSL-2, TSL-3 and TSL-4 had significant inhibitory effect on angiogenesis at the dose of 20 ng/tail, of which TSL-4 achieved the best inhibitory effect on angiogenesis.

The area of SIVs was 42492, 37022, 32374, 38660 and 28297 respectively when the dosage of HM-3, TSL-1, TSL-2, TSL-3 and TSL-4 was 66 ng/tail. Compared with the normal control group (53193), the inhibition rate of angiogenesis was 20%, 30%, 39%, 27% and 47% respectively. It indicated that the five fusion proteins had significant inhibiting effect on angiogenesis at the dose of 66 ng/tail, of which TSL-4 achieved the best effect.

Embodiment 11: Chronic Inflammation Mode of Type-II CIA in Mice

Experimental method: Balb/c mice were taken and immunized for the first time. The concentration of type-II bovine collagen was 4 mg/mL. On the day of the experiment (day 0), complete Freund's adjuvant (CFA) and CII solution were mixed evenly in equal volume and emulsified. Excepting for the normal control group of Balb/c mice, mice in each group were sensitized by intracutaneous injection of 50 μL emulsifier at the end of tails. 21 days later, mice were re-immunized with the same dose of emulsifier at the end of tails, and incomplete Freund's adjuvant (IFA) served as an adjuvant at this time. Redness and swelling other arthritic symptoms appeared on toe joints of mice models approximately on the $29^{th}$ day of the experiment, indicating successful modeling.

Treatment Method

Animals in the modeling group on the $30^{th}$ day of the experiment were randomly divided into:

G1 (normal control group);
G2 (model group);
G3 (positive Adalimumab group);
G4 (HIM-3 group);
G5 (mPEG-SC-HM-3 group);
G6 (TSL-4, 50 mg/kg, administered once for 5 days, 3 times in total);
G7 (TSL-4, 25 mg/kg, administered once for 5 days, 3 times in total);
G8 (TSL-4, 25 mg/kg, administered once for 7 days, 2 times in total);
G9 (TSL-4, 25 mg/kg, administered once for 14 days, 1 time in total);
G10 (TSL-4, 12.5 mg/kg, administered once for 5 days, 3 times in total);
G11 (TSL-4, 12.5 mg/kg, administered once for 7 days, 2 times in total);
G12 (TSL-4, 12.5 mg/kg, administered once for 14 days, 1 time in total);

There were 12 groups in total, and there were 8 pieces of mice in remaining each group excepting for 12 pieces in G1 (normal control group) and G2 (model group). Mice in the normal control group and the model control group were injected with normal saline subcutaneously once every other day for 8 times in total with the dosage volume of 0.1 mL/10 g; mice in the positive Adalimumab group were subcutaneously injected with 8 mg/kg Adalimumab once every two weeks with the dosage volume of 0.1 mL/10 g, and then the mice were observed for another 15 days after 15 days of treatment. Specific dosing scheme was shown in Table 6.

TABLE 6 dosing scheme

| Group | n | Dosage of administration | Frequency | Route |
|---|---|---|---|---|
| Normal group (G1) | 12 | Normal saline | 1 time/2 d, 8 times | SC |
| Model group (G2) | 12 | Normal saline | 1 time/2 d, 8 times | SC |
| Adalimumab (G3) | 8 | 8 mg/kg | 1 time/14 d, 1 time | SC |
| HM-3 (G4) | 8 | 1.6 mg/kg | 2 times/d, 30 times | IV |
| mPEG-SC-HM-3 (G5) | 8 | 20 mg/kg | 1 time/2 d, 8 times | SC |
| TSL-4 (G6) | 8 | 50 mg/kg | 1 time/5 d, 3 times | SC |
| TSL-4 (G7) | 8 | 25 mg/kg | 1 time/5 d, 3 times | SC |
| TSL-4 (G8) | 8 | 25 mg/kg | 1 time/7 d, 2 times | SC |
| TSL-4 (G9) | 8 | 25 mg/kg | 1 time/14 d, 1 time | SC |
| TSL-4 (G10) | 8 | 12.5 mg/kg | 1 time/5 d, 3 times | SC |
| TSL-4 (G11) | 8 | 12.5 mg/kg | 1 time/7 d, 2 times | SC |
| TSL-4 (G12) | 8 | 12.5 mg/kg | 1 time/14 d, 1 time | SC |

Arthritis Index Evaluation

Measurement of mice weight: mice were weighed by an electronic balance every two days.

Measurement of sole thickness: the thickness of left, right and hind soles for each mouse was measured by a vernier caliper every two days.

Measurement of ankle joint width: the width of left and right ankle joints for each mouse was measured by vernier caliper every two days.

Arthritis index (AI) score: the severity of arthritis for each mouse was evaluated by a paw joint scoring method. 0: no redness and swelling; 1: redness and swelling of little toe joints; 2: redness and swelling of toe joints and toes; 3: redness and swelling of the portion below ankle joints; 4: redness and swelling of toe joints, toes and ankle joints. Scoring was performed once every two days until the end of the experiment.

Pathological Index Evaluation

Blood was collected from the orbit and serum was separated. After mice were killed by cervical dislocation, spleen and thymus were separated and weighed to calculate a spleen coefficient, and then the spleen and thymus were fixed in formalin stationary liquid. Paw was cut off from the joint part of superior borders between malleolus medialis and lateral malleolus at the extremitas anterior of tibia, and the entrire paw including ankle joints were weighed and fixed in formalin stationary liquid for histopathological examination.

Experimental results: TSL-4 had different therapeutic effects on type-II CIA mice models based upon different dosage regimens, where better therapeutic effect achieved in group G3 (positive Adalimumab group), group G4 (HM-3 group), group G5 (mPEG-SC-HM-3 group), group G6 (TSL-4, 50 mg/kg, administrated once for 5 days, 3 times in total), group G7 (TSL-4, 25 mg/kg, administered once for 5 days, 3 times in total), group G8 (TSL-4, 25 mg/kg, administered once for 7 days, 2 times in total), group G10 (TSL-4, 12.5 mg, administered once for 5 days, 3 times in total); compared with the model group, there were significant differences ($*p<0.05$) in paw thickness, ankle width, paw circumference, arthritis scoring, spleen weight and paw weight; the therapeutic effect of the group G5 (mPEG-SC-HM-3 group), group G6 (TSL-4, 50 mg/kg, administrated once for 5 days, 3 times in total), group G7 (TSL-4, 25 mg/kg, administered once for 5 days, 3 times in total), group G8 (TSL-4, 25 mg/kg, administered once for 7 days, 2 times in total) was better than the group G3 (positive Adalimumab group), while there was no significant difference among them. Based on the index of paw thickness, ankle width, paw circumference and arthritis scoring, it was found that the effect of the group G3 (positive Adalimumab group) was better than that of other groups in early stage of the therapy; in middle and late stage of the therapy, the therapeutic effect of the group G3 (positive Adalimumab group) was inferior to that of the group G5 (mPEG-SC-HM-3 group), group G6 (TSL-4, 50 mg/kg, administrated once for 5 days, 3 times in total), group G7 (TSL-4, 25 mg/kg, administered once for 5 days, 3 times in total), group G8 (TSL-4, 25 mg/kg, administered once for 7 days, 2 times in total); moreover, the therapeutic effect of the group G4 (HM-3 group) and group G10 (TSL-4, 12.5 mg, administered once for 5 days, 3 times in total) was slightly lower than that of the group G3 (positive Adalimumab group), and compared with the group G2 (model group), there was a significant difference ($*p<0.05$), while compared with the group G3 (positive Adalimumab group), there was no significant difference; based upon the dynamic curve of weight and in-vitro toxicity test on normal cells, it was found that there was no obvious toxic and side effect in each therapeutic group.

1. Effect of TSL-4 on Weight of the Type-II CIA Mice

Figure 13A:
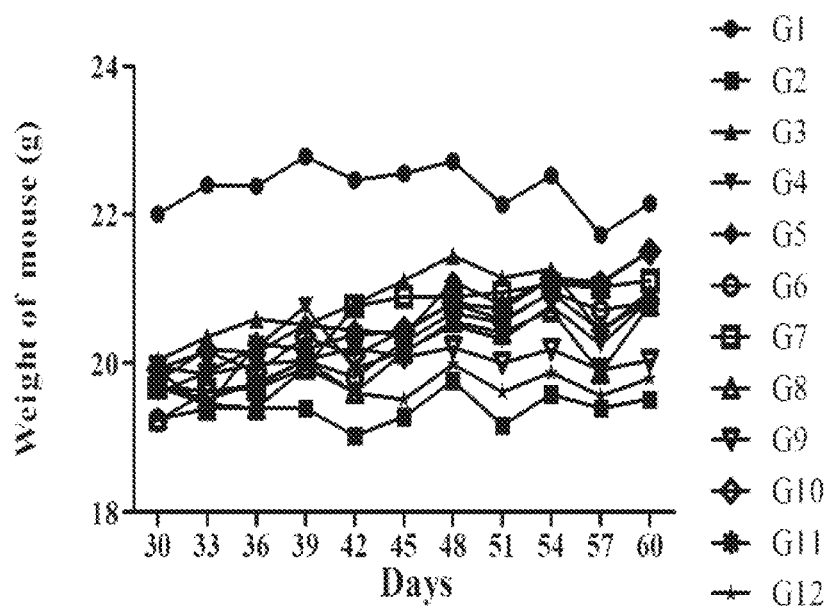
FIG. 13A is a diagram showing the influence of TSL-4 on weight of type-II CIA mice after 30-60 days.
Figure 13B:
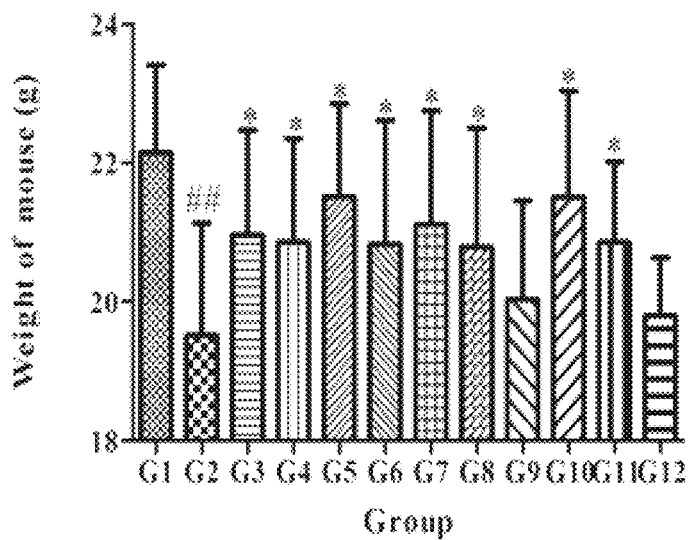
FIG. 13B is a diagram showing the influence of TSL-4 on weight of type-II CIA mice after 60 days.

As shown in FIGS. 13A-13B, the weight of mice in groups G3, G4, G5, G6, G7, G8, G10 was 21.0±1.5, 20.9±1.5, 21.5±1.3, 20.8±1.8, 21.1±1.6, 20.8±1.7, 21.5±1.5 g at the end of the experiment on the $60^{th}$ day; compared with the model group (group G2, 19.5±1.6 g), the weight increased obviously;

2. Effect of TSL-4 on Sole Thickness of the Type-II CIA Mice

Figure 14A:
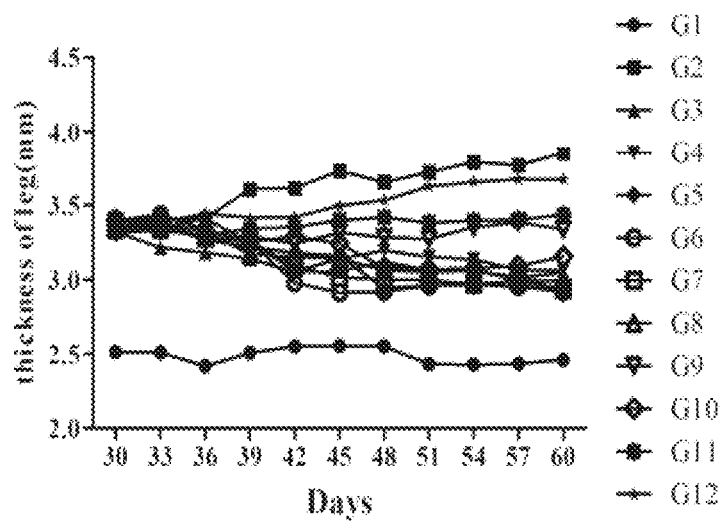
FIG. 14A is a diagram showing the influence of TSL-4 on sole thickness of type-II CIA mice after 30-60 days.
Figure 14B:
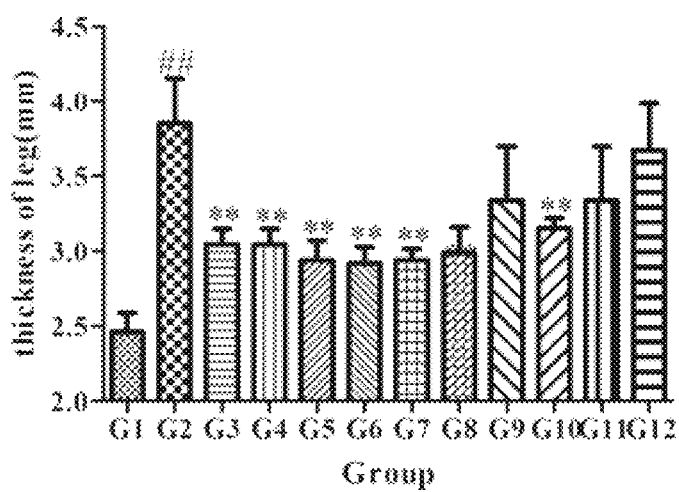
FIG. 14B is a diagram showing the influence of TSL-4 on sole thickness of type-II CIA mice after 60 days.

As shown in FIGS. 14A-14B, the sole thickness of mice in groups G3, G4, G5, G6, G7, G8, G10 was 3.0410.11, 3.0610.23, 2.9410.13, 2.9210.11, 2.9410.07, 2.9910.17, 3.1510.07 mm at the end of the experiment on the 60th day; compared with the model group (group G2, 3.8510.30 mm), there was a significant difference;

3. Effect of TSL-4 on Ankle Width of the Type-II CIA Mice

Figure 15A:
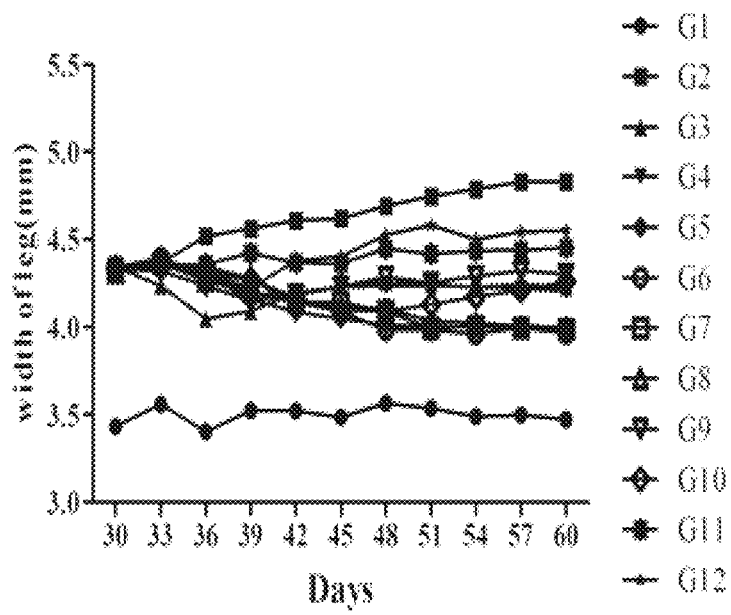
FIG. 15A is a diagram showing the influence of TSL-4 on ankle width of type-II CIA mice after 30-60 days.
Figure 15B:
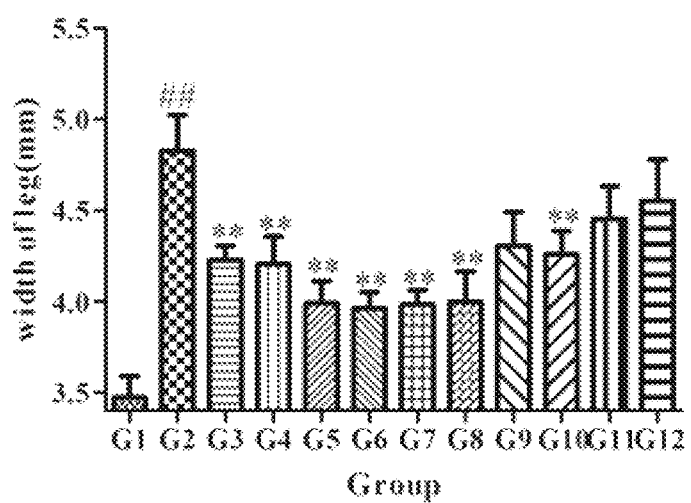
FIG. 15B is a diagram showing the influence of TSL-4 on ankle width of type-II CIA mice after. 60 days

As shown in FIGS. 15A-15B, the ankle width of mice in groups G3, G4, G5, G6, G7, G8, G10 was 4.23±0.08, 4.21±0.15, 3.99±0.12, 3.96±0.09, 3.98±0.08, 4.00±0.16, 4.26±0.13 mm at the end of the experiment on the 60th day; compared with the model group (group G2, 4.83±0.20 mm), the ankle width increased obviously;

4. Effect of TSL-4 on Paw Circumference of the Type-II CIA Mice

Figure 16A:
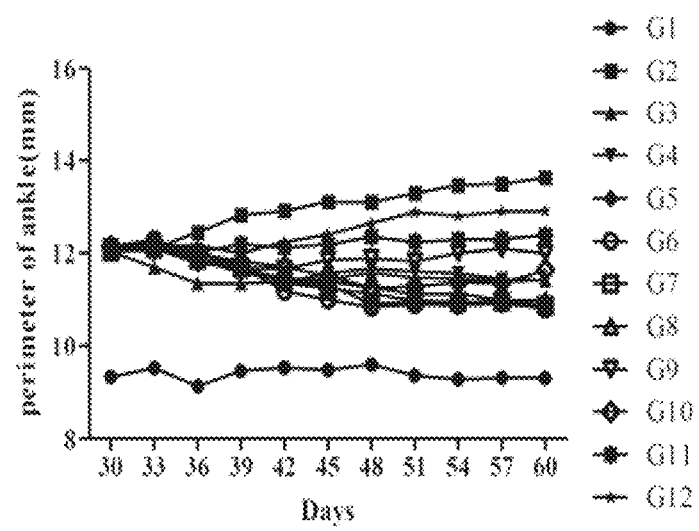
FIG. 16A is a diagram showing the influence of TSL-4 on paw circumference of type-II CIA mice after 30-60 days.
Figure 16B:
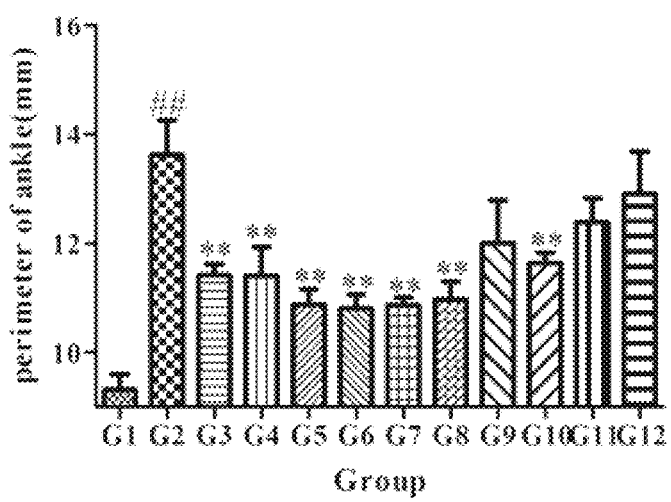
FIG. 16B is a diagram showing the influence of TSL-4 on paw circumference of type-II CIA mice after 60 days.

As shown in FIGS. 16A-16B, the paw circumference of mice in groups G3, G4, G5, G6, G7, G8, G10 was 11.42±0.20, 11.41±0.53, 10.88±0.28, 10.80±0.26, 10.87±0.14, 10.97±0.32, 11.64±0.19 mm at the end of the experiment on the 60th day; compared with the model group (group G2, 13.6210.64 mm), there was an extremely significant difference;

5. Effect of TSL-4 on Arthritis Scoring of the Type-II CIA Mice

Figure 17A:
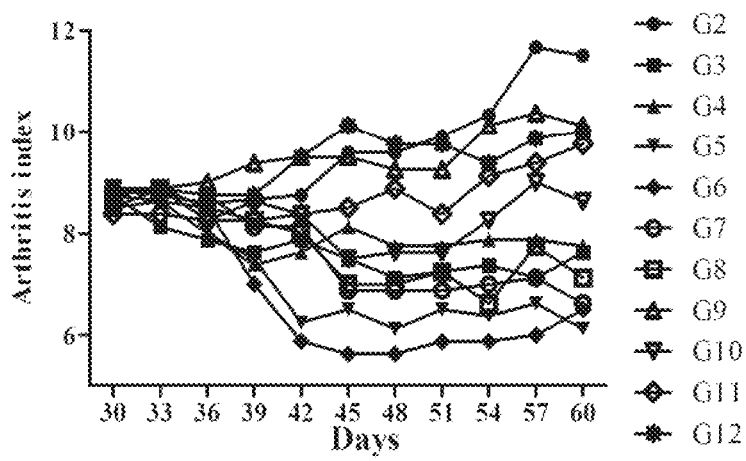
FIG. 17A is a diagram showing the influence of TSL-4 on arthritis scoring of type-II CIA mice after 30-60 days.
Figure 17B:
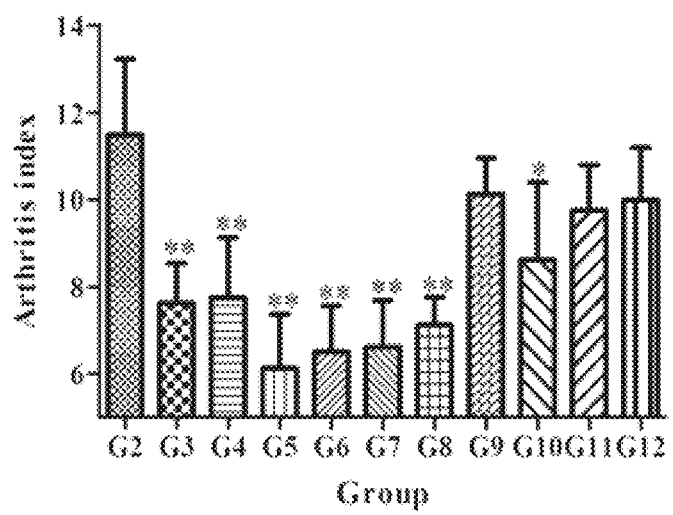
FIG. 17B is a diagram showing the influence of TSL-4 on arthritis scoring of type-II CIA mice after 60 days.

As shown in FIGS. 17A-17B, the arthritis scoring of mice in groups G3, G4, G5, G6, G7, G8, G10 was 7.6±0.9, 7.8±1.4, 6.1±1.2, 6.5±1.1, 6.6±1.1, 7.1±0.6, 8.6±1.8 at the end of the experiment on the 60th day; compared with the model group (group G2, 11.5±1.7), there was an extremely significant difference;

6. Effect of TSL-4 on Spleen and Thymus of the Type-II CIA Mice

Figure 18A:
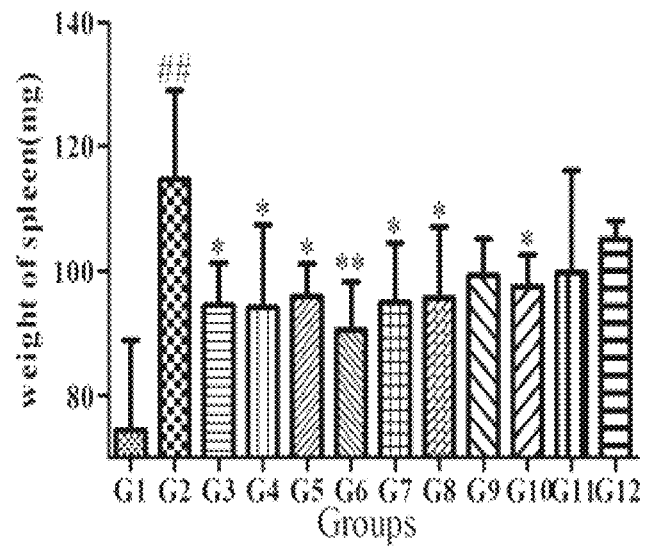
FIG. 18A is a diagram showing the influence of TSL-4 on spleen weight of type-II CIA mice.
Figure 18B:
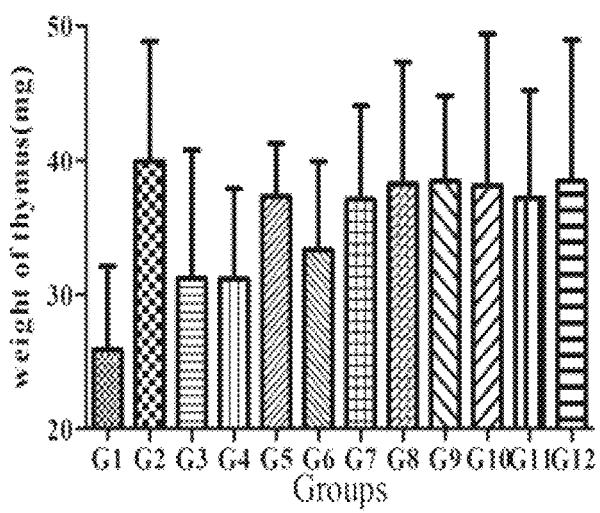
FIG. 18B is a diagram showing the influence of TSL-4 on thymus weight of type-II CIA mice.

As shown in FIGS. 18A-18B, the spleen weight of mice in groups G3, G4, G5, G7, G8, G10 was 94.6±6.7 mg, 94.2±13.3 mg, 96.0±5.2 mg, 95.1±9.5 mg, 95.8±11.4 mg, 97.5±5.1 mg at the end of the experiment on the $60^{th}$ day; compared with the model group (group G2, 114.6±14.5 mg), there was an significant difference; excepting for a significant difference ($*p<0.05$) of the mice thymus weight between the model group (39.9±8.9 mg) and the normal control group (25.9±6.2 mg), there was no significant difference between the remaining each group and the model group.

7. Effect of TSL-4 on Paw Weight of the Type-II CIA Mice

Figure 19:
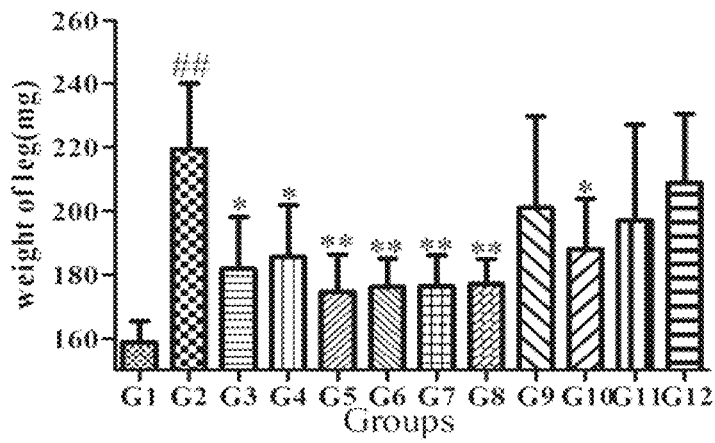
FIG. 19 is a diagram showing the influence of TSL-4 on paw weight of type-II CIA mice.

As shown in FIG. 19, the paw weight of mice in groups G5, G6, G7, G8 was 174.6±11.7 mg, 176.2±8.9 mg, 176.4±9.7 mg, 177.1±7.8 mg at the end of the experiment on the $60^{th}$ day; compared with the model group (group G2, 219.3±20.6 mg), there was an significant difference.

It was seen from the above conclusion that the TSL-4 fusion protein of the application could still achieve the therapeutic effect the same as that of the group G4 (administered twice per day) and group G5 (administered once for two days) under the conditions of groups G6, G7 and G10 (administered once for 5 days) and even the group G8 (administered once for 7 days); moreover, there was an equivalent dosage in groups G4, G5, G7 after converted in an equimolar manner, indicating that the half-life of the fusion protein in the application prolonged significantly.

Embodiment 12: Pharmacokinetic Analysis of TSL-4

1. Mode of Administration of SD Rats (1) 18 SD rats (half male and half female) were purchased and fed for one week.

(2) Rats were divided into 3 groups, half male and half female, and weight of rats were recorded respectively.

(3) 4.17, 12.5 and 37.5 mg/kg of TSL-4 were subcutaneously administered on the back for once, and blood sampling was performed from orbit respectively at 0 h, 0.5 h, 1 h, 3 h, 5 h, 6 h, 7 h, 8 h, 10 h, 12 h, 16 h, 20 h, 24 h, 28 h, 41 h, 53 h, 65 h, 77 h. The blood was centrifuged at 12000 rpm/min to take 200 μL of supernatant, then the supernatant was diluted with PBS solution according to a ratio of 1:3, and finally placed in an EP tube and stored in a −80° C. refrigerator.

(4) Biological samples were measured by double-antibody sandwich ELISA.

2. Detection Mode of Plasma Concentration

Establishment for the Basic Procedure of Double-Antibody Sandwich ELISA (1) Coating, HM-3 monoclonal antibody was diluted with a coating buffer (CBS) in certain concentration, added to an ELISA plate and coated overnight.

(2) Plate washing, the coating buffer was discarded, and the plate was washed by PBST for 3 times, and then dried by patting.

(3) Sealing, a blocking buffer was added for sealing at 37.5° C., the plate washing process was repeated and the plate was dried by patting.

(4) Addition of samples to be measured, the samples to be measured were added to the ELISA plate with multiple wells, and then incubated at 37.5° C.; the plate washing process was repeated and the plate was dried by patting.

(5) Addition of a secondary antibody, the secondary antibody diluted proportionally was added for incubation at 37.5° C. The plate washing process was repeated and the plate was dried by patting.

(6) Addition of the enzyme-labeled secondary antibody for reaction, the HRP-labeled secondary antibody which was diluted by 5% skim milk powder solution according to certain proportion was added for incubation at 37.5° C. The plate washing process was repeated and the plate was dried by patting.

(7) Addition of a substrate, a TMB substrate in certain volume L was added for reaction in the dark.

(8) Termination of the reaction, a certain amount of stop buffer was added to terminate the reaction.

(9) Detection, read OD450 nm with a microplate reader.

3. Experimental Results 3.1 Results of Pharmacokinetics of SD Rats with a Single Subcutaneous Injection of 12.5 mg/kg TSL-4

Figure 20:
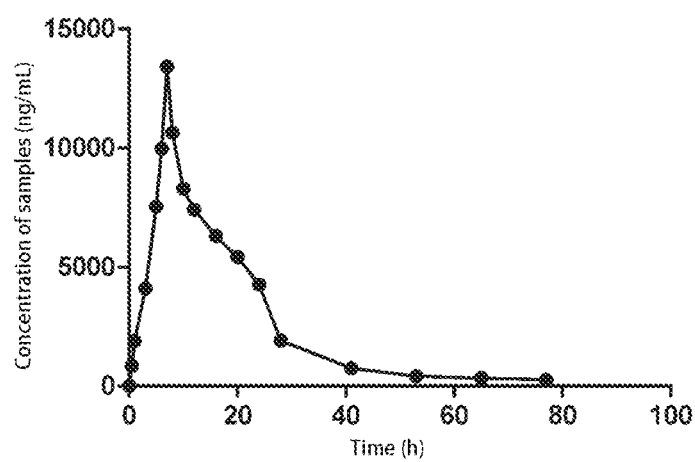
FIG. 20 shows a plasma concentration time curve after receiving 12.5 mg/kg TSL-4 via single subcutaneous injection.

After receiving a single subcutaneous injection of 12.5 mg/kg TSL-4, results of the plasma concentration-time curve were shown in FIG. 20, measured results of the plasma concentration were shown in Table 7, and results of the pharmacokinetic parameters were shown in Table 10.

TABLE 7

Plasma concentration of rats after receiving a single subcutaneous injection of 12.5 mg/kg TSL-4 (unit: μg/mL)

| Time/h | Rat No. 1 | 2 | 3 | 4 | 5 | Mean |
|---|---|---|---|---|---|---|
| 0.00 | NA | NA | NA | NA | NA | NA |
| 0.50 | 0.176 | 0.741 | 0.995 | 0.598 | 1.728 | 0.848 |
| 1.00 | 0.740 | 1.435 | 1.875 | 1.153 | 4.180 | 1.877 |
| 3.00 | 1.459 | 2.970 | 4.100 | 2.070 | 9.793 | 4.078 |
| 5.00 | 2.030 | 5.512 | 8.329 | 6.748 | 14.973 | 7.518 |
| 6.00 | 2.337 | 7.869 | 11.753 | 9.720 | 18.172 | 9.970 |
| 7.00 | 3.372 | 8.202 | 11.959 | 7.582 | 35.951 | 13.413 |
| 8.00 | 4.395 | 6.684 | 10.711 | 6.343 | 24.998 | 10.626 |
| 10.00 | 3.014 | 5.271 | 9.706 | 6.000 | 17.430 | 8.284 |
| 12.00 | 2.663 | 4.448 | 7.496 | 5.562 | 16.780 | 7.390 |
| 16.00 | 2.587 | 3.719 | 6.053 | 4.976 | 14.124 | 6.292 |
| 20.00 | 1.900 | 3.086 | 5.605 | 3.962 | 12.480 | 5.407 |
| 24.00 | 1.822 | 2.513 | 2.747 | 3.966 | 10.192 | 4.248 |
| 28.00 | 0.336 | 1.653 | 0.766 | 2.703 | 4.077 | 1.907 |
| 41.00 | 0.241 | 0.700 | 0.417 | 1.185 | 1.189 | 0.746 |
| 53.00 | 0.131 | 0.542 | 0.247 | 0.734 | 0.357 | 0.402 |
| 65.00 | 0.127 | 0.396 | 0.181 | 0.648 | 0.299 | 0.330 |
| 77.00 | 0.064 | 0.285 | 0.160 | 0.505 | 0.290 | 0.261 |

NA means below the lower limit of detection 3.2 Pharmacokinetic results of SD rats after receiving a single subcutaneous injection of 37.5 mg/kg TSL-4

Figure 21:
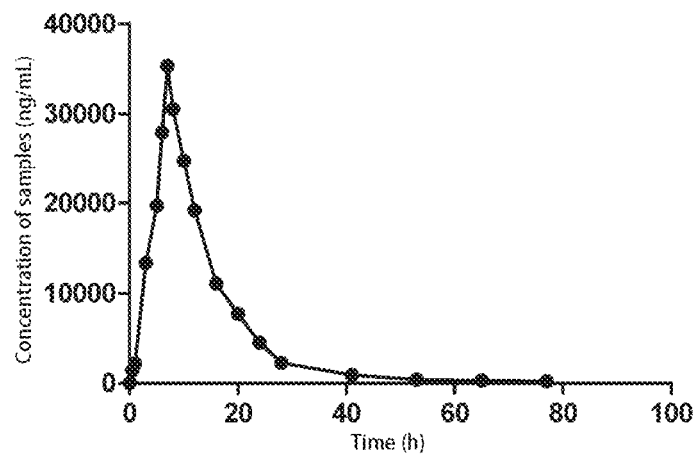
FIG. 21 shows a plasma concentration time curve after receiving 37.5 mg/kg TSL-4 via single subcutaneous injection.

After receiving a single subcutaneous injection of 37.5 mg/kg TSL-4, results of the plasma concentration-time curve were shown in FIG. 21, measured results of the plasma concentration were shown in Table 8, and results of the pharmacokinetic parameters were shown in Table 10.

TABLE 8

Plasma concentration of rats after receiving a single subcutaneous injection of 37.5 mg/kg TSL-4 (unit: μg/mL)

| Time/h | Rat No. 1 | 2 | 3 | 4 | 5 | Mean |
|---|---|---|---|---|---|---|
| 0.00 | NA | NA | NA | NA | NA | NA |
| 0.50 | 1.180 | 1.202 | 1.816 | 1.534 | 1.277 | 1.402 |
| 1.00 | 1.974 | 1.514 | 2.370 | 1.151 | 3.838 | 2.169 |
| 3.00 | 23.044 | 13.341 | 9.819 | 5.861 | 14.678 | 13.349 |
| 5.00 | 36.313 | 18.726 | 10.891 | 12.949 | 19.600 | 19.696 |
| 6.00 | 44.277 | 20.173 | 20.450 | 16.158 | 38.541 | 27.920 |
| 7.00 | 64.960 | 21.479 | 38.009 | 22.359 | 29.552 | 35.272 |
| 8.00 | 62.784 | 25.446 | 31.080 | 12.944 | 20.137 | 30.478 |
| 10.00 | 44.656 | 21.055 | 21.153 | 10.006 | 26.810 | 24.736 |
| 12.00 | 36.576 | 17.149 | 17.361 | 8.919 | 15.856 | 19.172 |
| 16.00 | 13.903 | 7.767 | 12.942 | 6.885 | 13.925 | 11.084 |
| 20.00 | 9.514 | 3.313 | 9.915 | 4.605 | 11.259 | 7.721 |
| 24.00 | 4.801 | 3.205 | 5.617 | 3.076 | 5.918 | 4.523 |
| 28.00 | 1.952 | 2.730 | 3.953 | 1.833 | 0.959 | 2.285 |
| 41.00 | 0.780 | 0.912 | 1.824 | 0.779 | 0.303 | 0.920 |
| 53.00 | 0.431 | 0.466 | 0.510 | 0.391 | 0.237 | 0.407 |
| 65.00 | 0.357 | 0.301 | 0.370 | 0.291 | 0.243 | 0.312 |
| 77.00 | 0.269 | 0.253 | 0.169 | 0.244 | 0.138 | 0.215 |

NA means below the lower limit of detection 3.3 Pharmacokinetic results of SD rats after receiving a single subcutaneous injection of low-dose TSL-4

Figure 22:
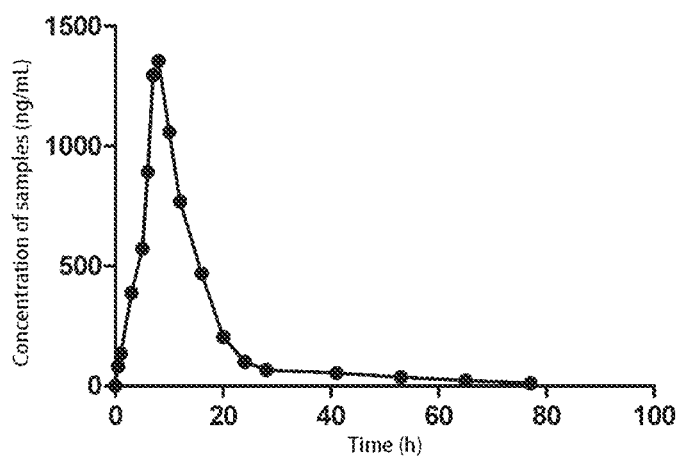
FIG. 22 shows a plasma concentration time curve after receiving 4.17 mg/kg TSL-4 via single subcutaneous injection.

After receiving a single subcutaneous injection of 4.17 mg/kg TSL-4, results of the plasma concentration-time curve were shown in FIG. 22, measured results of the plasma concentration were shown in Table 9, and results of the pharmacokinetic parameters were shown in Table 10.

TABLE 9

Plasma concentration of rats after receiving a single subcutaneous injection of 4.17 mg/kg TSL-4 (unit: μg/mL)

| Time/h | Rat No. 1 | 2 | 3 | 4 | 5 | Mean |
|---|---|---|---|---|---|---|
| 0.00 | 0 | 0 | 0 | 0 | 0 | 0 |
| 0.50 | 0.00626 | 0.0985 | 0.131 | 0.0504 | 0.122 | 0.0818 |
| 1.00 | 0.0588 | 0.162 | 0.168 | 0.136 | 0.151 | 0.135 |
| 3.00 | 0.238 | 0.382 | 0.412 | 0.338 | 0.570 | 0.388 |
| 5.00 | 0.667 | 0.482 | 0.575 | 0.374 | 0.766 | 0.573 |
| 6.00 | 1.278 | 0.699 | 1.024 | 0.491 | 0.978 | 0.894 |
| 7.00 | 1.696 | 0.903 | 1.556 | 0.914 | 1.415 | 1.297 |
| 8.00 | 1.383 | 1.584 | 1.319 | 1.407 | 1.088 | 1.356 |
| 10.00 | 1.192 | 1.305 | 0.854 | 0.960 | 0.980 | 1.058 |
| 12.00 | 0.947 | 0.964 | 0.712 | 0.363 | 0.867 | 0.771 |
| 16.00 | 0.767 | 0.682 | 0.237 | 0.183 | 0.471 | 0.468 |
| 20.00 | 0.249 | 0.252 | 0.179 | 0.172 | 0.172 | 0.205 |
| 24.00 | 0.0638 | 0.0738 | 0.0533 | 0.155 | 0.155 | 0.100 |
| 28.00 | 0.0454 | 0.0406 | 0.0381 | 0.105 | 0.105 | 0.0667 |
| 41.00 | 0.0298 | 0.0288 | 0.0231 | 0.0954 | 0.0954 | 0.0545 |
| 53.00 | 0.0108 | 0.00740 | 0.0171 | 0.0669 | 0.0809 | 0.0366 |
| 65.00 | 0.008536 | 0.003139 | 0.0168 | 0.0440 | 0.044002 | 0.0233 |
| 77.00 | 0.005846 | 0.002666 | 0.0125 | 0.0181 | 0.018107 | 0.0114 |

Figure 23:
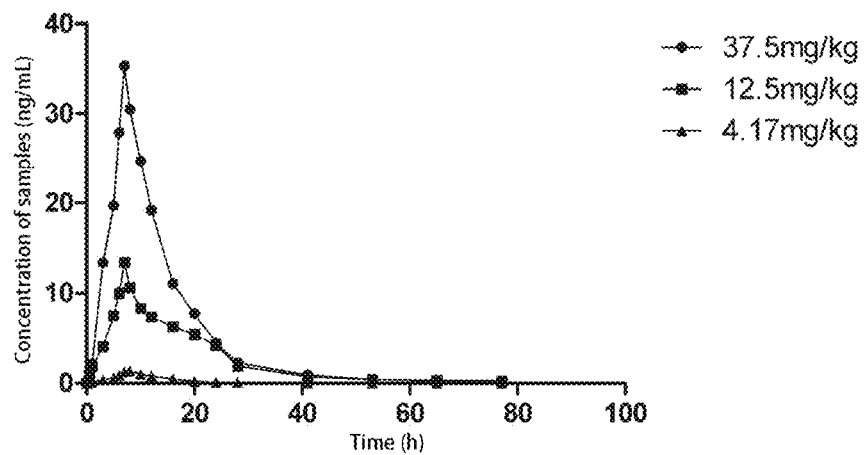
FIG. 23 shows a mean plasma concentration time curve after receiving different doses of TSL-4 via single subcutaneous injection in rats.
Figure 24:
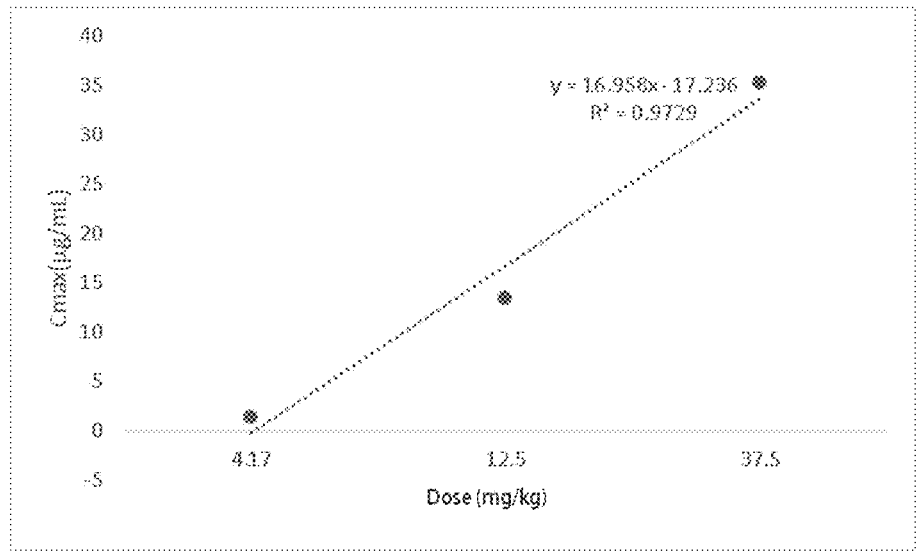
FIG. 24 shows a relation graph between TSL-4 peak concentration (Cmax) and dose administered.
Figure 25:
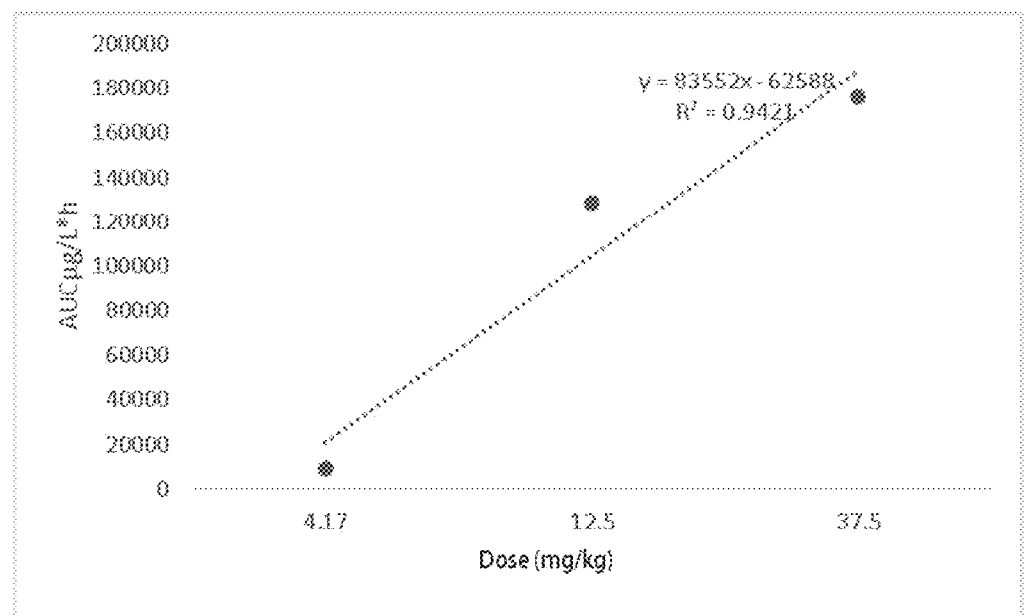
FIG. 25 shows a relation graph between AUC and dose administered.

NA means below the lower limit of detection
3.4 Comparison on pharmacokinetic parameters of SD rats after receiving a single subcutaneous injection of TSL-4 at different doses After receiving a single subcutaneous injection of TSL-4 at different doses, the mean plasma concentration-time curve of rats was shown in FIG. 23; the relation between TSL-4 peak concentration (Cmax) and dosage of administration in plasma was shown in FIG. 24; the relation between area (AUC) and dosage of administration was shown in FIG. 25; and comparison results of major pharmacokinetic parameters were shown in Table 10.

TABLE 10

Comparison results of major pharmacokinetic parameters (n = 6)

| Parameter | Single subcutaneous administration | | |
|---|---|---|---|
| | High-dose group (37.5 mg/kg) | Medium-dose group (12.5 mg/kg) | Low-dose group (4.17 mg/kg) |
| ka | 0.116 | 0.247 | 0.258 |
| α, ke | 0.197 | 0.149 | 0.090 |
| t½ka(h) | 3.079 | 3.249 | 2.265 |
| t½ke(h) | 34.355 | 32.321 | 30.710 |
| Vd/F(L/kg) | 4.967 | 3.177 | 4.200 |
| CL/F(L/h/kg) | 0.101 | 0.071 | 0.925 |
| AUC 0-77(μg/L*h) | 166338 | 116190.1 | 7055.774 |
| AUC 0-∞(μg/L*h) | 176110 | 128430.2 | 9006.668 |
| MRT 0-77(h) | 13.988 | 18.248 | 14.880 |
| MRT 0-∞(h) | 15.755 | 20.882 | 17.330 |
| Tmax(h) | 7 | 7 | 7.4 |
| Cmax(μg/L) | 37862.95 | 14045.39 | 1531.335 |

The above results indicated that after SD rats were subcutaneously injected high, medium and low doses (37.5 mg/kg, 12.5 mg/kg, 4.17 mg/kg) of TSL-4, $AUC_{0-\infty}$ in each dose group was 9006.668±3859.519, 147501.4±28351.84, 176110±39596.45 μg/L·h respectively, showing a good linear relation with the dosage of administration ($R^2$=0.9421); Cmax was 1.531±0.122, 14.045±3.182, 37.863±8.396 μg/mL respectively, showing a good linear relation with the dosage of administration ($R^2$=0.9729); absorption half-life $T_{1/2ka}$ was respectively: 2.824±0.697 h, 3.788±0.848 h, 4.478±0.223 h; the elimination half-life $T_{1/2ke}$ was 30.710±3.100 h, 32.321±4.935 h, 34.356±1.578 h respectively; and peak time $T_{max}$ was 7.4±0.55 h, 7±0.707 h, 7±0.707 h respectively. CL was 1.383±0.528 L/h/kg, 0.070759±0.0369 L/h/kg, 0.0569±0.0336 L/h/kg respectively.

After receiving a single subcutaneous injection of TSL-4 at high, medium and low doses (37.5 mg/kg, 12.5 mg/kg, 4.17 mg/kg), TSL-4 showed a first-order kinetic process in SD rats, consistent with linear pharmacokinetic characteristics, and the C-T curve was consistent with a two-compartment model. The Time of TSL-4 at high, medium and low-dose groups was relatively longer, indicating that TSL-4 was more slowly eliminated in SD rats.

Embodiment 13: TSL-4 Tissue Distribution

Objectives:
(1) In vivo PET/CT scanning may be used to study the distribution for the ankle joints and rest tissues of the whole body of arthritis model rats after receiving a single subcutaneous injection of $^{89}$Zr-HM-3.
(2) In-vitro tissue gamma counting may be used to study the distribution for the ankle joints and rest tissues of the whole body of arthritis model rats after receiving a single subcutaneous injection of $^{89}$Zr-HM-3.
(3) In vivo PET/CT scanning may be used to study the distribution for the ankle joints and rest tissues of the whole body of arthritis model rats after receiving a single injection of $^{89}$Zr-FIM-3 in ankle joint cavities.

Experimental Method:
Modeling method of type-II CIA model rats: 3 mL incomplete Freund's adjuvant (Chondrex Inc, batch No. 160111) and 3 mL type-II collagen (Chondrex Inc, Lot No. 160346) were emulsified on ice with a homogenizer until the emulsion was undispersed after dripped into water. Intracutaneous injections (2 points, 0.15 mL emulsion for each point) were conducted on the tails of Wistar rats (female, 130-150 g, certification No. 2015000526387 and 2015000527320, Shanghai SLAC Laboratory Animal Co., Ltd), and each rat was injected 0.3 mL emulsion to form local bulges on the skin surface. About 2 weeks later, the morbidity of rats was observed and scored.

TABLE 11

Scoring criteria of model morbidity

| Scoring | Observation standards |
|---|---|
| 0 | No obvious redness and swelling |
| 1 | Erythema and mild swelling in tarsal or ankle joints only |
| 2 | Erythema and mild swelling extended to tarsal bones from ankle joints |
| 3 | Erythema and mild swelling extended metatarsal joints from ankle joints |
| 4 | Erythema and serious swelling in ankle joints, paws and toes |

The arthritis model rats received standard CT/PET body scanning by a small-animal PET/CT at 1 h, 12 h, 24 h, 48 h, 120 h and 192 h respectively after subcutaneously injected $^{89}$Zr-HM-3 and free $^{89}$Zr; the arthritis model rats received standard CT/PET body scanning by the small-animal PET/CT at 1 h, 24 h, 48 h, 120 h, 192 h and 360 h respectively after injected $^{89}$Zr-HM-3 via left ankle cavity. Combined with CT images, radioactivity intakes SUV and % ID/g were obtained by sketching the heart, liver, lung, kidney, brain, ankle joint cavity, vertebra and muscle of arthritis model rats.

The arthritis model rats received standard CT/PET body scanning at 48 h and 120 h firstly after subcutaneously injected $^{89}$Zr-HM-3; then fluid of ankle joint cavity, whole blood, heart, liver, spleen, lung, kidney, stomach, small intestine (near pylorus), pancreas, vertebra, muscle, gonad and brain tissue were collected in a micro-perfusion manner, and placed into a radioimmunoassay tube after weighed, thus detecting radioactive uptake values in joint cavity fluid, whole blood and tissues by gamma counting. γ counting results served to calculate the radioactivity intake % ID/g in blood and tissues of arthritis model rats

TABLE 12

Animal grouping, dosage of administration and sampling plan

| Group | Objective | n | Subject | Administration route | Dosage of administration | Radioactive dosage | Time point |
|---|---|---|---|---|---|---|---|
| 1 | Tissue distribution | 3 female arthritis model rats | $^{89}$Zr-HM-3 | Subcutaneous injection | About 12.5 mg/kg | 300 ± 100 μCi/pcs. | Static scanning$^a$ 1 h, 12 h, 24 h, 48 h, 120 h, 192 h after administration |
| 2 | Tissue Distribution | 3 female arthritis model rats | $^{89}$Zr-HM-3 | Subcutaneous injection | About 12.5 mg/kg | 300 ± 100 μCi/pcs. | Static scanning 48 h after administration, The intra-articular fluid, whole blood and tissue were collected for gamma counting$^b$ |
| 3 | Tissue distribution | 3 female arthritis model rats | $^{89}$Zr-HM-3 | Subcutaneous injection | About 12.5 mg/kg | 300 ± 100 μCi/pcs. | Static scanning, collection of joint cavity fluid and whole blood, as well as gamma counting$^b$ 120 h after administration |
| 4 | Tissue distribution | 3 female arthritis model rats | $^{89}$Zr-HM-3 | Injection via ankle joint cavity | NA | 50 ± 20 μCi/pcs. | Static scanning$^a$ 1 h, 24 h, 48 h, 120 h, 192 h, 360 h after administration |
| 5 | Tissue distribution | 1 female arthritis model rat | $^{89}$Zr | Subcutaneous injection | NA | 300 ± 100 μCi/pcs. | Static scanning$^a$ 1 h, 24 h, 24 h, 48 h, 120 h, 192 h after administration |

$^a$Rats received multiple-bed body scanning (PET scanning for 10 min each one) 1 h, 12 h, 24 h, 48 h later after administration, multiple-bed body scanning (PET scanning for 15 min each one) 120 h and 192 h later as well as multiple-bed body scanning (PET scanning for 20 min each one) 360 h later.
$^b$Tissue collection included the collection 12 organs, namely, heart, liver, spleen, lung, kidney, stomach, small intestine (near pylorus), pancreas, vertebra, muscle, gonad and brain.
c: Arthritis model rats were anesthetized 10 min before scanning. The specific anesthesia was to induce anesthesia of SD rats by 3-5% isoflurane and 0.5-2 L/min air, and to maintain the anesthesia by 1-3% isoflurane and 0.5-1 L/min air. During the experiment, detailed information, such as animal weight, initial injection dose and measurement time, injection time, residual dose and measurement time, and scanning time of small-animal PET/CT at different time points were accurately recorded on the original record form.

Experimental Results

1. Subject Labeling

TABLE 13

Experimental results of $^{89}$Zr-HM-3 quality control

| Lot No. | 16121501 | 16121502 | L17011101 |
|---|---|---|---|
| Character | Clear and | Clear and | Clear and |
| PH | 7.2 | 7.2 | 7.2 |
| Radio-chemically purity(%) | 90.40 | 90.40 | 92.71 |
| Chemical purity (%) | 98.37 | 98.37 | 98.09 |

TABLE 14

Result-1 of $^{89}$Zr-HM-3 in vitro stability test

| Lot No. | 1 h | 4 h | 8 h | 9 h |
|---|---|---|---|---|
| 16121501 | 90.40% | 90.01% | 90.74% | 90.11% |
| 16121502 | 90.40% | 90.01% | 90.74% | 90.11% |

TABLE 15

Result-2 of 89Zr-HM-3 in vitro stability test

| Lot No. | 1 h | 4 h | 7 h |
|---|---|---|---|
| L17011101 | 91.03% | 90.73% | 90.89% |

As shown in Tables 13-15, $^{89}$Zr-HM-3 quality control of Lot No. 16121501, 16121502 and L17011101 conformed to experimental requirements.

2. PET/CT Scanning

TABLE 16

PET/CT scanning radioactivity intake % ID/g of arthritis model rats after injected $^{89}$Zr-HM-3 subcutaneously at 6 time points

| Time point | Heart | Lung | Liver | Kidney | Brain | Left ankle cavity | Right ankle cavity | Vertebra | Muscle |
|---|---|---|---|---|---|---|---|---|---|
| 1 h | 0.01 ± 0.01 | 0.04 ± 0.06 | 0.00 ± 0.00 | 0.04 ± 0.01 | 0.00 ± 0.00 | 0.01 ± 0.00 | 0.01 ± 0.00 | 0.01 ± 0.00 | 0.01 ± 0.01 |
| 12 h | 0.90 ± 0.04 | 0.34 ± 0.08 | 0.41 ± 0.03 | 0.66 ± 0.04 | 0.04 ± 0.01 | 0.28 ± 0.04 | 0.27 ± 0.10 | 0.17 ± 0.02 | 0.05 ± 0.01 |
| 24 h | 1.02 ± 0.12 | 0.40 ± 0.11 | 0.58 ± 0.07 | 1.28 ± 0.05 | 0.08 ± 0.01 | 0.5 ± 0.13 | 0.50 ± 0.21 | 0.29 ± 0.03 | 0.11 ± 0.02 |
| 48 h | 1.00 ± 0.03 | 0.50 ± 0.09 | 0.62 ± 0.04 | 2.08 ± 0.19 | 0.05 ± 0.02 | 0.52 ± 0.09 | 0.73 ± 0.42 | 0.4 ± 0.02 | 0.13 ± 0.02 |
| 120 h | 0.59 ± 0.07 | 0.27 ± 0.07 | 0.69 ± 0.07 | 3.89 ± 0.08 | 0.06 ± 0.02 | 0.51 ± 0.11 | 0.57 ± 0.38 | 0.74 ± 0.19 | 0.14 ± 0.04 |
| 192 h | 0.39 ± 0.07 | 0.22 ± 0.01 | 1.02 ± 0.27 | 4.42 ± 0.11 | 0.05 ± 0.01 | 0.47 ± 0.16 | 0.53 ± 0.31 | 1.02 ± 0.05 | 0.08 ± 0.01 |

As shown in Table 16, kidney radioactivity intake % ID/g of arthritis model rats was up to the maximum (0.04±0.01) 1 h after receiving the subcutaneous injection of $^{89}$Zr-HM-3, followed by lung>left ankle cavity=right ankle cavity=vertebra>heart=muscle>liver; at 12 h, the heart radioactivity intake % ID/g was up to the maximum (0.90±0.04), followed by kidney>liver>lung>left ankle cavity>right ankle cavity>vertebra>muscle; at 24 h, the kidney radioactivity intake % ID/g was up to the maximum (1.28±0.05), followed by heart>liver>left ankle cavity>right ankle cavity>lung>vertebra>muscle; at 48 h, the kidney radioactivity intake % ID/g was up to the maximum (2.08±0.19), followed by heart>right ankle cavity>liver>left ankle cavity>lung>vertebra>muscle; at 120 h, the kidney radioactivity intake % ID/g was up to the maximum (3.89±0.08), followed by vertebra>liver>heart>right ankle cavity>left ankle cavity>lung>muscle; at 192 h, the kidney radioactivity intake % ID/g was up to the maximum (4.42±0.11), followed by vertebra>liver>right ankle cavity>left ankle cavity>heart>lung>muscle.

Figure 26:
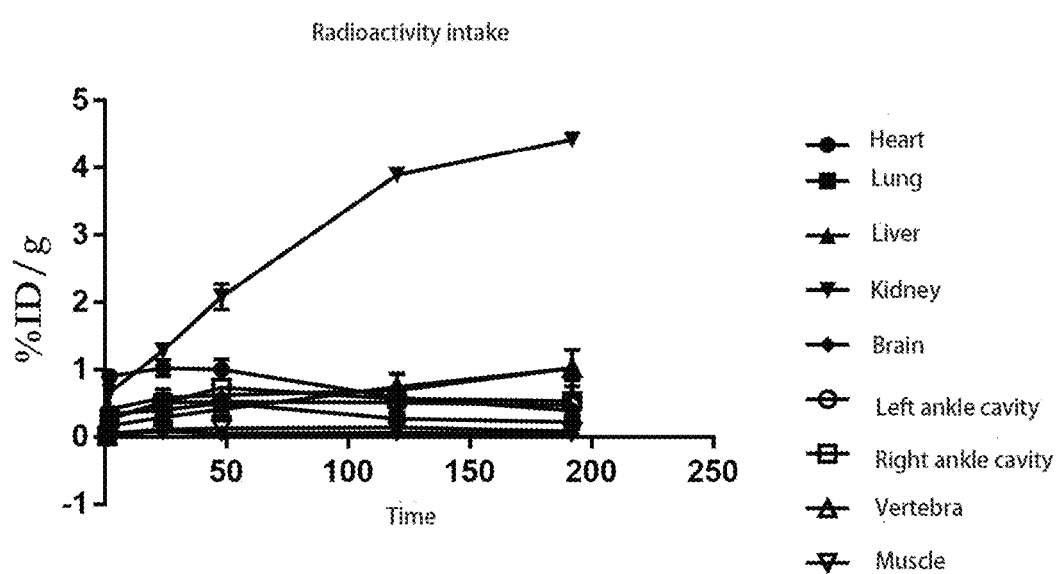
FIG. 26 shows a PET/CT scanning radioactivity uptake image of arthritis model rats after receiving 89Zr-HM-3 via subcutaneous injection at 6 time points.

After arthritis model rats received the subcutaneous injection of $^{89}$Zr-HM-3, the radioactivity intake % ID/g of heart was up to the minimum (0.01±0.01) at 1 h and up to the maximum (1.02±0.12) at 24 h, afterwards gradually decreased with time; the radioactivity intake % ID/g of lung, left ankle cavity and right ankle cavity was up to the minimum at 1 h, being 0.04±0.06, 0.01±0.00 and 0.01±0.00 respectively, and up to the maximum at 48 h, namely, 0.50±0.09, 0.52±0.09 and 0.73±0.42 respectively, afterwards, it gradually decreased with time; the radioactivity intake % ID/g of liver, kidney and vertebra was up to the minimum at 1 h, namely, 0.00±0.00, 0.04±0.01 and 0.01±0.00 respectively, and gradually increased with time, being up to the maximum at 192 h, namely, 1.02±0.27, 4.42±0.11, 1.02±0.05 respectively; the radioactivity intake % ID/g muscle was up to the minimum (0.01±0.01) at 1 h and up to the maximum (0.14±0.04) at 120 h. Specific results were shown in FIG. 26.

TABLE 17

PET/CT scanning radioactivity intake % ID/g of arthritis model rats after receiving the subcutaneous injection of $^{89}$Zr-HM-3 at 48 h and 120 h respectively

| Time point | Heart | Lung | Liver | Kidney | Brain | Left ankle cavity | Right ankle cavity | Vertebra | Muscle |
|---|---|---|---|---|---|---|---|---|---|
| 48 h | 1.12 ± 0.06 | 0.61 ± 0.05 | 0.81 ± 0.04 | 2.60 ± 0.09 | 0.12 ± 0.02 | 0.42 ± 0.11 | 0.38 ± 0.07 | 0.46 ± 0.01 | 0.22 ± 0.03 |
| 120 h | 0.67 ± 0.02 | 0.60 ± 0.35 | 0.66 ± 0.15 | 3.72 ± 0.70 | 0.12 ± 0.03 | 0.50 ± 0.32 | 0.39 ± 0.09 | 0.65 ± 0.13 | 0.20 ± 0.05 |

Figure 27:
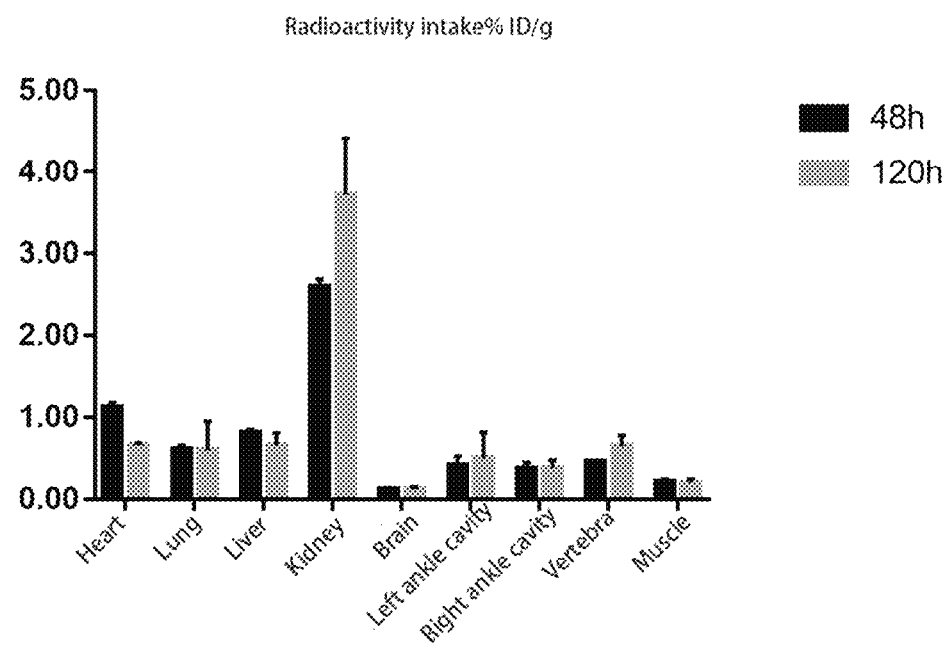
FIG. 27 shows a scanning radioactivity uptake image of arthritis model rats after receiving 89Zr-HM-3 via subcutaneous injection at 48 h and 120 h.

As shown in Table 17, PET/CT scanning was performed to arthritis model rats after receiving the subcutaneous injection of $^{89}$Zr-HM-3 at 48 h, and then tissues were collected for gamma counting to obtain the following results: the radioactivity intake % ID/g of kidney was up to the maximum (2.60±0.09), followed by heart>liver>lung>vertebra>left ankle cavity>right ankle cavity>muscle; PET/CT scanning was performed to arthritis model rats after receiving the subcutaneous injection of $^{89}$Zr-HM-3 at 120 h, and then tissues were collected for gamma counting to obtain the following results: the radioactivity intake % ID/g of kidney was up to the maximum (3.72±0.70), followed by heart>liver>vertebra>lung>left ankle cavity>right ankle cavity>muscle. Specific results were shown in FIG. 27.

TABLE 18

Radioactivity intake % ID/g of arthritis model rats after injected $^{89}$Zr-HM-3 in left ankle cavity at 6 time points

| Time point | Heart | Lung | Liver | Kidney | Brain | Left ankle cavity | Right ankle cavity | Vertebra | Muscle |
|---|---|---|---|---|---|---|---|---|---|
| 1 h | 0.59 ± 0.94 | 0.25 ± 0.42 | 0.40 ± 0.65 | 0.39 ± 0.57 | 0.02 ± 0.04 | 42.20 ± 17.33 | 0.11 ± 0.18 | 0.10 ± 0.17 | 0.06 ± 0.10 |
| 24 h | 1.15 ± 0.14 | 0.71 ± 0.39 | 0.88 ± 0.21 | 1.37 ± 0.42 | 0.12 ± 0.03 | 6.50 ± 3.06 | 0.49 ± 0.31 | 0.38 ± 0.05 | 0.18 ± 0.01 |
| 48 h | 0.77 ± 0.21 | 0.48 ± 0.12 | 0.66 ± 0.16 | 1.67 ± 0.57 | 0.05 ± 0.01 | 2.75 ± 0.64 | 0.73 ± 0.05 | 0.47 ± 0.11 | 0.19 ± 0.03 |
| 120 h | 0.43 ± 0.12 | 0.34 ± 0.05 | 0.61 ± 0.29 | 2.78 ± 0.44 | 0.06 ± 0.04 | 1.90 ± 0.26 | 0.56 ± 0.25 | 0.44 ± 0.14 | 0.12 ± 0.01 |
| 192 h | 0.35 ± 0.06 | 0.25 ± 0.10 | 0.74 ± 0.54 | 3.04 ± 0.52 | 0.07 ± 0.06 | 1.72 ± 0.29 | 0.53 ± 0.27 | 0.66 ± 0.18 | 0.09 ± 0.02 |
| 360 h | 0.39 ± 0.27 | 0.11 ± 0.04 | 0.81 ± 0.05 | 2.70 ± 0.54 | 0.08 ± 0.04 | 1.69 ± 0.29 | 0.42 ± 0.42 | 0.82 ± 0.13 | 0.09 ± 0.07 |

As shown in Table 18, the radioactivity intake % ID/g of left ankle cavity of arthritis model rats was up to the maximum (42.20±17.33) 1 h later after injected 89 Zr-HM-3 in left ankle cavity, followed by heart>liver>kidney>lung>right ankle cavity>vertebra>muscle; at 24 h, the radioactivity intake % ID/g of left ankle cavity was up to the maximum (6.50±3.06), followed by kidney>heart>liver>lung>right ankle cavity>vertebra>muscle; at 48 h, the radioactivity intake % ID/g of left ankle cavity was up to the maximum (2.75±0.64), followed by kidney>heart>right ankle cavity>liver>lung>vertebra>muscle; at 120 h, the radioactivity intake % ID/g of kidney was up to the maximum (2.78±0.44), followed by left ankle cavity>liver>right ankle cavity>vertebra>heart>lung>muscle; at 192 h, the radioactivity intake % ID/g of kidney was up to the maximum (3.04±0.52), followed by left ankle cavity>liver>vertebra>right ankle cavity>heart>lung>muscle; at 360 h, the radioactivity intake % ID/g of kidney was up to the maximum (2.70±0.54), followed by left ankle cavity>vertebra>liver>right ankle cavity>heart>muscle.

Figure 28:
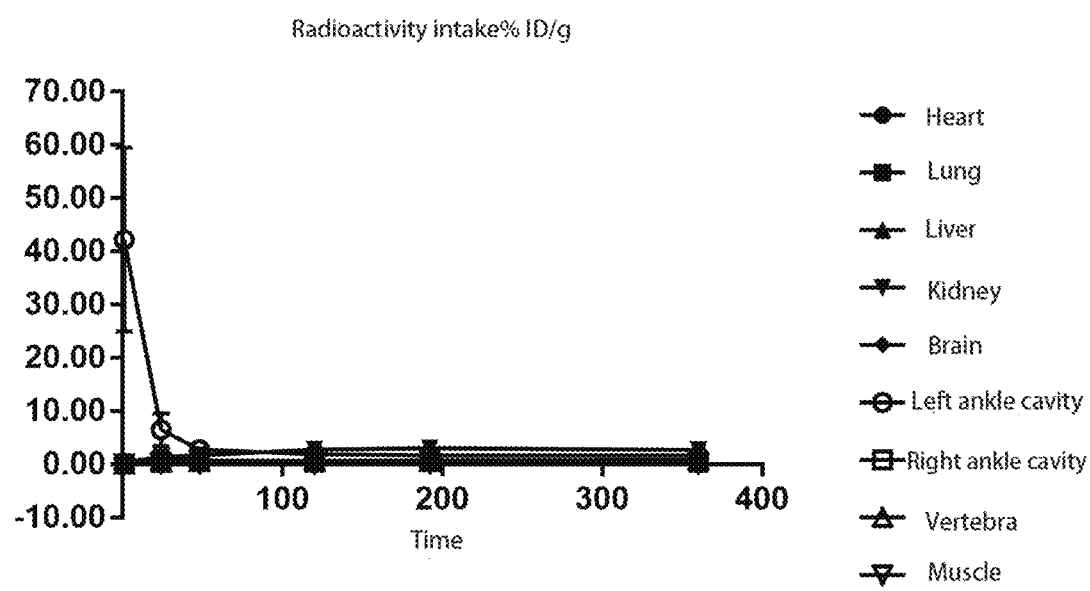
FIG. 28 shows a radioactivity uptake image of arthritis model rats after receiving 89Zr-HM-3 on left ankle joints via subcutaneous injection at 6 time points.

After arthritis model rats were injected with 89Zr-HM-3 into left ankle cavity, the radioactivity intake % ID/g of heart and lung was 0.59±0.94 and 0.25±0.42 at 1 h respectively, up to the maximum at 24 h, being 1.15±0.14 and 0.71±0.39 respectively, afterwards gradually decreased with time; the radioactivity intake % ID/g of left ankle cavity was up to the maximum at 1 h (42.20±17.33), then decreased gradually with the time and up to the minimum at 360 h (1.69±0.29); the radioactivity intake % ID/g of right ankle cavity and muscle was up to the minimum at 1 h, being 0.11±0.18 and 0.06±0.10 respectively, and up to the maximum at 48 h, being 0.73±0.05 and 0.19±0.03 respectively, afterwards gradually decreased with time; the radioactivity intake % ID/g of liver was up to the minimum (0.40±0.65) at 1 h and up to the maximum (0.88±0.21) at 24 h, afterwards slightly decreased with time; the radioactivity intake % ID/g of kidney was up to the minimum (0.39±0.57) at 1 h and up to the maximum (3.04±0.52) at 192 h, afterwards gradually decreased with time; the radioactivity intake % ID/g of vertebra was up to the minimum (0.10±0.17) at 1 h and gradually increased with time, being up to the maximum (0.82±0.13) at 360 h. Specific results were shown in FIG. 28.

TABLE 19

Radioactivity intake % ID/g of arthritis model rats after receiving the subcutaneous injection of free $^{89}$Zr at 6 time points

| Time point | Heart | Lung | Liver | Kidney | Brain | Left ankle cavity | Right ankle cavity | Vertebra | Muscle |
|---|---|---|---|---|---|---|---|---|---|
| 1 h | 1.08 | 0.45 | 0.52 | 0.60 | 0.07 | 0.06 | 0.16 | 0.52 | 0.12 |
| 12 h | 1.62 | 0.85 | 0.86 | 0.89 | 0.17 | 0.25 | 0.65 | 2.43 | 0.31 |
| 24 h | 1.18 | 0.56 | 0.77 | 0.75 | 0.19 | 0.27 | 0.92 | 3.64 | 0.23 |
| 48 h | 0.46 | 0.41 | 0.76 | 0.79 | 0.10 | 0.34 | 1.13 | 4.05 | 0.17 |
| 120 h | 0.17 | 0.14 | 0.57 | 0.73 | 0.23 | 0.34 | 1.25 | 5.35 | 0.16 |
| 192 h | 0.11 | 0.10 | 0.44 | 0.55 | 0.13 | 0.32 | 1.05 | 5.38 | 0.20 |

As shown in Table 19, the heart radioactivity intake % ID/g was up to the maximum (1.08) at 2 h, followed by kidney>liver=vertebra>lung>right ankle cavity>muscle>left ankle cavity; the vertebra radioactivity intake % ID/g was up to the maximum at 12 h, 24 h, 48 h, 120 h, 192 h, being 2.43, 3.64, 4.05, 5.35, 5.38 respectively, which was much higher than other tissues at the same time point.

ity intake of heart in arthritis model rats after receiving the subcutaneous injection of 89Zr-HM-3 and injection into left ankle cavity was up to the maximum at 24 h, and then gradually decreased with time; the radioactivity intake of ankle cavity (non-administrated site) was up to the maximum at 48 h, and then decreased gradually with time. The radioactivity intake of kidney and liver gradually increased or kept a higher level with time.

TABLE 21

Half-life (h) in the heart of arthritis model rats after receiving the subcutaneous injection of $^{89}$Zr-HM-3 and injection into left ankle cavity respectively

| Experiment No. | G1-F-01 | G1-F-02 | G1-F-03 | G4-F-01 | G4-F-02 | G4-F-03 |
|---|---|---|---|---|---|---|
| $T_{1/2}$ | 153.17 | 89.21 | 119.66 | 56.84 | 127.11 | 111.09 |

3. Gamma Counting

TABLE 20

Tissue radioactivity intake % ID/g of arthritis model rats after receiving the subcutaneous injection of $^{89}$Zr-HM-3 at 48 h and 120 h respectively

| Tissue | Time point | |
|---|---|---|
| | 48 h | 120 h |
| Whole blood | 2.32 ± 0.20 | 1.63 ± 0.21 |
| Heart | 0.41 ± 0.01 | 0.31 ± 0.02 |
| Liver | 0.58 ± 0.04 | 0.63 ± 0.08 |
| Spleen | 0.44 ± 0.05 | 0.67 ± 0.11 |
| Lung | 0.80 ± 0.08 | 0.98 ± 0.42 |
| Kidney | 0.79 ± 0.21 | 2.16 ± 1.94 |
| Stomach | 0.27 ± 0.03 | 0.26 ± 0.06 |
| Intestines | 0.38 ± 0.01 | 0.62 ± 0.18 |
| Pancreas | 0.31 ± 0.02 | 0.36 ± 0.12 |
| Vertebra | 0.37 ± 0.03 | 0.50 ± 0.05 |
| Muscle | 0.17 ± 0.02 | 0.17 ± 0.05 |
| Gonad | 0.73 ± 0.09 | 0.69 ± 0.17 |
| Brain | 0.03 ± 0.01 | 0.03 ± 0.01 |
| Joint cavity fluid | 0.34 ± 0.18 | 0.65 ± 0.32 |

Figure 29:
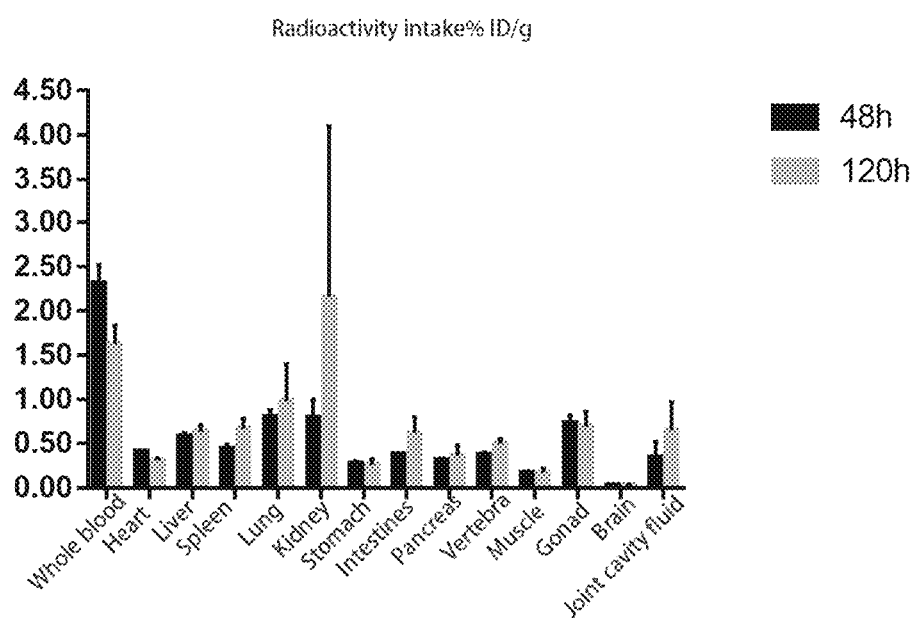
FIG. 29 shows a tissue radioactivity image of arthritis model rats after receiving 89Zr-HM-3 via subcutaneous injection collected at 48 h and 120 h.

As shown in Table 20, whole blood and tissues of arthritis model rats were collected at 48 h after receiving the subcutaneous injection of $^{89}$Zr-HM-3, the radioactivity intake % ID/g of whole blood was up to the maximum (2.32±0.20), followed by lung>kidney>gonad>liver>spleen>heart>intestines>vertebra>joint cavity fluid>pancreas>stomach>muscle; whole blood and tissues of experimental animals were collected at 120 h after receiving the subcutaneous injection of $^{89}$Zr-HM-3, the radioactivity intake % ID/g of kidney was up to the maximum (2.16±1.94), followed by whole blood>lung>gonad>spleen>joint cavity fluid>liver>intestine>vertebra>pancreas>heart>stomach>muscle. Specific results were shown in FIG. 29.

4. Conclusion

The results showed that the free 89Zr was mainly distributed in bones 12 h after administration, the 89Zr radioactivity intake % ID/g in bones was much higher than other tissues at 12 h, 24 h, 48 h, 120 h and 196 h, indicating that 89Zr-HM-3 could basically stably exist in arthritis model rats; and the radioactivity intake % ID/g in brain was always very low at all time points, and close to or lower than that in muscle at the same time points, indicating that 89Zr-HM-3 crossed blood-brain barrier difficulty. The radioactiv- As shown in Table 21, analyzed by a DAS3.2.8 non-compartment model, the half-life of arthritis model rats subcutaneously injected 89Zr-HM-3 was 120.68±31.99 h; the half-life of arthritis model rats injected 89Zr-HM-3 in left ankle cavity was 98.35±36.83 h.

Embodiment 14 Protective Effect of HM-3 Fusion Protein TSL-4 on Bone Tissue Cells Injured by Hydrogen Peroxide 1. Experimental Method All cell experiments should be operated in a sterile biosafety cabinet, and the operating platform should be sterilized (UV irradiation and 75% medical alcohol), moreover, waste cell liquor should be collected in a waste liquor barrel, furthermore, the waste transfer pipette and pipette tip used in the experiment should be put into an autoclaved bag for autoclaved sterilization.

Chondrocytes were cultured in a T75 flask for 3-4 days. When the degree of fusion reached 80%, the original culture medium was removed, and sterile PBS was added to clean the cells for 2-3 times, then a proper amount of digestive juice was added, and a fresh culture medium was added after the cells were detached. Cells were centrifuged to remove the cell sap containing the digestive juice, and a proper amount of fresh culture medium was added to be prepared into a cell suspension with appropriate concentration for cell subculture or cell experiments. Cell subculture began from generation P1 and ended till generation P5, and there were cryopreserved cells in each generation. Cells were used for the experiment when subcultured to P2-P5.

According to the inoculum size of 200 μL/well, the cell suspension with the density of $2.5*10^4$/mL was inoculated onto a 96-well cell culture plate, and 3 groups were prepared in total, one for control group, and the other two groups were stimulated by hydrogen peroxide. A cell-free medium was prepared as a blank group. There were 4-5 sub-wells prepared in each group. The cell culture plate was put to an incubator for incubation for 24 hours. The culture medium was replaced to different experimental groups in the following day with a dose volume of 100 μl and incubated for 24 or 48 hours respectively.

At the end of incubation according to the experimental plan, 10 μL of 5 mg/ml MTT was added to each experimental group based upon 1/10 of the cell culture volume, so that the cells were incubated with MTT in the incubator for 4 hours. Afterwards, supernatant was carefully discarded, and 200 μL of dimethyl sulfoxide (DMSO) was added for mixing well, then the absorbance was measured on a microplate reader at a test wavelength of 570 nm. Calculating formula of relative cell activity ratio (%): a mean value of the absorbance (per well) in the experimental group/the absorbance in the control group multiplies by 100%. All experimental groups were expressed as mean±standard deviation ($\bar{X}$±SD). The difference between each group was analyzed by Prism 7.0, and tested by one-way ANOVA. *P<0.05 means statistical difference, P<0.01 means significant statistical difference, and P<0.001 means extremely significant statistical difference.

2. Main Experimental Materials (1) Rat chondrocyte, Art. No.: RAT-iCell-s003, iCell Bioscience.
(2) Molding agent: Medical LIRCON®3% hydrogen peroxide disinfectant solution ($H_2O_2$, hydrogen peroxide) (0.9 M), Lot No.: 170928, LIRCON.
(3) Cell culture medium system: primary chondrocyte basal medium+10% fetal bovine serum (FBS)+1% cell culture additives+1% penicillin/streptomycin (PS) (Art. No.: PriMed-iCell-020, iCell Bioscience)
(4) Related reagents of cell subculture: PBS sterile saline solution (pH=7.2) (Art. No.: C0221A, Beyotime Biotechnology); digestive juice: 0.02% EDTA+0.25% trypsin solution (Art. No.: 25200056, Thermo Fischer Scientific Inc.); common sterile heating-inactivated serum (Art. No.: 10100147, Gibco).
(5) MTT-related reagents: MTT (thiazolyl blue) (Art. No.: M2128-500 mg, Sigma); DMSO (D5879-500 ml, Sigma).

3. Experimental Results

Experiment 1 $H_2O_2$ Molding Time and Dosage Optimization

The experimental concentration of hydrogen peroxide ranged within 0.01, 0.1, 0.5, 1, 10 mM. In order to determine the $H_2O_2$ molding time and dosage, three molding time points at 24 hours, 48 hours and 72 hours were selected, and two detection wells were prepared in total for each dosage of hydrogen peroxide.

TABLE 22

MTT test values under different molding time and dosages of $H_2O_2$

| Dosage (mM) of chondrocytes injured by $H_2O_2$ | 24 h | 48 h | 72 h |
|---|---|---|---|
| 0 | 2.35 | 2.24 | 1.94 |
| 0.01 | 2.51 | 2.1 | 1.99 |
| 0.1 | 2.29 | 2.08 | 1.92 |
| 1 | 1.28 | 1.47 | 0.81 |
| 10 | 0.06 | 0.56 | −0.07 |

The above results indicated that after simulated by hydrogen peroxide, chondrocytes had similar changes in cell viability at 24, 48 and 72 hours; cell viability decreased with the increase of $H_2O_2$ concentration. Moreover, compared with the control group (0 mM $H_2O_2$), the cell viability under the concentration of 1 and 10 mM significantly dropped at the three time points, therefore, 24 h served as $H_2O_2$ molding time. In addition, the dosage of hydrogen peroxide was optimal when the relative activity to the control group was about 0.5. The results showed that the dosage of hydrogen peroxide should be selected within 0.1-1 mM.

Experiment 2 Optimization for the Dosage of HM-3 Fusion Protein TSL-4

The concentration of TSL-4 should be selected within 0.1, 0.3, 1, 3, 9, 27 μM.

To determine whether TSL-4 influenced the viability of chondrocytes, 3 incubation time points at 24, 48 and 72 hours were selected, and two detection wells were prepared for each dosage of TSL-4 solution in total.

TABLE 23

MTT test values under different administration time and dosages of TSL-4

| TSL-4 dosage of administration (μM) | 24 h | 48 h | 72 h |
|---|---|---|---|
| 0 | 1.43 | 1.70 | 1.51 |
| 1 | 1.59 | 1.43 | 1.61 |
| 3 | 1.67 | 1.43 | 1.52 |
| 9 | 1.72 | 1.51 | 1.57 |
| 27 | 1.45 | 1.30 | 1.31 |

The above results indicated that TSL-4 had no significant influence on cell viability at 24, 48, and 72 hours, and there was no significant difference between each dosage of TSL-4 and the control group (0 μM TSL-4). Thus, 24 hours was selected as the TSL-4 administration time. However, there was no difference to TSL-4 among 1-27 μM dosages, so the effect of low-dose TSL-4 on cell viability should be tested again.

TABLE 24

MTT test values 24 hours later after administrating the low-dose TSL-4

| TSL-4 dosage of administration (μM) | 24 h |
|---|---|
| 0 | 1.23 |
| 0.1 | 1.26 |
| 0.3 | 1.2 |
| 1 | 1.15 |
| 3 | 1.08 |

The above results indicated that TSL-4 had no significant difference to the influence on cell viability among 0.1-3 μM.

In early experiment, the TSL-4 at each concentration had no effect on cell viability, therefore, it was diluted to 0.23 μM from 29.3 μM according to a dilution ratio of 1:5 based upon the concentration (293 μM) of the primary TSL-4 solution.

TABLE 25

MTT test values 24 hours after administrating the recommended dosage of TSL-4

| TSL-4 dosage of administration (μM) | 24 h |
|---|---|
| 0 | 1.68 |
| 0.23 | 1.59 |
| 1.17 | 1.4 |
| 5.86 | 1.39 |
| 29.3 | 1.24 |

Similarly, there was no significant change in cell viability after the TSL-4 at various concentrations (0.23-29.3 μM) and chondrocytes were cultured for 24 h, therefore, 0.23, 1.17, 5.86, 29.3 μM were selected as the dosing concentration of TSL-4 in the subsequent experiments.

Experiment 3 Detection on the Protective Effect of TSL-4 on Chondrocytes Injured by Hydrogen Peroxide In order to detect the protective effect of TSL-4 on chondrocytes injured by hydrogen peroxide, the experiment was divided into three groups control group (no hydrogen peroxide and TSL-4, only adding fresh culture medium), hydrogen peroxide modeling group (only adding hydrogen peroxide cell culture medium containing different concentrations) and TSL-4 administration group (containing hydrogen peroxide). In order to detect the protective effect of TSL-4 on chondrocytes injured by hydrogen peroxide, TSL-4 and hydrogen peroxide were cultured with chondrocytes for 24 hours. The dosage of hydrogen peroxide was selected within 0.1, 0.25, 0.5 and 1 mM; the TSL-4 dosage was 0.23, 1.17, 5.86, 29.3

In the presence of different doses of $H_2O_2$, TSL-4 at proper concentration and chondrocytes were cultured for 24 h, and the relative cell viability in each administration group (relative absorbance percentage to the control group) was expressed as the following $\overline{X} \pm SD$.

TABLE 26

Effect of hydrogen peroxide at different concentration and TSL-4 at different dosages on the viability of chondrocytes

| TSL-4 dosage of administration (μM) | Concentration of molding agent $H_2O_2$ (mM) | | | |
| --- | --- | --- | --- | --- |
| | 0.1 | 0.25 | 0.5 | 1 |
| 0 | 106.87 ± 9.52 | 70.96 ± 11.61 | 1.68 ± 0.82 | 3.57 ± 0.60 |
| 0.23 | 84.23 ± 20.42*** | 71.42 ± 6.74 | 3.17 ± 1.45 | 0.89 ± 0.32 |
| 1.17 | 100.01 ± 5.02 | 85.11 ± 8.08* | 16.56 ± 5.91* | 1.14 ± 1.07 |
| 5.86 | 102.36 ± 9.75 | 86.35 ± 4.20* | 10.27 ± 7.08 | 1.21 ± 0.70 |
| 29.3 | 76.46 ± 5.45**** | 59.72 ± 3.49 | 3.87 ± 6.00 | 0.43 ± 0.53 |

The above results indicated that 1.17 or 5.86 μM TSL-4 may significantly improve the viability of chondrocytes injured by hydrogen peroxide at the concentration of 0.25 and 0.5 mM $H_2O_2$; in addition, simulated by 0.1 mM $H_2O_2$, 0.23 and 29.3 μM TSL-4 played an significant role on cell viability;
*P < 0.05;
**P < 0.01;
***P < 0.001;
****P < 0.0001.

In Experiment 1 of Embodiment 14, the optimal molding concentration of hydrogen peroxide was measured within 0.1 and 1 mM. In this experiment, the cell viability ratio (%) decreased to about 5% when the concentration of hydrogen peroxide was 0.5 mM and 1 mM, which indicated that $H_2O_2$ molding was unstable, easy to cause a result difference. The result difference may be resulted from the poor oxidation resistance of chondrocytes caused by the difference in the number of chondrocyte subculture (chondrocytes were subcultured to P4 in this experiment). It can be seen from a literature that chondrocytes are susceptible to fibrosis in a 2D monocellular culture environment, and the type-II collagen and polysaccharides expressed thereby decrease. To detect the TSL-4 protective effect on chondrocytes injured by hydrogen peroxide accurately, and according to the above experimental results, the $H_2O_2$ molding concentration should be lower than 0.5 mM, and the viability ratio of chondrocytes stimulated by 0.25 mM $H_2O_2$ was about 70%, so a concentration should be selected from the range within 0.25 and 0.5 mM, for example: 0.35 mM $H_2O_2$. In addition, there was a statistical difference (P<0.05) when the concentration of $H_2O_2$ was 0.25 or 0.5 mM, and the optimal dosing concentration of TSL-4 was 1.17 and 5.86 μM. On the contrary, 0.23/29.3 μM TSL-4 had a relatively significantly inhibiting effect on the viability of chondrocytes stimulated by 0.1 mM $H_2O_2$. Therefore, the experiment was repeated for the second time and the dosing concentration of TSL-4 was selected 1.17 and 5.86 μM.

In the presence of the molding agent $H_2O_2$ at 0.25, 0.35, 0.5 mM, 1.17 and 5.86 μM TSL-4 were cultured with chondrocytes for 24 h, and the relative cell viability in each administration group (relative absorbance percentage to the control group) was expressed as the followings $\overline{X} \pm SD$.

TABLE 27

Repeated trials on the effect of hydrogen peroxide and TSL-4 on the viability of chondrocytes

| TSL-4 dosage of administration (μM) | Concentration of molding agent $H_2O_2$ (mM) | | |
| --- | --- | --- | --- |
| | 0.25 | 0.35 | 0.5 |
| 0 | 78.77 ± 7.45 | 63.96 ± 6.46 | 37.10 ± 6.53 |
| 1.17 | 85.31 ± 7.36 | 68.54 ± 3.62 | 41.46 ± 2.08 |
| 5.86 | 87.36 ± 7.85 | 73.29 ± 4.39 | 45.07 ± 6.36 |

The above results indicated that stimulated by three-dosage (0.25, 0.35, 0.5 mM) of $H_2O_2$, chondrocytes injured by $H_2O_2$ achieved improvement in the viability under the conditions of 1.17 and 5.86 μM TSL-4; and in the presence of 0.35 mM of $H_2O_2$, 5.86 μM TSL-4 may significantly improve the viability of chondrocytes. One-way ANOVA served to analyze the comparison of the difference between each administration group and model group at corresponding concentration, * expressed a statistical difference and *P<0.05. Therefore, compared with the model group, the group of co-culturing 5.86 μM TSL-4 and 0.25-0.5 mM for 24 h may significantly improve the viability of chondrocytes injured by $H_2O_2$.

To sum up, the co-incubation of TSL-4 and $H_2O_2$ may remarkably improve the viability of chondrocytes, therefore, TSL-4 and $H_2O_2$ were incubated together for 24 which served as the best administration time. The modeling concentration of hydrogen peroxide ranged within 0.25-0.5, and $H_2O_2$ was incubated with TSL-4 to significantly improve cell viability; TSL-4 achieved better improvement for cell viability at the dosing concentration of 1.17 and 5.86 μM.

The invention claimed is:

1. A fusion protein, formed by linking an HM-3 and IgG-Fc, wherein the HM-3 is a polypeptide linked by a Linker to an N-terminus and/or a C-terminus of the IgG-Fc, and
wherein the fusion protein is selected from the group consisting of
TSL-1, which is HM-3-(GGGGS)$_3$-IgG2-Fc (SEQ ID NO:9);
TSL-2, which is HM-3-(GGGGS)$_3$-mIgG4-Fc (SEQ ID NO:10);
TSL-3, which is IgG2-Fc-(GGGGS)$_3$-HM-3 (SEQ ID NO:11);
TSL-4, which is mIgG4-Fc-(GGGGS)$_3$-HM-3 (SEQ ID NO:12);
TSL-13, which is HM-3-(GGGGS)$_3$-mIgG4-Fc-(GGGGS)$_3$-HM-3 (SEQ ID NO:15);
TSL-15, which is mIgG4-Fc-G5-HM-3-G8-HM-3 (SEQ ID NO:17);
TSL-16, which is HyFc-(GGGGS)$_3$-HM-3 (SEQ ID NO:18);
TSL-17, which is mIgG4-Fc-A(EAAAK)$_4$A-HM-3 (SEQ ID NO:19); and
TSL-18, which is mIgG4-Fc-(AP)$_9$-HM-3 (SEQ ID NO:20).

2. The fusion protein according to claim 1, wherein the fusion protein is TSL-1, TSL-2, TSL-3, or TSL-4.

3. The fusion protein according to claim 1, wherein the fusion protein is TSL-4.

4. The fusion protein according to claim 1, wherein the fusion protein is produced in yeast, CHO cells, SP2/0 cells, BHK cells, HEK293 cells, or any combination thereof.

5. A pharmaceutical composition comprising the fusion protein according to claim 1.

6. The pharmaceutical composition according to claim 5, wherein the pharmaceutical composition is a dosage form selected from the group consisting of an injection, capsule, tablet, pill, nasal spray, and aerosol.

7. The pharmaceutical composition according to claim 5, wherein the pharmaceutical composition is administered by oral administration, intravenous injection, intravenous drip, subcutaneous injection, or intramuscular injection.

8. A method of treating a disease, comprising administration of the pharmaceutical composition of claim 5, wherein the disease is an autoimmune disease, a neovascular disease, or osteoarthritis.

9. The method of claim 8, wherein the disease is an autoimmune disease, wherein the autoimmune disease is rheumatoid arthritis.

10. The method of claim 8, wherein the disease is an autoimmune disease, wherein the neovascular disease is wet age-related macular degeneration.

11. A method of prolonging the half life of HM-3, comprising administration of the fusion protein of claim 1.

* * * * *

SEQUENCE LISTING

<160> NUMBER OF SEQ ID NOS: 28

<210> SEQ ID NO 1
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gctgagtcca aatatggtcc cccatgccca ccctgcccag cacctgaggc cgccggggga      60
ccatcagtct tcctgttccc cccaaaaccc aaggacactc tcatgatctc ccggacccct     120
gaggtcacgt gcgtggtggt ggacgtgagc caggaagacc ccgaggtcca gttcaactgg     180
tacgtggatg gcgtggaggt gcataatgcc aagacaaagc cgcgggagga gcagttcaac     240
agcacgtacc gtgtggtcag cgtcctcacc gtcctgcacc aggactggct gaacggcaag     300
gagtacaagt gcaaggtctc caacaaaggc ctcccgtcct ccatcgagaa aaccatctcc     360
aaagccaaag gcagccccg agagccacag gtgtacaccc tgcccccatc ccaggaggag      420
atgaccaaga accaggtcag cctgacctgc ctggtcaaag gcttctaccc cagcgacatc     480
gccgtggagt gggagagcaa tgggcagccg gagaacaact acaagaccac gcctcccgtg     540
ctggactccg acggctcctt cttcctctac agcaggctaa ccgtggacaa gagcaggtgg     600
caggagggga atgtcttctc atgctccgtg atgcatgagg ctctgcacaa ccactacaca     660
cagaagagcc tctccctgtc tctgggtggc ggcggcggca gcggcggcgg cggcagcggc     720
ggcggcggca gcatcgtccg ccgcgcggac cgcgcggcgg tcccgggcgg cggcggccgc     780
ggcgactga                                                            789
```

<210> SEQ ID NO 2
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gccaccatgg catgccctgg cttcctgtgg gcacttgtga tctccacctg tcttgaattt      60
agcatggctg ctgagtccaa atatggtccc ccatgcccac cctgcccagc acctgaggcc     120
gccggggac catcagtctt cctgttcccc ccaaaaccca aggacactct catgatctcc      180
cggacccctg aggtcacgtg cgtggtggtg gacgtgagcc aggaagaccc cgaggtccag     240
ttcaactggt acgtggatgg cgtggaggtg cataatgcca agacaaagcc gcgggaggag     300
cagttcaaca gcacgtaccg tgtggtcagc gtcctcaccg tcctgcacca ggactggctg     360
aacggcaagg agtacaagtg caaggtctcc aacaaaggcc tcccgtcctc catcgagaaa     420
accatctcca aagccaaagg cagccccga gagccacagg tgtacaccct gcccccatcc      480
caggaggaga tgaccaagaa ccaggtcagc ctgacctgcc tggtcaaagg cttctacccc     540
agcgacatcg ccgtggagtg ggagagcaat gggcagccgg agaacaacta caagaccacg     600
cctcccgtgc tggactccga cggctccttc ttcctctaca gcaggctaac cgtggacaag     660
agcaggtggc aggaggggaa tgtcttctca tgctccgtga tgcatgaggc tctgcacaac     720
cactacacac agaagagcct ctccctgtct ctgggtggcg gcggcggcag cggcggcggc     780
ggcagcggcg gcggcggcag catcgtccgc cgcgcggacc gcgcggcggt cccgggcggc     840
```

```
ggcggccgcg gcgactga                                              858
```

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Val Arg Arg Ala Asp Arg Ala Ala Val Pro Gly Gly Gly Gly Arg
1               5                   10                  15

Gly Asp

<210> SEQ ID NO 4
<211> LENGTH: 232
<212> TYPE: PRT
<213> ORGANISM: Homo sapiens

<400> SEQUENCE: 4

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 5
<211> LENGTH: 228
<212> TYPE: PRT
<213> ORGANISM: Homo sapiens

<400> SEQUENCE: 5

```
Glu Arg Lys Cys Cys Val Cys Pro Pro Cys Pro Ala Pro Pro Val
1               5                   10                  15

Ala Gly Pro Ser Val Phe Leu Phe Pro Lys Pro Lys Asp Thr Leu
            20                  25                  30

Met Ile Ser Arg Thr Pro Glu Val Thr Cys Val Val Asp Val Ser
            35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220

Ser Pro Gly Lys
225

<210> SEQ ID NO 6
<211> LENGTH: 279
<212> TYPE: PRT
<213> ORGANISM: Homo sapiens

<400> SEQUENCE: 6

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Lys Pro Lys
65                  70                  75                  80

Asp Thr Leu Met Ile Ser Arg Thr Pro Glu Val Thr Cys Val Val
                85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
            115                 120                 125

Asn Ser Thr Phe Arg Val Val Ser Val Leu Thr Val Leu His Gln Asp
```

```
            130                 135                 140
Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
                195                 200                 205

Ile Ala Val Glu Trp Glu Ser Ser Gly Gln Pro Glu Asn Asn Tyr Asn
            210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
            275

<210> SEQ ID NO 7
<211> LENGTH: 229
<212> TYPE: PRT
<213> ORGANISM: Homo sapiens

<400> SEQUENCE: 7

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220
```

-continued

Leu Ser Leu Gly Lys
225

<210> SEQ ID NO 8
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
                20                  25                  30

Thr Leu Met Ile Ser Arg Thr Pro Glu Val Thr Cys Val Val Val Asp
            35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly
225

<210> SEQ ID NO 9
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ile Val Arg Arg Ala Asp Arg Ala Ala Val Pro Gly Gly Gly Gly Arg
1               5                   10                  15

Gly Asp Gly Gly Gly Gly Ser Gly Gly Gly Ser Gly Gly Gly Gly
                20                  25                  30

Ser Glu Arg Lys Cys Cys Val Glu Cys Pro Pro Cys Pro Ala Pro Pro
            35                  40                  45

Val Ala Gly Pro Ser Val Phe Leu Phe Pro Pro Lys Pro Asp Thr
            50                  55                  60

Leu Met Ile Ser Arg Thr Pro Glu Val Thr Cys Val Val Asp Val
 65                  70                  75                  80

Ser His Glu Asp Pro Glu Val Gln Phe Asn Trp Tyr Val Asp Gly
                 85                  90                  95

Val Glu Val His Asn Ala Lys Thr Lys Pro Arg Glu Glu Gln Phe Asn Ser
            100                 105                 110

Thr Phe Arg Val Val Ser Val Leu Thr Val Val His Gln Asp Trp Leu
            115                 120                 125

Asn Gly Lys Glu Tyr Lys Cys Lys Val Ser Asn Lys Gly Leu Pro Ala
130                 135                 140

Pro Ile Glu Lys Thr Ile Ser Lys Thr Lys Gly Gln Pro Arg Glu Pro
145                 150                 155                 160

Gln Val Tyr Thr Leu Pro Pro Ser Arg Glu Glu Met Thr Lys Asn Gln
                165                 170                 175

Val Ser Leu Thr Cys Leu Val Lys Gly Phe Tyr Pro Ser Asp Ile Ser
            180                 185                 190

Val Glu Trp Glu Ser Asn Gly Gln Pro Glu Asn Asn Tyr Lys Thr Thr
        195                 200                 205

Pro Pro Met Leu Asp Ser Asp Gly Ser Phe Phe Leu Tyr Ser Lys Leu
210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260

<210> SEQ ID NO 10
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ile Val Arg Arg Ala Asp Arg Ala Ala Val Pro Gly Gly Gly Gly Arg
 1               5                  10                  15

Gly Asp Gly Gly Gly Gly Ser Gly Gly Gly Gly Ser Gly Gly Gly Gly
            20                  25                  30

Ser Ala Glu Ser Lys Tyr Gly Pro Pro Cys Pro Pro Cys Pro Ala Pro
        35                  40                  45

Glu Ala Ala Gly Gly Pro Ser Val Phe Leu Phe Pro Pro Lys Pro Lys
    50                  55                  60

Asp Thr Leu Met Ile Ser Arg Thr Pro Glu Val Thr Cys Val Val Val
 65                  70                  75                  80

Asp Val Ser Gln Glu Asp Pro Glu Val Gln Phe Asn Trp Tyr Val Asp
                85                  90                  95

Gly Val Glu Val His Asn Ala Lys Thr Lys Pro Arg Glu Glu Gln Phe
            100                 105                 110

Asn Ser Thr Tyr Arg Val Val Ser Val Leu Thr Val Leu His Gln Asp
        115                 120                 125

Trp Leu Asn Gly Lys Glu Tyr Lys Cys Lys Val Ser Asn Lys Gly Leu
130                 135                 140

```
Pro Ser Ser Ile Glu Lys Thr Ile Ser Lys Ala Lys Gly Gln Pro Arg
145                 150                 155                 160

Glu Pro Gln Val Tyr Thr Leu Pro Pro Ser Gln Glu Glu Met Thr Lys
                165                 170                 175

Asn Gln Val Ser Leu Thr Cys Leu Val Lys Gly Phe Tyr Pro Ser Asp
            180                 185                 190

Ile Ala Val Glu Trp Glu Ser Asn Gly Gln Pro Glu Asn Asn Tyr Lys
        195                 200                 205

Thr Thr Pro Pro Val Leu Asp Ser Asp Gly Ser Phe Phe Leu Tyr Ser
    210                 215                 220

Arg Leu Thr Val Asp Lys Ser Arg Trp Gln Gln Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Leu Gly
                260

<210> SEQ ID NO 11
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys Gly
    210                 215                 220

Gly Gly Gly Ser Gly Gly Gly Gly Ser Gly Gly Gly Gly Ser Ile Val
```

```
                225                 230                 235                 240
Arg Arg Ala Asp Arg Ala Ala Val Pro Gly Gly Gly Arg Gly Asp
                245                 250                 255

<210> SEQ ID NO 12
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Glu Ser Lys Tyr Gly Pro Pro Cys Pro Cys Pro Ala Pro Glu
1               5                   10                  15

Ala Ala Gly Gly Pro Ser Val Phe Leu Phe Pro Pro Lys Pro Lys Asp
                20                  25                  30

Thr Leu Met Ile Ser Arg Thr Pro Glu Val Thr Cys Val Val Val Asp
                35                  40                  45

Val Ser Gln Glu Asp Pro Glu Val Gln Phe Asn Trp Tyr Val Asp Gly
            50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
                100                 105                 110

Ser Ser Ile Glu Lys Thr Ile Ser Lys Ala Lys Gly Gln Pro Arg Glu
            115                 120                 125

Pro Gln Val Tyr Thr Leu Pro Pro Ser Gln Glu Glu Met Thr Lys Asn
        130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
                180                 185                 190

Leu Thr Val Asp Lys Ser Arg Trp Gln Glu Gly Asn Val Phe Ser Cys
            195                 200                 205

Ser Val Met His Glu Ala Leu His Asn His Tyr Thr Gln Lys Ser Leu
        210                 215                 220

Ser Leu Ser Leu Gly Gly Gly Gly Ser Gly Gly Gly Gly Ser Gly
225                 230                 235                 240

Gly Gly Gly Ser Ile Val Arg Arg Ala Asp Arg Ala Ala Val Pro Gly
                245                 250                 255

Gly Gly Gly Arg Gly Asp
                260

<210> SEQ ID NO 13
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ile Val Arg Arg Ala Asp Arg Ala Ala Val Pro Gly Gly Gly Gly Arg
```

```
  1               5                  10                 15
Gly Asp Gly Gly Gly Ser Gly Gly Gly Ser Gly Gly Gly
            20                 25                 30

Ser Glu Ser Lys Tyr Gly Pro Pro Cys Pro Ser Cys Pro Ala Pro Glu
            35                 40                 45

Phe Leu Gly Gly Pro Ser Val Phe Leu Phe Pro Lys Pro Lys Asp
 50                 55                 60

Thr Leu Met Ile Ser Arg Thr Pro Glu Val Thr Cys Val Val Val Asp
 65                 70                 75                 80

Val Ser Gln Glu Asp Pro Glu Val Gln Phe Asn Trp Tyr Val Asp Gly
                85                 90                 95

Val Glu Val His Asn Ala Lys Thr Lys Pro Arg Glu Glu Gln Phe Asn
            100                105                110

Ser Thr Tyr Arg Val Val Ser Val Leu Thr Val Leu His Gln Asp Trp
            115                120                125

Leu Asn Gly Lys Glu Tyr Lys Cys Lys Val Ser Asn Lys Gly Leu Pro
        130                135                140

Ser Ser Ile Glu Lys Thr Ile Ser Lys Ala Lys Gly Gln Pro Arg Glu
145                150                155                160

Pro Gln Val Tyr Thr Leu Pro Pro Ser Gln Glu Met Thr Lys Asn
                165                170                175

Gln Val Ser Leu Thr Cys Leu Val Lys Gly Phe Tyr Pro Ser Asp Ile
            180                185                190

Ala Val Glu Trp Glu Ser Asn Gly Gln Pro Glu Asn Asn Tyr Lys Thr
            195                200                205

Thr Pro Pro Val Leu Asp Ser Asp Gly Ser Phe Phe Leu Tyr Ser Arg
        210                215                220

Leu Thr Val Asp Lys Ser Arg Trp Gln Glu Gly Asn Val Phe Ser Cys
225                230                235                240

Ser Val Met His Glu Ala Leu His Asn His Tyr Thr Gln Lys Ser Leu
                245                250                255

Ser Leu Ser Leu Gly Lys
                260

<210> SEQ ID NO 14
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ser Lys Tyr Gly Pro Pro Cys Pro Ser Cys Pro Ala Pro Glu Phe
 1               5                  10                 15

Leu Gly Gly Pro Ser Val Phe Leu Phe Pro Lys Pro Lys Asp Thr
            20                 25                 30

Leu Met Ile Ser Arg Thr Pro Glu Val Thr Cys Val Val Val Asp Val
            35                 40                 45

Ser Gln Glu Asp Pro Glu Val Gln Phe Asn Trp Tyr Val Asp Gly Val
        50                 55                 60

Glu Val His Asn Ala Lys Thr Lys Pro Arg Glu Glu Gln Phe Asn Ser
65                 70                 75                 80

Thr Tyr Arg Val Val Ser Val Leu Thr Val Leu His Gln Asp Trp Leu
                85                 90                 95
```

```
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
        115                 120                 125
Gln Val Tyr Thr Leu Pro Pro Ser Gln Glu Met Thr Lys Asn Gln
    130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu
            180                 185                 190
Thr Val Asp Lys Ser Arg Trp Gln Glu Gly Asn Val Phe Ser Cys Ser
        195                 200                 205
Val Met His Glu Ala Leu His Asn His Tyr Thr Gln Lys Ser Leu Ser
    210                 215                 220
Leu Ser Leu Gly Lys Gly Gly Gly Gly Ser Gly Gly Gly Gly Ser Gly
225                 230                 235                 240
Gly Gly Gly Ser Ile Val Arg Arg Ala Asp Arg Ala Ala Val Pro Gly
                245                 250                 255
Gly Gly Gly Arg Gly Asp
            260

<210> SEQ ID NO 15
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ile Val Arg Arg Ala Asp Arg Ala Ala Val Pro Gly Gly Gly Gly Arg
1               5                   10                  15
Gly Asp Gly Gly Gly Gly Ser Gly Gly Gly Gly Ser Gly Gly Gly Gly
            20                  25                  30
Ser Ala Glu Ser Lys Tyr Gly Pro Pro Cys Pro Pro Cys Pro Ala Pro
        35                  40                  45
Glu Ala Ala Gly Gly Pro Ser Val Phe Leu Phe Pro Pro Lys Pro Lys
    50                  55                  60
Asp Thr Leu Met Ile Ser Arg Thr Pro Glu Val Thr Cys Val Val Val
65                  70                  75                  80
Asp Val Ser Gln Glu Asp Pro Glu Val Gln Phe Asn Trp Tyr Val Asp
                85                  90                  95
Gly Val Glu Val His Asn Ala Lys Thr Lys Pro Arg Glu Glu Gln Phe
            100                 105                 110
Asn Ser Thr Tyr Arg Val Val Ser Val Leu Thr Val Leu His Gln Asp
        115                 120                 125
Trp Leu Asn Gly Lys Glu Tyr Lys Cys Lys Val Ser Asn Lys Gly Leu
    130                 135                 140
Pro Ser Ser Ile Glu Lys Thr Ile Ser Lys Ala Lys Gly Gln Pro Arg
145                 150                 155                 160
Glu Pro Gln Val Tyr Thr Leu Pro Pro Ser Gln Glu Glu Met Thr Lys
                165                 170                 175
Asn Gln Val Ser Leu Thr Cys Leu Val Lys Gly Phe Tyr Pro Ser Asp
            180                 185                 190
```

```
Ile Ala Val Glu Trp Glu Ser Asn Gly Gln Pro Glu Asn Asn Tyr Lys
            195                 200                 205

Thr Thr Pro Pro Val Leu Asp Ser Asp Gly Ser Phe Phe Leu Tyr Ser
225                 230                 235                 240

Arg Leu Thr Val Asp Lys Ser Arg Trp Gln Glu Gly Asn Val Phe Ser
225                 230                 235                 240

Cys Ser Val Met His Glu Ala Leu His Asn His Tyr Thr Gln Lys Ser
            245                 250                 255

Leu Ser Leu Ser Leu Gly Gly Gly Gly Ser Gly Gly Gly Gly Ser
            260                 265                 270

Gly Gly Gly Gly Ser Ile Val Arg Arg Ala Asp Arg Ala Ala Val Pro
            275                 280                 285

Gly Gly Gly Gly Arg Gly Asp
            290                 295

<210> SEQ ID NO 16
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ile Val Arg Arg Ala Asp Arg Ala Ala Val Pro Gly Gly Gly Gly Arg
1               5                   10                  15

Gly Asp Arg Asn Thr Gly Arg Gly Gly Glu Glu Lys Lys Lys Glu Lys
                20                  25                  30

Glu Lys Glu Glu Gln Glu Glu Arg Glu Thr Lys Thr Pro Glu Cys Pro
            35                  40                  45

Ser His Thr Gln Pro Leu Gly Val Phe Leu Phe Pro Pro Lys Pro Lys
        50                  55                  60

Asp Thr Leu Met Ile Ser Arg Thr Pro Glu Val Thr Cys Val Val Val
65                  70                  75                  80

Asp Val Ser Gln Glu Asp Pro Glu Val Gln Phe Asn Trp Tyr Val Asp
                85                  90                  95

Gly Val Glu Val His Asn Ala Lys Thr Lys Pro Arg Glu Glu Gln Phe
            100                 105                 110

Asn Ser Thr Tyr Arg Val Val Ser Val Leu Thr Val Leu His Gln Asp
        115                 120                 125

Trp Leu Asn Gly Lys Glu Tyr Lys Cys Lys Val Ser Asn Lys Gly Leu
130                 135                 140

Pro Ser Ser Ile Glu Lys Thr Ile Ser Lys Ala Lys Gly Gln Pro Arg
145                 150                 155                 160

Glu Pro Gln Val Tyr Thr Leu Pro Pro Ser Gln Glu Glu Met Thr Lys
                165                 170                 175

Asn Gln Val Ser Leu Thr Cys Leu Val Lys Gly Phe Tyr Pro Ser Asp
            180                 185                 190

Ile Ala Val Glu Trp Glu Ser Asn Gly Gln Pro Glu Asn Asn Tyr Lys
        195                 200                 205

Thr Thr Pro Pro Val Leu Asp Ser Asp Gly Ser Phe Phe Leu Tyr Ser
    210                 215                 220

Arg Leu Thr Val Asp Lys Ser Arg Trp Gln Glu Gly Asn Val Phe Ser
225                 230                 235                 240

Cys Ser Val Met His Glu Ala Leu His Asn His Tyr Thr Gln Lys Ser
```

Leu Ser Leu Ser Leu Gly Lys
            260

<210> SEQ ID NO 17
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Gly Gly Gly Gly Ile Val Arg Arg Ala Asp
225                 230                 235                 240

Arg Ala Ala Val Pro Gly Gly Gly Arg Gly Asp Gly Gly Gly
            245                 250                 255

Gly Gly Gly Gly Ile Val Arg Arg Ala Asp Arg Ala Ala Val Pro Gly
        260                 265                 270

Gly Gly Gly Arg Gly Asp
        275

<210> SEQ ID NO 18
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Arg Asn Thr Gly Arg Gly Gly Glu Lys Lys Glu Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys Gly Gly Gly Ser Gly Gly Gly Ser Gly
                245                 250                 255

Gly Gly Gly Ser Ile Val Arg Arg Ala Asp Arg Ala Ala Val Pro Gly
            260                 265                 270

Gly Gly Gly Arg Gly Asp
        275
```

<210> SEQ ID NO 19
<211> LENGTH: 269
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60
```

```
Val Glu Val His Asn Ala Lys Thr Lys Pro Arg Glu Glu Gln Phe Asn
 65                  70                  75                  80

Ser Thr Tyr Arg Val Val Ser Val Leu Thr Val Leu His Gln Asp Trp
                 85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Ala Glu Ala Ala Ala Lys Glu Ala Ala Ala Lys
225                 230                 235                 240

Glu Ala Ala Ala Lys Glu Ala Ala Ala Lys Ala Ile Val Arg Arg Ala
                245                 250                 255

Asp Arg Ala Ala Val Pro Gly Gly Gly Gly Arg Gly Asp
            260                 265

<210> SEQ ID NO 20
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Lys Pro Lys Asp
                20                  25                  30

Thr Leu Met Ile Ser Arg Thr Pro Glu Val Thr Cys Val Val Val Asp
            35                  40                  45

Val Ser Gln Glu Asp Pro Glu Val Gln Phe Asn Trp Tyr Val Asp Gly
 50                  55                  60

Val Glu Val His Asn Ala Lys Thr Lys Pro Arg Glu Glu Gln Phe Asn
 65                  70                  75                  80

Ser Thr Tyr Arg Val Val Ser Val Leu Thr Val Leu His Gln Asp Trp
                 85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160
```

```
Ala Val Glu Trp Glu Ser Asn Gly Gln Pro Glu Asn Asn Tyr Lys Thr
            165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
            195                 200                 205

Ser Val Met His Glu Ala Leu His Asn His Tyr Thr Gln Lys Ser Leu
            210                 215                 220

Ser Leu Ser Leu Gly Ala Pro Ala Pro Ala Pro Ala Pro Ala Pro Ala
225                 230                 235                 240

Pro Ala Pro Ala Pro Ala Pro Ile Val Arg Arg Ala Asp Arg Ala Ala
                245                 250                 255

Val Pro Gly Gly Gly Gly Arg Gly Asp
            260                 265
```

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-6 "Gly Gly Gly
      Gly Ser" repeating units

<400> SEQUENCE: 21

```
Gly Gly Gly Gly Ser Gly Gly Gly Ser Gly Gly Gly Gly Ser Gly
1               5                   10                  15

Gly Gly Ser Gly Gly Gly Gly Ser Gly Gly Gly Gly Ser
            20                  25                  30
```

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (2)..(31)
<223> OTHER INFORMATION: This region may encompass 1-6 "Glu Ala Ala Ala
      Lys" repeating units

<400> SEQUENCE: 22

```
Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Glu Ala Ala Ala Lys Ala
            20                  25                  30
```

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(36)
<223> OTHER INFORMATION: This sequence may encompass 1-18 "Ala Pro"
      repeating units

<400> SEQUENCE: 23

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro
        35

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1-15 residues

<400> SEQUENCE: 24

Gly Gly Gly Gly Gly Gly Gly Gly Gly Gly Gly Gly Gly Gly Gly
1               5                   10                  15

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 3-5 "Gly Gly Gly
      Gly Ser" repeating units

<400> SEQUENCE: 25

Gly Gly Gly Gly Ser Gly Gly Gly Gly Ser Gly Gly Gly Gly Ser Gly
1               5                   10                  15

Gly Gly Ser Gly Gly Gly Gly Ser
            20                  25

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Gly Gly Ser Gly Gly Gly Gly Ser Gly Gly Gly Gly Ser
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Glu Ala Ala Ala Lys Ala
1               5

```
<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser
1               5
```